(12) United States Patent
Bacque et al.

(10) Patent No.: US 6,541,451 B1
(45) Date of Patent: Apr. 1, 2003

(54) STREPTOGRAMIN DERIVATIVES, THEIR PREPARATION AND COMPOSITIONS CONTAINING THEM

(75) Inventors: Eric Bacque, Morsang sur Orge (FR); Jean-Claude Barriere, Bures sur Yvette (FR); Gilles Doerflinger, Les Ulis (FR); Gilles Dutruc-Rosset, Paris (FR); Guy Pantel, La Queue en Brie (FR)

(73) Assignee: Aventis Pharma S.A., Antony (FR)

( * ) Notice: Subject to any disclaimer, the term of this patent is extended or adjusted under 35 U.S.C. 154(b) by 17 days.

(21) Appl. No.: 09/627,791

(22) Filed: Jul. 27, 2000

Related U.S. Application Data
(60) Provisional application No. 60/152,270, filed on Sep. 3, 1999.

(30) Foreign Application Priority Data
Jul. 27, 1999 (FR) ............................................. 99 09708

(51) Int. Cl.$^7$ ............................ A61K 37/08; C07K 7/06
(52) U.S. Cl. ......................................... 514/11; 530/329
(58) Field of Search ................................ 514/9, 11, 16, 514/17; 530/317, 321, 323, 329

(56) References Cited

U.S. PATENT DOCUMENTS

| | | | | |
|---|---|---|---|---|
| 4,618,599 A | * | 10/1986 | Corbet et al. ................. | 514/11 |
| 4,668,669 A | * | 5/1987 | Barriere et al. ............. | 514/183 |
| 4,798,827 A | * | 1/1989 | Barriere et al. ............. | 514/183 |
| 5,786,449 A | | 7/1998 | Barriere et al. ............. | 530/317 |
| 5,789,537 A | | 8/1998 | Barriere et al. ............. | 530/317 |

FOREIGN PATENT DOCUMENTS

| | | |
|---|---|---|
| FR | 2 722 210 | 1/1996 |
| FR | 2 723 372 | 2/1996 |
| WO | WO 96 33213 | 10/1996 |

OTHER PUBLICATIONS

English Language Derwent Abstract of FR 2 722 210 (Jan. 12, 1996).
U.S. patent application Ser. No. 09/609,717—Copy of as–filed U.S. application, filed Jun. 30, 2000 (Daniel Archard et al.) (121 pages, including 15 claims); Preliminary Amendment filed Jan. 26, 2001, which cancels claims 1–15 and adds claims 16–47; Amendment filed Nov. 7, 2001, amends claims 16, 40 and 45; and Amendment filed Mar. 7, 2002, which amends claim 16.

U.S. patent application Ser. No. 09/643,197—Copy of as–filed U.S. application, filed Aug. 22, 2000 (Pascal Desmazeau et. al.) (285 pages, including abstract and 17 claims); Preliminary Amendment filed Jun. 21, 2001, cancels claims 1–17 and adds claims 18–34); and Amendment filed Mar. 11, 2002, which amends claims 18 and 31 in response to a restriction requirement.

U.S. patent application Ser. No. 10/055,888—Copy of as filed U. S. application, filed Jan. 28, 2002 (Eric Bacque et al.) (72 pages, including abstract and 16 claims).

\* cited by examiner

*Primary Examiner*—Jeffrey E. Russel
(74) *Attorney, Agent, or Firm*—Finnegan, Henderson, Farabow, Garrett, & Dunner LLP

(57) ABSTRACT

B-Group streptogramin compounds of formula (I):

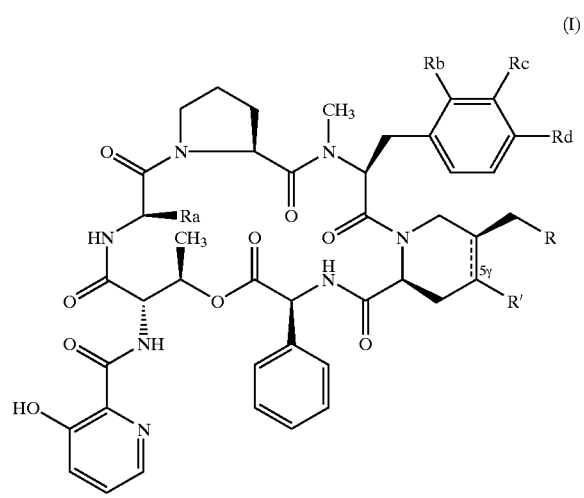

are useful as antimicrobial agents, optionally combined with at least one A-group streptogramin compound.

26 Claims, No Drawings

STREPTOGRAMIN DERIVATIVES, THEIR PREPARATION AND COMPOSITIONS CONTAINING THEM

This application claims priority of U.S. Provisional Application No. 60/152,270, filed Sep. 3, 1999.

The present invention relates to B-group streptogramin compounds of formula (I):

(I)

as well as the salts thereof, which exhibit antibacterial activity alone or in combination with an A-group streptogramin compound.

Among the known streptogramins, pristinamycin (RP 7293), an antibacterial agent of natural origin produced by *Streptomyces pristinaespiralis*, was isolated for the first time in 1955. The pristinamycin sold under the name Pyostacine® comprises mainly pristinamycin IA combined with pristinamycin IIA.

Another antibacterial agent of the streptogramin family, virginiamycin, was isolated from *Streptomyces virginiae*, ATCC 13161 (*Antibiotics and Chemotherapy*, 5, 632 (1955)). Virginiamycin (Staphylomycine®) comprises mainly factor S combined with factor $M_1$.

Semisynthetic derivatives of streptogramins represented by formula (A):

(A)

wherein:

Ra is a radical of structure —$CH_2R'a$ for which R'a is a radical of the heterocyclylthio type which may be substituted, or alternatively represents a radical of structure =CHR'a for which R'a is a substituted alkylamino, alkyloxy or alkylthio radical, or a radical of the heterocyclylamino, heterocyclyloxy or heterocyclylthio type which may be substituted, Rb and Rc are hydrogen atoms and Rd is a hydrogen atom or a dimethylamino radical, or alternatively Ra is a hydrogen atom and Rb is hydrogen or methyl, and Rc and Rd are hydrogen or various substituents, have been described in European Patent Nos. EP 133 097, EP 248 703, EP 770 132, and EP 772 630.

When combined with a semisynthetic component of the streptogramin A group, they can show synergistic action and can be used as antibacterial agents, administered either via injection or orally.

European Patent No. EP 133 098 also discloses B-group synergistin derivatives bearing aminomethylenyl chains in position 5δ, which are synthetic intermediates.

It has now been found, in accordance with the present invention, that the compounds of formula (I), wherein:

R is chosen from —$NR_1R_2$ and —$SR_3$, wherein:
  $R_1$ and $R_2$, which may be identical or different, are independently chosen from a hydrogen atom and the radicals:
    alkyl(1 to 8 carbons), which are unsubstituted or substituted with hydroxyl;
    alkenyl (3 to 8 carbons);
    cycloalkyl (3 to 8 carbons);
    alkyloxy (1 to 8 carbons);
    dialkylamino;
    phenylalkyl, which is unsubstituted or substituted with one or more halogen atoms or radicals chosen from alkyl, hydroxyalkyl, alkyloxy, and dialkylamino;
    saturated and unsaturated heterocyclylalkyl (3- to 8-membered) containing one or more hetero atoms chosen from nitrogen, sulphur and oxygen; and dialkylaminoalkyl;
  or, alternatively,
    $R_1$ and $R_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
    hydroxyl;
    alkyl;
    phenyl, which is unsubstituted or substituted with a halogen atom;
    phenylalkyl;
    phenylalkenyl (alkenyl containing 2 to 4 carbons);
    hydroxyalkyl;
    acyl;
    alkyloxycarbonyl; and
    heterocyclyl and heterocyclylcarbonyl, wherein the heterocyclyl portion is saturated or unsaturated (4- to 6-membered) and contains one or more hetero atoms chosen from oxygen, sulphur, and nitrogen;
  $R_3$ is chosen from:
    alkyl (containing 1 to 8 carbons) and cycloalkyl (containing 3 to 8 carbons) radicals, both of which are substituted with a radical chosen from:
    —$NR_1R_2$, wherein $R_1$ and $R_2$, which may be identical or different, are chosen from:

a hydrogen atom; and
alkyl radicals;
or form, together with the nitrogen atom to which they are attached, a heterocycle as defined above;
or, alternatively,
R₃ is chosen from 3- to 7-membered, saturated and unsaturated, monocyclic and polycyclic, heterocyclyl and heterocyclylmethyl radicals optionally containing at least one additional hetero atom chosen from oxygen, sulphur, and nitrogen, and which are unsubstituted or substituted with at least one alkyl radical;

represents an unsaturated ring residue which is unsubstituted at 5γ:

or a saturated ring residue which is substituted at 5γ with a fluoro radical:

Ra is chosen from methyl and ethyl radicals; and
Rb, Rc, and Rd have the following definitions:
1) Rb and Rc are both a hydrogen atom; and
   Rd is chosen from a hydrogen atom and methylamino and dimethylamino radicals;
2) Rb is a hydrogen atom;
   Rc is chosen from hydrogen, chlorine, and bromine atoms, and alkenyl radicals (3 to 5 carbons); and Rd is a radical —NMe—R''', wherein R''' is chosen from:
   alkyl, hydroxyalkyl (2 to 4 carbons), and alkenyl (2 to 8 carbons) radicals, which are unsubstituted or substituted with at least one radical chosen from:
      phenyl;
      cycloalkyl (3 to 6 carbons);
      methyl;
      benzyl; and
      substituted benzyl, wherein one or more substitutents are chosen from:
         halogen atoms and hydroxyl, alkyl, alkyloxy, alkylthio, alkylsulphinyl, alkylsulphonyl, amino, alkylamino and dialkylamino radicals; and
   heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:
      alkyl, alkenyl (2 to 8 carbons), cycloalkyl (3 to 6 carbons), saturated and unsaturated 4- to 6-membered heterocyclyl, phenyl, substituted phenyl as defined above for the definition of R₁, and benzyl radicals;
   or, alternatively,
   R''' is chosen from cyanomethyl, carboxymethyl, —CORe and —CH₂CORe radicals, wherein Re is —OR'e, and wherein R'e is chosen from:
      alkyl (1 to 6 carbons);
      alkenyl (2 to 6 carbons);
      benzyl;
      phenyl;
      tolyl; and
      heterocyclylmethyl radicals, wherein:
         the heterocyclyl portion is 5- or 6-membered and contains 1 or 2 hetero atoms chosen from sulphur, oxygen and nitrogen;
   or, alternatively,
   Re is chosen from:
      alkylamino;
      alkylmethylamino; and
      heterocyclylamino and heterocyclylmethylamino radicals, wherein:
         the heterocyclyl radical is saturated and 5- or 6-membered and contains 1 or 2 hetero atoms chosen from sulphur, oxygen, and nitrogen, and is unsubstituted or substituted with a radical chosen from alkyl, benzyl, and alkyloxycarbonyl radicals;
3) Rb is a hydrogen atom;
   Rd is chosen from —NHCH₃ and —N(CH₃)₂ radicals; and Rc is chosen from chlorine and bromine atoms, and from alkenyl radicals (3 to 5 carbons) when Rd is —N(CH₃)₂;
4) Rb and Rd are both a hydrogen atom; and
   Rc is chosen from halogen atoms and alkylamino, dialkylamino, alkyloxy, trifluoromethoxy, thioalkyl, alkyl (1 to 6 carbons), and trihalomethyl radicals;
5) Rb and Rc are both a hydrogen atom; and
   Rd is chosen from halogen atoms and ethylamino, diethylamino, methylethylamino, alkyloxy, trifluoromethoxy, alkylthio, alkylsulphinyl, alkylsulphonyl, alkyl (1 to 6 carbons), phenyl, and trihalomethyl radicals;
6) Rb is a hydrogen atom;
   Rc is chosen from halogen atoms and alkylamino, dialkylamino, alkyloxy, trifluoromethoxy, thioalkyl, and alkyl (1 to 3 carbons) radicals; and
   Rd is chosen from halogen atoms and amino, alkylamino, dialkylamino, alkyloxy, trifluoromethoxy, thioalkyl, alkyl (1 to 6 carbons), and trihalomethyl radicals; and
7) Rc is a hydrogen atom; and
   Rb and Rd are both methyl radicals; show particularly advantageous activities for treating infections when administered orally and/or parenterally.

The streptogramin compounds of formula (I) may exhibit powerful oral and parenteral activity, which makes them extremely useful for treating serious infections, for example, in a hospital environment via injection, which administration may be followed by an oral ambulatory treatment which is easier to administer to the patients. Thus, the practitioner is no longer obliged to change the patient's category of medicinal product between the end of the hospital treatment and the overall end of the treatment.

In the formula (I) above, the halogen atoms can be chosen from fluorine, chlorine, bromine, and iodine; the alkyl and acyl radicals are straight or branched and, except where specifically mentioned, may contain from 1 to 4 carbon atoms. The alkenyl radicals can also be in the form of a straight or branched chain, and can contain from 2 to 4 carbon atoms.

It is also understood that, in the above definitions, when R₁ and R₂ represent heterocyclylalkyl, they comprise a heterocyclyl radical or form a heterocycle together with the nitrogen atom to which they are attached, or when $R_3$ represents a heterocyclyl or heterocyclylmethyl radical, wherein the heterocyclyl portion of the radical can be saturated or unsaturated and optionally polycyclic, such as, for example, bicyclic or tricyclic.

Among the heterocyclyl radicals mentioned above, those which may be mentioned include, for example, pyrrolyl, pyrrolidinyl, piperidinyl, pyrazinyl, pyrimidinyl, piperazinyl, pyridyl, tetrahydropyridyl, tetrahydroquinolyl, tetrahydroisoquinolyl, morpholinyl, thiomorpholinyl, thiazolyl, oxazolyl, imidazolidinyl, imidazolyl, benzimidazolyl, furyl, thienyl, and dioxolanyl radicals.

According to one aspect of the invention, the compounds of formula (I) can be prepared by the action of a fluorinating agent on the B-group synergistin compound of formula (II):

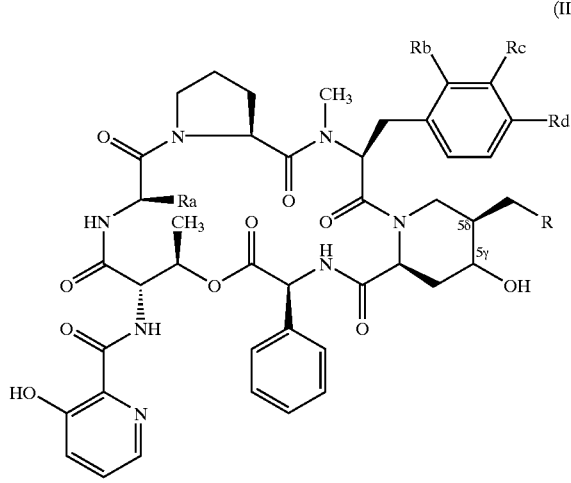

(II)

wherein R, Ra, Rb, Rc, and Rd are defined as above, followed by separation of the fluoro derivative or of the derivative which is unsaturated in the 5γ-5δ position.

The reaction is generally performed by the action of a fluorinating agent such as a sulphur fluoride, for example, aminosulphur trifluoride: morpholinosulphur trifluoride, diethylaminosulphur trifluoride (*Tetrahedron*, 44, 2875 (1988), bis(2-methoxyethyl)aminosulphur trifluoride (Deoxofluor®) or, for example, sulphur tetrafluoride (*J. Org. Chem.*, 40, 3808 (1975), the disclosures of which are incorporated herein by reference, or an agent such as hexafluoropropyldiethylamine (Japanese Patent No. JP 2 039 546, the disclosure of which is incorporated herein by reference) or N-(2-chloro-1,1,2-trifluoroethyl)diethylamine. The reaction can be performed in an organic solvent such as, for example, a chlorinated solvent, such as dichloromethane, dichloroethane, or chloroform, at a temperature ranging from –70° C. to 50° C. and in an inert medium, for example, under argon or nitrogen.

The fluoro derivative and the unsaturated derivative wherein:

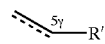

represents:

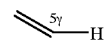

are separated according to the usual methods which do not adversely affect the rest of the molecule, for example, by performing a chromatography or a crystallization.

According to another aspect of the invention, the synergistin compounds of formula (I), wherein

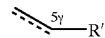

represents:

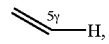

can be prepared by the action of a thionyl halide, in the presence of a nitrogenous base, on the B-group synergistin compound of formula (II).

The reaction is performed by treating thionyl chloride or bromide in the presence of a nitrogenous base such as, for example, triethylamine or pyridine at a temperature ranging from –50° C. to +80° C., in a chlorinated solvent such as, for example, dichloromethane, 1,2-dichloroethane, or chloroform, or an ether such as, for example, tetrahydrofuran (THF).

The B-group synergistin compounds of formula (II) can be prepared by reducing the 5γ ketone function of a streptogramin compound of formula (III):

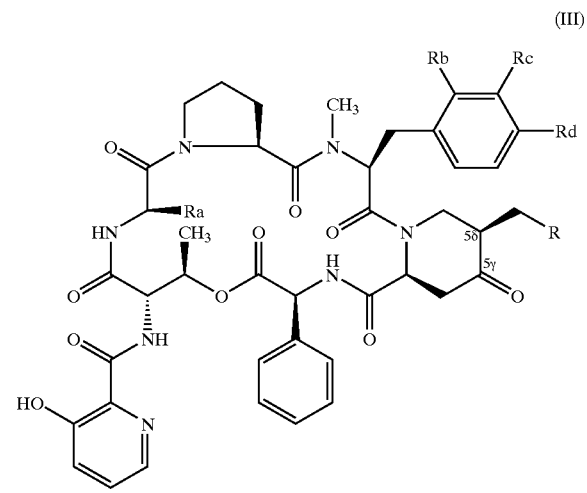

(III)

wherein R, Ra, Rb, Rc, and Rd are defined as above, according to the usual methods which do not adversely affect the rest of the molecule.

The process is performed by treatment with a reducing agent such as a hydride, for example an alkaline borohydride such as, for example, sodium borohydride, potassium borohydride, sodium triacetoxyborohydride, and sodium cyanoborohydride, at a temperature ranging from –70° C. to 60° C., in an organic solvent such as an ether, for example, THF, or an alcohol, for example, methanol or ethanol, or a chlorinated solvent, for example, dichloromethane.

The streptogramin compound of formula (III) can be prepared according to, or by analogy with, the methods described in European Patent Nos. EP 133 097, EP 133 098, EP 248 703, EP 432 029, EP 770 132, and EP 772 630, the disclosures of which are incorporated herein by reference.

According to the invention, the streptogramin compounds of formula (I) wherein the symbol

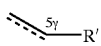

represents

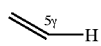

can also be prepared by the action of an amine $HNR_1R_2$ or a thiol $HS-R_3$ on a halogenated streptogramin compound of formula (IV):

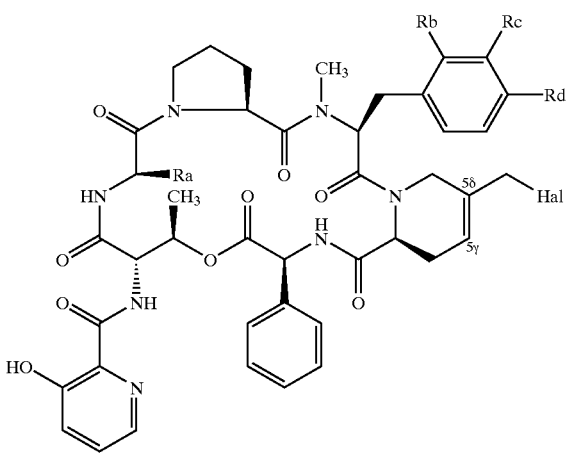

wherein Ra, Rb, Rc, and Rd are defined as above, and Hal represents a halogen atom.

According to certain embodiments, the symbol Hal represents a chlorine or bromine atom.

The reaction of the amines $R_1R_2NH$ is performed in an organic solvent such as an amide, for example, dimethylformamide, or a nitrite, for example, acetonitrile, or a chlorinated solvent, for example, chloroform, at a temperature ranging from 0° C. to 80° C. The process is optionally performed in the presence of triethylamine. When a thiol $HS-R_3$ is reacted, the process is performed in basic medium, for example, in the presence of an alkaline hydride, for example, sodium hydride, in an organic solvent such as an amide, for example, dimethylformamide, or a nitrite, for example, acetonitrile, optionally in the presence of triethylamine, at a temperature ranging from 0° C. to 80° C.

The streptogramin compounds of formula (IV) can be prepared by treating a 5δ-methylene streptogramin of formula (V):

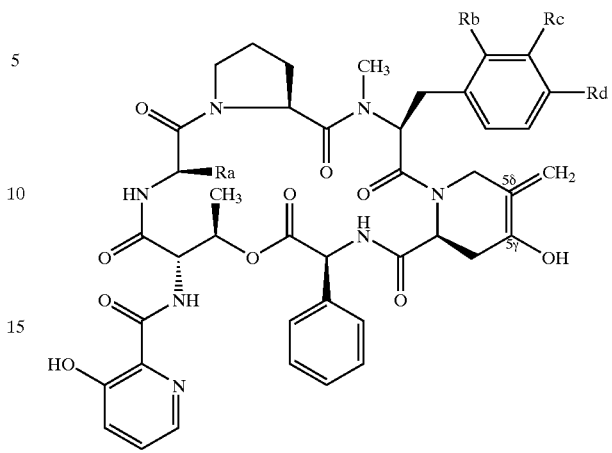

wherein Ra, Rb, Rc, and Rd are defined as above, with a halogenating agent.

The process can be performed using common halogenating agents which do not adversely affect the rest of the molecule. For example, thionyl chloride or bromide is reacted in an organic solvent such as a chlorinated solvent, for example, dichloromethane, dichloroethane, or chloroform, or an ether, for example, tetrahydrofuran, or the process is performed in a mixture of these solvents, at a temperature ranging from −60° C. to 80° C.

The streptogramin compounds of formula (V) can be prepared by reducing the 5γ ketone function of a synergistin compound of formula (VI):

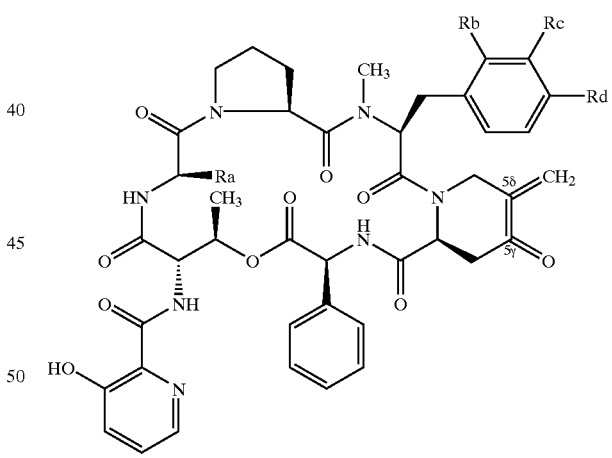

wherein Ra, Rb, Rc, and Rd are defined as above.

The reaction is performed under conditions similar to the conditions described for obtaining a streptogramin compound of formula (II) from a compound of formula (III). The process may be performed in an organic solvent such as an alcohol, for example, methanol, or a chlorinated solvent, for example, dichloromethane, dichloroethane, or chloroform, or in a mixture of alcoholic solvent/chlorinated solvent, for example, methanol/dichloromethane, in the presence of anhydrous cerium chloride, at a temperature ranging from −60° C. to 60° C.

The streptogramin compounds of formula (VI) can be prepared according to the methods described in European Patent Nos. EP 133 098 and EP 432 029, or by analogy with these methods, or the methods described in European Patent Nos. EP 248 703, EP 770 132, EP 772 630, EP 821 697, and International Patent Application No. WO 99/43699, the disclosures of which are all incorporated herein by reference, as well as the methods described hereinbelow in the examples.

The streptogramin compounds of formula (I) or (IV) can be purified, if necessary, by physical methods such as crystallization or chromatography.

The streptogramin compounds of formula (II), wherein R, Ra, Rb, Rc, and Rd are as defined above, are novel compounds. It is understood that these compounds also fall within the scope of the present invention.

Some of the streptogramin compounds of formula (I) can be converted into the form of addition salts with acids, by known methods. It is understood that these salts are also part of the present invention. As examples of addition salts with pharmaceutically acceptable acids, mention may be made of the salts formed with inorganic acids such as, for example, hydrochlorides, hydrobromides, sulphates, nitrates, and phosphates, or with organic acids such as, for example, succinates, fumarates, tartrates, acetates, propionates, maleates, citrates, methanesulphonates, ethanesulphonates, phenylsulphonates, p-toluenesulphonates, isethionates, naphthalenesulphonates, or camphorsulphonates, or with substitution derivatives of these compounds.

Where appropriate, the compounds bearing a carboxyl substituent may be converted into metal salts or into addition salts with nitrogenous bases according to the methods that are known per se. These salts can be obtained by the action of a metallic base, for example, alkali metal or alkaline-earth metal bases, ammonia, or an amine on a compound according to the invention, in a suitable solvent such as an alcohol, an ether, or water, or by exchange reaction with a salt of an organic acid. The salt formed precipitates after optionally concentrating the solution, and is separated out by filtration, settling, or lyophilization. Examples of pharmaceutically acceptable salts which may be mentioned include the salts with alkali metals such as, for example, sodium, potassium, and lithium, or with alkaline-earth metals such as, for example, magnesium or calcium, the ammonium salt, the salts of nitrogenous bases such as, for example, ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, or dibenzylamine.

The streptogramin compounds according to the present invention may have antibacterial properties and synergizing properties with respect to the antibacterial activity of the A-group streptogramin compounds. They may be useful on account of their activity, alone or in combination with A-group streptogramin components. They may also be useful on account of their activity, both orally and parenterally, which opens the way to an ambulatory relay treatment without modifying the nature of the medicinal product.

When they are combined with an A-group streptogramin component or derivative, these components or derivatives can be chosen, depending on whether it is desired to obtain a form for oral or parenteral administration, from the following natural components: pristinamycin IIA, pristinamycin IIB, pristinamycin IIC, pristinamycin IID, pristinamycin IIE, pristinamycin IIF, and pristinamycin IIG, or from semisynthetic derivatives as described in U.S. Pat. No. 4,590,004 and European Patent No. EP 191 662, the disclosures of which are incorporated herein by reference, or alternatively from the semisynthetic compounds of formula (α):

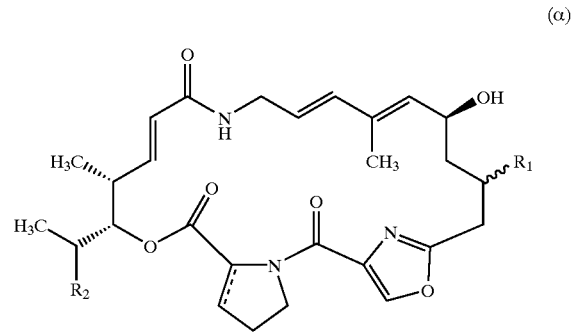

(α)

described in International patent application WO 99/051265, the disclosure of which is incorporated herein by reference, wherein $R_1$ is a radical —NR'R" for which R' is a hydrogen atom or a methyl radical, and R" is a hydrogen atom or an alkyl, cycloalkyl, allyl, propargyl or benzyl radical or a radical —OR'", R'" being a hydrogen atom or an alkyl, cycloalkyl, allyl, propargyl or benzyl radical, or —NR$_3$R$_4$, $R_3$ and $R_4$ possibly representing a methyl radical or forming, together with the nitrogen atom to which they are attached, a saturated or unsaturated 4- or 5-membered heterocycle which can also contain another hetero atom chosen from nitrogen, oxygen and sulphur, $R_2$ is a hydrogen atom or a methyl or ethyl radical, and the bond - - - represents a single bond or a double bond, as well as the salts thereof.

The A-group streptogramin compounds which may be combined therewith can also be chosen from semisynthetic compounds of formula (β):

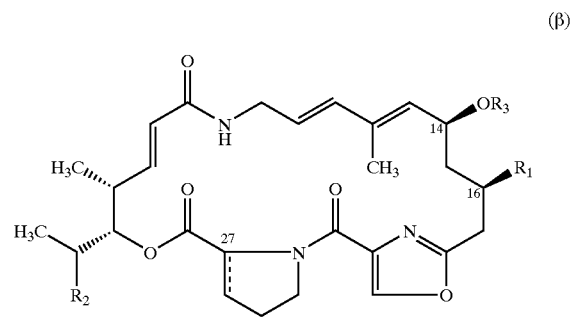

(β)

wherein:
  $R_1$ is chosen from halogen atoms and azido and thiocyanato radicals;
  $R_2$ is chosen from hydrogen atoms and methyl and ethyl radicals;
  $R_3$ is chosen from hydrogen atoms and aliphatic, cycloaliphatic, aromatic, araliphatic, heterocyclic and heterocyclylaliphatic ester residues which may be substituted or unsubstituted; and
  the bond - - - represents a single bond (27R stereochemistry) or a double bond; and the salts thereof.

According to one embodiment, the compounds of formula (β) that can be combined therewith include those wherein the ester residue $R_3$ is chosen from:
  R'$_3$—CO— radicals, wherein R'$_3$ is chosen from:
    phenyl and phenylalkyl radicals, which are unsubstituted or substituted on the phenyl radical with one or more radicals chosen from:

alkyl radicals, optionally bearing a radical NR"R'"
wherein the radicals R" and R'", which may be
identical or different, are chosen from:
a hydrogen atom and alkyl radicals which can
form, together with the nitrogen atom to which
they are attached, saturated and unsaturated 3-
to 8-membered heterocyclyl radicals, option-
ally comprising at least one additional hetero
atom chosen from oxygen, sulphur, and
nitrogen, it being possible for the heterocycle
itself to be substituted with one or more radi-
cals chosen from saturated and unsaturated 3-
to 8-membered alkyl, hydroxyalkyl,
alkyloxyalkyl, alkyloxycarbonylalkyl, aryl,
heterocyclyl, heterocyclylalkyl, and —CH$_2$—
CO—NR"R'";
or, alternatively,
R" and R'" are chosen from:
saturated and unsaturated 3- to 8-membered
hydroxyalkyl, phenyl, and heterocyclylalkyl
radicals, a radical —CO—NR"R'" wherein
NR"R'" is defined as above, and alkyl and acyl
radicals, substituted with NR"R'" defined as
above;
or, alternatively,
R'$_3$ is chosen from phenyl and phenylalkyl radicals
which are substituted on the phenyl radical with one
or more radicals chosen from:
alkyl, which is unsubstituted or substituted with
alkyloxy and alkylthio radicals, themselves
optionally bearing a carboxyl radical or a radical
NR"R'" defined as above, or chosen from acyloxy
which can be substituted with NR"R'" defined as
above;
or, alternatively,
R'$_3$ is chosen from alkyl and cycloalkyl radicals which
are unsubstituted or substituted with at least one
radical chosen from carboxyl,
carboxyalkyldisulphanyl, NR"R'", —CH$_2$—NR"R'",
—CO—NR"R'", alkyloxycarbonyl, alkyloxy, and
alkyldisulphanyl radicals, which are unsubstituted or
substituted with at least one radical chosen from:
NR"R'" and —CO—NR"R'", wherein NR"R'" is
defined as above;
or, alternatively,
R'$_3$ is chosen from saturated and unsaturated 3- to
8-membered heterocyclyl radicals which are unsub-
stituted or substituted with at least one radical chosen
from alkyl and acyl radicals, both of which are
unsubstituted or substituted with NR"R'".

It is understood in the formula (β) above that, when R$_1$ is halogen, it can be chosen from chlorine, bromine, fluorine and iodine, and that the combinations of the compounds according to the invention with the A-group streptogramins also fall within the context of the present invention.

The streptogramin compounds according to the invention have been shown to be active in vitro on *Staphylococcus aureus* 209P at concentrations ranging from 0.25 µg/ml to 32 µg/ml when combined with an A-group streptogramin compound, such as pristinamycin IIB, and at concentrations ranging from 0.5 µg/ml to 32 µg/ml on *Staphylococcus aureus* Schiclia (meticillin-resistant) combined with pristi-namycin IIB; in vivo, they synergize the antimicrobial activity of pristinamycin IIB on experimental infections of mice with *Staphylococcus aureus* IP8203 at doses ranging from 10 mg/kg to 150 mg/kg subcutaneously (CD$_{50}$), and orally at doses ranging from 24 mg/kg to 150 mg/kg (CD$_{50}$) (30/70 combinations).

The compounds according to the invention may be useful on account of their low toxicity. None of the compounds showed any toxicity at a dose of 150 mg/kg orally (2 administrations).

Among these compounds, the compounds of formula (I) wherein:
R is chosen from —NR$_1$R$_2$ and —SR$_3$, wherein:
R$_1$ and R$_2$, which may be identical or different, are
independently chosen from hydrogen and the radi-
cals:
alkyl (1 to 8 carbons), unsubstituted or substituted
with hydroxyl;
alkenyl (3 to 8 carbons);
cycloalkyl (3 to 8 carbons);
alkyloxy (1 to 8 carbons);
dialkylamino;
phenylalkyl, which is unsubstituted or substituted
with one or more substitutents chosen from halo-
gen atoms and alkyl, hydroxyalkyl, alkyloxy, and
dialkylamino radicals;
saturated and unsaturated heterocyclylalkyl radicals
(3- to 8-membered) containing one or more hetero
atoms chosen from nitrogen, sulphur, and oxygen;
and dialkylaminoalkyl;
or, alternatively,
R$_1$ and R$_2$, together with the nitrogen atom to which
they are attached, form a ring chosen from 3- to
12-membered, saturated, partially saturated and
unsaturated, monocyclic and polycyclic
heterocycles, optionally containing at least one addi-
tional hetero atom chosen from oxygen, sulphur, and
nitrogen, which heterocycle is unsubstituted or sub-
stituted with one or more radicals chosen from:
hydroxyl;
alkyl;
phenyl, which is unsubstituted or substituted with a
halogen atom;
phenylalkyl;
hydroxyalkyl;
acyl;
alkyloxycarbonyl; and
heterocyclyl and heterocyclylcarbonyl radicals,
wherein the heterocyclyl portion (4- to
6-membered) is saturated or unsaturated and con-
tains one or more hetero atoms chosen from
oxygen, sulphur, and nitrogen;
R$_3$ is chosen from alkyl radicals (1 to 8 carbons), which
are substituted with a radical —NR$_1$R$_2$ wherein:
R$_1$ and R$_2$, which may be identical or different, are
chosen from alkyl radicals, or form, together with
the nitrogen atom to which they are attached, a
heterocycle as defined above;
or, alternatively,
R$_3$ is chosen from 3- to 7-membered, saturated and
unsaturated, monocyclic and polycyclic heterocyclyl
and heterocyclylmethyl radicals, optionally contain-
ing at least one additional hetero atom chosen from
oxygen, sulphur, and nitrogen, and which are unsub-
stituted or substituted with one or more alkyl
radicals, $$\cdots\cdots\overset{5\gamma}{=}\!\!-\!\text{R'}$$

is an unsaturated ring residue which is unsubstituted
at 5γ:

or a saturated ring residue which is substituted at 5γ with a fluoro radical:

Ra is an ethyl radical, and
Rb, Rc, and Rd have the definitions below:
1) Rb and Rc are both a hydrogen atom, and Rd is chosen from methylamino and dimethylamino radicals;
2) Rb is a hydrogen atom, Rc is chosen from hydrogen and chlorine atoms, and Rd is a radical —NMe—R'″, wherein R'″ is chosen from:
   alkenyl radicals (2 to 8 carbons), heterocyclylmethyl radicals, and —COOR'e, -wherein R'e is chosen from:
      alkyl (1 to 6 carbons), alkenyl (2 to 6 carbons), phenyl, and tolyl radicals;
3) Rb is a hydrogen atom, Rd is chosen from —NHCH$_3$ and —N(CH$_3$)$_2$ radicals, and Rc is chlorine;
are included within one embodiment of the invention.

In addition, by way of example, the following compounds may be mentioned:
   5δ-(1-morpholino)methyl-5δ,5γ-dehydropristinamycin I$_E$;
   5δ-[N-methyl-N-2-(1,3-dioxolanyl)methyl]aminomethyl-5δ,5γ-dehydropristinamycin I$_E$;
   5δ-morpholinomethyl-4ζ-methylamino-4ζ-dedimethylamino-5δ,5γ-dehydropristinamycin I$_E$;
   5δ-morpholinomethyl-4ζ-methylamino-4ζ-dedimethylamino-5δ,5γ-dehydro-4ε-chloropristinamycin I$_E$; and
   5δ-[bis(2-methoxyethyl)aminomethyl]-5δ,5γ-dehydropristinamycin I$_E$.

According to one embodiment of the invention, the compounds cited in the examples are suitable, as are the following listed streptogramin compounds:
   4ε-chloro-5δ-(diethylaminoethylthiomethyl)-5δ,5γ-dehydropristinamycin I$_E$;
   5δ-(diethylaminoethylthiomethyl)-4ξ-methylamino-4ξ-dedimethylamino-5δ,5γ-dehydropristinamycin I$_E$;
   4ε-chloro-5δ-(diethylaminoethylthiomethyl)-4ξ-methylamino-4ξ-dedimethylamino-5δ,5γ-dehydropristinamycin I$_E$;
   5δ-(3-diethylaminopropylthiomethyl)-5δ,5γ-dehydropristinamycin I$_E$;
   4ε-chloro-5δ-(3-diethylaminopropylthiomethyl)-5δ,5γ-dehydropristinamycin I$_E$;
   5δ-(3-diethylaminopropylthiomethyl)-4ξ-methylamino-4ξ-dedimethylamino-5δ,5γ-dehydropristinamycin I$_E$;
   4ε-chloro-5δ-(3-diethylaminopropylthiomethyl)-4ξ-methylamino-4ξ-dedimethylamino-5δ,5γ-dehydropristinamycin I$_E$;
   5δ-(dimethylaminoethylthiomethyl)-5δ,5γ-dehydropristinamycin I$_E$;
   4ε-chloro-5δ-(dimethylaminoethylthiomethyl)-5;,5γ-dehydropristinamycin I$_E$;
   5δ-(dimethylaminoethylthiomethyl)-4ξ-methylamino-4ξ-dedimethylamino-5δ,5γ-dehydropristinamycin I$_E$;
   4ε-chloro-5δ-(dimethylaminoethylthiomethyl)-4ξ-methylamino-4ξ-dedimethylamino-5δ,5γ-dehydropristinamycin I$_E$;
   4ε-chloro-5δ-(3-piperidinopropyl)thiomethyl-4ξ-methylamino-4ξ-dedimethylamino-5δ,5γ-dehydropristinamycin I$_E$;
   4ε-chloro-5δ-(1-methyl-2-imidazolylthiomethyl)-5δ,5γ-dehydropristinamycin I$_E$;
   5δ-(1-methyl-2-imidazolylthiomethyl)-4ζ-methylamino-4ζ-dedimethylamino-5δ,5γ-dehydropristinamycin I$_E$;
   4ε-chloro-5δ-(1-methyl-2-imidazolylthiomethyl)-4ζ-methylamino-4ζ-dedimethylamino-5δ,5γ-dehydropristinamycin I$_E$;
   5δ-(morpholinoethylthiomethyl)-5δ,5γ-dehydropristinamycin I$_E$;
   4ε-chloro-5δ-(morpholinoethylthiomethyl)-5δ,5γ-dehydropristinamycin I$_E$;
   5δ-(morpholinoethylthiomethyl)-4ζ-methylamino-4ζ-dedimethylamino-5δ,5γ-dehydropristinamycin I$_E$;
   4ε-chloro-5δ-(morpholinoethylthiomethyl)-4ζ-methylamino-4ζ-dedimethylamino-5δ,5γ-dehydropristinamycin I$_E$;
   4ε-chloro-5δ-(2-piperidinoethyl)thiomethyl-5δ,5γ-dehydropristinamycin I$_E$;
   5δ-(2-piperidinoethyl)thiomethyl-4ζ-methylamino-4ζ-dedimethylamino-5δ,5γ-dehydropristinamycin I$_E$;
   4ε-chloro-5δ-(2-piperidinoethyl)thiomethyl-4ζ-methylamino-4ζ-dedimethylamino-5δ,5γ-dehydropristinamycin I$_E$;
   5δ-(3-piperidinopropyl)thiomethyl-5δ,5γ-dehydropristinamycin I$_E$;
   4ε-chloro-5δ-(3-piperidinopropyl)thiomethyl-5δ,5γ-dehydropristinamycin I$_E$;
   5δ-(3-piperidinopropyl)thiomethyl-4ζ-methylamino-4ζ-dedimethylamino-5δ,5γ-dehydropristinamycin I$_E$;
   4ε-chloro-5δ-(4-pyridylmethylthiomethyl)-5δ,5γ-dehydropristinamycin I$_E$;
   5δ-(4-pyridylmethylthiomethyl)-4ξ-methylamino-4ξ-dedimethylamino-5δ,5γ-dehydropristinamycin I$_E$;
   4ε-chloro-5δ-(4-pyridylmethylthiomethyl)-4ξ-methylamino-4ξ-dedimethylamino-5δ,5γ-dehydropristinamycin I$_E$;
   4ε-chloro-5δ-(3-pyridylmethylthiomethyl)-5δ,5γ-dehydropristinamycin I$_E$;
   5δ-(3-pyridylmethylthiomethyl)-4ξ-methylamino-4ξ-dedimethylamino-5δ,5γ-dehydropristinamycin I$_E$;
   4ε-chloro-5δ-(3-pyridylmethylthiomethyl)-4ξ-methylamino-4ξ-dedimethylamino-5δ,5γ-dehydropristinamycin I$_E$;
   5δ-(2-pyridylmethylthiomethyl)-5δ,5γ-dehydropristinamycin I$_E$;
   4ε-chloro-5δ-(2-pyridylmethylthiomethyl)-5δ,5γ-dehydropristinamycin I$_E$;
   5δ-(2-pyridylmethylthiomethyl)-4ξ-methylamino-4ξ-dedimethylamino-5δ,5γ-dehydropristinamycin I$_E$;
   4ε-chloro-5δ-(2-pyridylmethylthiomethyl)-4ξ-methylamino-4ξ-dedimethylamino-5δ,5γ-dehydropristinamycin I$_E$;
   5δ-{[2-(4-methylpiperazin-1-yl)ethyl]thiomethyl}-5δ,5γ-dehydropristinamycin I$_E$;
   4ε-chloro-5δ-{[2-(4-methylpiperazin-1-yl)ethyl]thiomethyl}-5δ,5γ-dehydropristinamycin I$_E$;
   5δ-{[2-(4-methylpiperazin-1-yl)ethyl]thiomethyl}-4ζ-methylamino-4ζ-dedimethylamino-5δ,5γ-dehydropristinamycin I$_E$;

4ε-chloro-5δ-{[2-(4-methylpiperazin-1-yl)ethyl]thiomethyl}-4ζ-methylamino-4ζ-dedimethylamino-5δ,5γ-dehydropristinamycin $I_E$;

5δ-(butoxycarbonylaminoethylthiomethyl)-5δ,5γ-dehydropristinamycin $I_E$;

4ε-chloro-5δ-(butoxycarbonylaminoethylthiomethyl)-5δ,5γ-dehydropristinamycin $I_E$;

5δ-(butoxycarbonylaminomethylthioethyl)-4ζ-methylamino-4ζ-dedimethylamino-5δ,5γ-dehydropristinamycin $I_E$;

4ε-chloro-5δ-(butoxycarbonylaminoethylthiomethyl)-4ζ-methylamino-4ζ-dedimethylamino-5δ,5γ-dehydropristinamycin $I_E$;

5δ-(aminoethylthiomethyl)-5δ,5γ-dehydropristinamycin $I_E$;

4ε-chloro-5δ-(aminoethylthiomethyl)-5δ,5γ-dehydropristinamycin $I_E$;

5δ-(aminomethylthioethyl)-4ζ-methyamino-4ζ-dedimethylamino-5δ,5γ-dehydropristinamycin $I_E$;

4ε-(chloro-5δ-(aminoethylthiomethyl)-4ζ-methylamino-4ζ-dedimethylamino-5δ,5γ-dehydropristinamycin $I_E$;

5δ-(pyrrolidinoethylthiomethyl)-5δ,5γ-dehydropristinamycin $I_E$;

4ε-chloro-5δ-(pyrrolidinoethylthiomethyl)-5δ,5γ-dehydropristinamycin $I_E$;

5δ-(pyrrolidinoethylthiomethyl)-4ζ-methylamino-4ζ-dedimethylamino-5δ,5γ-dehydropristinamycin $I_E$;

4ε-chloro-5δ-(pyrrolidinoethylthiomethyl)-4ζ-methylamino-4ζ-dedimethylamino-5δ,5γ-dehydropristinamycin $I_E$;

5δ-(diisopropylaminoethylthiomethyl)-5δ,5γ-dehydropristinamycin $I_E$;

4ε-chloro-5δ-(diisopropylaminoethylthiomethyl)-5δ,5γ-dehydropristinamycin $I_E$;

5δ-(diisopropylaminoethylthiomethyl)-4ζ-methylamino-4ζ-dedimethylamino-5δ,5γ-dehydropristinamycin $I_E$;

4ε-chloro-5δ-(diisopropylaminoethylthiomethyl)-4ζ-methylamino-4ζ-dedimethylamino-5δ,5γ-dehydropristinamycin $I_E$;

5δ-(N-ethyl-N-methylaminoethylthiomethyl)-5δ,5γ-dehydropristinamycin $I_E$;

4ε-chloro-5δ-(N-ethyl-N-methylaminoethylthiomethyl)-5δ,5γ-dehydropristinamycin $I_E$;

5δ-(N-ethyl-N-methylaminoethylthiomethyl)-4ζ-methylamino-4ζ-dedimethylamino-5δ,5γ-dehydropristinamycin $I_E$;

4ε-chloro-5δ-(N-ethyl-N-methylaminoethylthiomethyl)-4ζ-methylamino-4ζ-dedimethylamino-5δ,5γ-dehydropristinamycin $I_E$;

5δ-((2R)-3-diethylaminopropyl-2-thiomethyl)-5δ,5γ-dehydropristinamycin $I_E$;

4ε-chloro-5δ-((2R)-3-diethylaminopropyl-2-thiomethyl)-5δ,5γ-dehydropristinamycin $I_E$;

5δ-((2R)-3-diethylaminopropyl-2-thiomethyl)-4ζ-methylamino-4ζ-dedimethylamino-5δ,5γ-dehydropristinamycin $I_E$;

4ε-chloro-5δ-((2R)-3-diethylaminopropyl-2-thiomethyl)-4ζ-methylamino-4ζ-dedimethylamino-5δ,5γ-dehydropristinamycin $I_E$;

5δ-((2S)-3-diethylaminopropyl-2-thiomethyl)-5δ,5γ-dehydropristinamycin $I_E$;

4ε-chloro-5δ-((2S)-3-diethylaminopropyl-2-thiomethyl)-5δ,5γ-dehydropristinamycin $I_E$;

5δ-((2S)-3-diethylaminopropyl-2-thiomethyl-4ζ-methylamino-4ζ-dedimethylamino-5δ,5γ-dehydropristinamycin $I_E$; and 4ε-chloro-5δ-((2S)-3-diethylaminopropyl-2-thiomethyl)-4ζ-methylamino-4ζ-dedimethylamino-5δ,5γ-dehydropristinamycin $I_E$.

The streptogramin compounds of formula (α) are described, along with their preparation, in international patent application WO 99/05165, the disclosure of which is incorporated herein by reference.

The streptogramin compounds of formula (β), described in French patent application FR 99/08375, the disclosure of which is incorporated herein by reference, are prepared by halogenation, by conversion into an azide or by conversion into a thiocyanate, of a streptogramin compound of formula (γ):

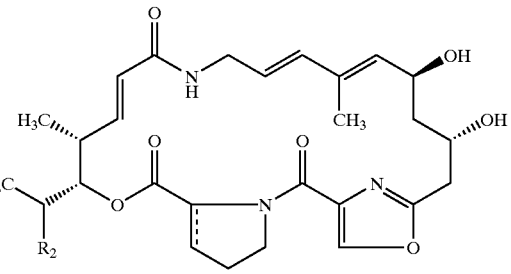

(γ)

wherein $R_2$ is defined as above, the - - - bond represents a single bond (27R stereochemistry) or a double bond, and wherein the hydroxyl function in position 14 has been protected beforehand, followed by removal of the protecting radical and, where appropriate, in order to obtain a compound or formula (β) wherein $R_3$ is other than a hydrogen atom, by introduction of the aliphatic, cycloaliphatic, aromatic, araliphatic, heterocyclic, or heterocyclylaliphatic ester residue which may be substituted ($R_3$) according to the usual methods which do not adversely affect the rest of the molecule.

The halogenation reactions, conversion into an azide, or conversion into a thiocyanate can be performed in the presence of an aminosulphur trifluoride such as, for example, diethylaminosulphur trifluoride, bis(2-methoxyethyl)aminosulphur trifluoride (Deoxofluor®), or morpholinosulphur trifluoride, or, alternatively, in the presence of sodium tetrafluoride, using a reagent such as a tetraalkylammonium, for example, tetramethylammonium, tetraethylammonium, tetrapropylammonium, or tetrabutylammonium, trialkylbenzylammonium or trialkylphenylammonium halide, azide, or thiocyanate, or using an alkali metal halide, azide or thiocyanate optionally supplemented with crown ether. The reaction is performed in a chlorinated organic solvent such as, for example, dichloromethane, dichloroethane, or chloroform, or in an ether such as tetrahydrofuran, at a temperature ranging from −78° C. to 40° C., optionally under argon or nitrogen. The use of the hydroxyl compound of (16S) configuration gives the compound of (16R) configuration. The protection and deprotection of the hydroxyl radical in position 14 is performed according to the usual methods which do not adversely affect the rest of the molecule (T. W. Greene and P. G. M. Wuts, *Protective Groups in Organic Synthesis* (2nd edition), Wiley—Interscience (1991), the disclosure of which is incorporated herein by reference).

In order to prepare a compound of formula (β) wherein $R_3$ is an aliphatic, cycloaliphatic, aromatic, araliphatic, heterocyclic, or heterocyclylaliphatic ester which may be substituted, the esterification is performed by reacting the acid or a reactive derivative of the acid such as, for example, acid chloride, reactive ester, or anhydride, in the presence or absence of a coupling agent such as, for example, a carbodiimide, for example, dicyclohexylcarbodiimide, and a tertiary amine such as, for example, a trialkylamine, for example triethylamine, diisopropylethylamine, pyridine, or a derivative of any of the foregoing, and optionally a catalyst such as 4-N-dimethylaminopyridine, at a temperature ranging from 40° C. to +80° C., in an organic solvent such as an amide, for example, dimethylformamide or N-methyl-2-pyrrolidinone, pyridine, a halogenated solvent, for example, dichloromethane, dichloroethane, or chloroform, or an ether, such as tetrahydrofuran, dioxane, or dimethoxyethane. The functions which may interfere with the reaction are protected beforehand.

The following nonlimiting examples illustrate the present invention.

In the examples which follow, the NMR spectra were acquired in deuterochloroform, the nomenclature used is that of J. O. Anteunis et al., *Eur. Biochem.*, 58, 259 (1975), the disclosure of which is incorporated herein by reference.

The column chromatographies were performed, except where otherwise mentioned, under atmospheric pressure using a 0.063–0.02 mm silica. In a few specific cases, the purifications were performed by flash chromatography using a 0.04–0.063 mm silica, or by high performance liquid chromatography (HPLC) on $C_8$ or $C_{18}$ grafted silica. As the chromatography proceeded, the fractions were analysed by thin layer chromatography (TLC) on Merck 60F254 silica plates, or by analytical HPLC. The fractions corresponding to the same Rf or to the same retention time were combined and then concentrated to dryness, under reduced pressure (30–45° C.; 2.7 kPa). The products thus obtained were analysed by the usual spectroscopic techniques (NMR; IR; MS), which allowed the expected products to be identified.

EXAMPLE 1

60 g of a crude mixture containing 33 mol % of 5δ-chloromethyl-5δ,5γ-dehydropristinamycin $I_E$, prepared under the conditions described below, were introduced into a three-necked flask containing 500 cm³ of acetonitrile, followed by addition of 18 cm³ of morpholine. The mixture was refluxed for 5 hours and was then concentrated to dryness at 45° C. under reduced pressure (2.7 kPa) to give 68.8 g of a solid which was taken up in 200 cm³ of saturated aqueous sodium bicarbonate solution and 200 cm³ of dichloromethane. The organic phase was separated out after settling had taken place and then dried over sodium sulphate, filtered and concentrated to dryness at 45° C. (2.7 kPa) to give 56.4 g of a yellow solid, to which was added 300 cm³ of water and 140 cm³ of 1N hydrochloric acid. The aqueous phase obtained was successively extracted with 4 times 100 cm³ of ethyl acetate and 100 cm³ of dichloromethane and was then brought to pH 7–8 by addition of 12 g of sodium bicarbonate and extracted with 400 cm³ of dichloromethane. The organic phase was separated out after settling had taken place, dried over sodium sulphate, filtered and then concentrated to dryness to give 41.3 g of a yellow solid which was purified by chromatography on 200 g of silica (eluent: 98/2 dichloromethane/methanol by volume). A solid was thus obtained which was crystallized from a methanol/water mixture (90/10 by volume). A second crystallization of 5.05 g of the solid thus crystallized from 20 cm³ of methanol gave, after filtration and drying at 45° C. (90 Pa), 4.5 g of 5δ(1-morpholino)methyl-5δ,5γ-dehydropristinamycin $I_E$, in the form of a whitish powder melting at 180° C.

$^1$H NMR spectrum (400 MHz, CDCl$_3$): 0.92 (t, J=7.5 Hz, 3H: CH$_3$ at 2γ); 1.08 (very broad d, J=16.5 Hz, 1H: 1H of the CH$_2$ at 5β); 1.27 (mt, 2H: 1H of the CH$_2$ at 3β and 1H of the CH$_2$ at 3γ); 1.30 (d, J=7 Hz, 3H: CH$_3$ at 1γ); 1.57 (mt, 1H: the other H of the CH$_2$ at 3γ); 1.66 and 1.72 (2 mts, 1H each: CH$_2$ at 2β); 2.00 (mt, 1H: the other H of the CH$_2$ at 3β); 2.36 (unres. mult., 4H: NCH$_2$ of the morpholine); 2.47 (broad dd, J=16.5 and 5 Hz, 1H: the other H of the CH$_2$ at 5β); 2.85 (s, 2H: CH$_2$N); 2.94 (s, 6H: ArN(CH$_3$)$_2$); 2.99 (dd, J=14 and 6.5 Hz, 1H: 1H of the CH$_2$ at 4β); 3.17 (mt, 1H: the other H of the CH$_2$ at 4β); 3.17 (s, 3H: NCH$_3$); 3.27 (mt, 1H: 1H of the CH$_2$ at 3δ); 3.34 (broad d, J=18 Hz, 1H: 1H of the CH$_2$ at 5ε); 3.47 (mt, 1H: the other H of the CH$_2$ at 3δ); 3.70 (mt, 4H; CH$_2$O of the morpholine); 4.57 (dd, J=8 and 5 Hz, 1H: CH at 3α); 4.78 (mt, 1H: CH at 2α); 4.82 (broad d, J=18 Hz, 1H: the other H of the CH$_2$ at 5ε); 4.89 (dd, J=10 and 1 Hz, 1H: CH at 1α); 5.11 (d, J=5 Hz, 1H: CH at 5α); 5.27 (dd, J=9 and 6.5 Hz, 1H: CH at 4α); from 5.50 to 5.55 (mt, 1H: CH at 5γ); 5.52 (d, J=8 Hz, 1H: CH at 6α); 5.87 (resolved q, J=7 and 1 Hz, 1H: CH at 1β); 6.58 (d, J=8 Hz, 2H: aromatic Hs at 4ε); 6.65 (d, J=9.5 Hz, 1H: CONH at 2); 6.92 (d, J=8 Hz, 2H: aromatic Hs at 4δ); from 7.20 to 7.45 (mt: the 7 Hs corresponding to the aromatic Hs at 6α- to H$_4$ and to H$_5$); 7.76 (dd, J=4 and 1 Hz, 1H: H$_6$); 8.47 (d, J=10 Hz, 1H: CONH at 1); 8.51 (d, J=8 Hz, 1H: CONH at 6); 11.69 (s, 1H: OH).

5δ-Chloromethyl-5δ,5γ-dehydropristinamycin $I_E$ was obtained in the following way:

5.9 g of (5γR,5γS)-5γ-hydroxy-5γ-deoxy-5δ-methylenepristinamycin $I_A$ (50/50 mixture of the two isomers) were introduced into a three-necked flask containing 100 cm³ of tetrahydrofuran, followed by 1 cm³ of thionyl chloride. The mixture was stirred overnight at 20° C. and then filtered. The filtrate was concentrated to dryness at 45° C. under reduced pressure to give a solid which was taken up in 100 cm³ of saturated aqueous sodium bicarbonate solution and 100 cm³ of dichloromethane. The organic phase was separated out after settling had taken place, dried over sodium sulphate, filtered and concentrated to dryness. 1.45 g of a crude product were thus obtained, which product was purified by two successive chromatographies on silica (eluent: 98/2 dichloromethane/methanol by volume) to give 1.24 g of a crude mixture containing 50 mol % of 5δ-chloromethyl-5δ,5γ-dehydropristinamycin $I_E$ in the form of a yellow solid.

(5γR)- and (5γS)-5γ-hydroxy-5γ-deoxy-5δ-methylenepristinamycin $I_A$ was obtained in the following way:

10 g of 5δ-methylenepristinamycin $I_A$ and 2.8 g of anhydrous cerium chloride were introduced into a three-necked flask containing 100 cm³ of methanol and 50 cm³ of dichloromethane. 0.47 g of sodium borohydride was added portionwise to this mixture, cooled to 0° C. The reaction mixture was then stirred for 3 hours, followed by dilution with 100 cm³ of water. The pH of the aqueous phase was adjusted to 5 by addition of acetic acid. The resulting mixture was then concentrated under reduced pressure. The residual aqueous phase was brought to pH 7 by addition of saturated aqueous sodium bicarbonate solution and was then extracted with twice 50 cm³ of dichloromethane. The organic phases were combined and then dried over sodium sulphate, filtered and then concentrated to dryness at 45° C. under reduced pressure (2.7 kPa) to give 7.6 g of a solid, 2 g of which were purified by three successive preparative high performance liquid chromatographies (HPLCs) on 450 g of 10 μm C$_8$ silica (eluent: 70/30 water/acetonitrile by volume, containing 0.1% trifluoroacetic acid). The fractions containing the expected 5γS isomer were combined, the acetonitrile was removed at 40° C. under reduced pressure (2.7 kPa) and the pH of the aqueous phase was adjusted to 7 by addition of saturated aqueous sodium bicarbonate solution. The precipitate formed was filtered off and then stirred in 20 cm$^3$ of diethyl ether. The resulting solid was filtered off and dried at 40° C. under reduced pressure (90 Pa) to give 0.19 g of (5γS)-5γ-hydroxy-5γ-deoxy-5δ-methylenepristinamycin I$_A$ in the form of a white solid melting at 166° C. Working in the same way for the fractions containing the 5γR isomer, 0.18 g of (5γ-R)-5γ-hydroxy-5γ-deoxy-5δ-methylenepristinamycin I$_A$ was obtained in the form of a white solid melting at 246° C.

(5γS)-5γ-Hydroxy-5γ-deoxy-5δ-methylenepristinamycin I$_A$:
$^1$H NMR spectrum (400 MHz, CDCl$_3$); 0.47 (dt, J=15 and 5.5 Hz, 1H: 1H of the CH$_2$ at 5β); 0.92 (t, J=7.5 Hz, 3H: CH$_3$ at 2γ); 1.10 (mt, 1H: 1H of the CH$_2$ at 3β); from 1.25 to 1.40 (mt, 1H: 1H of the CH$_2$ at 3γ); 1.35 (d, J=7 Hz, 3H: CH$_3$ at 1γ); from 1.55 to 1.80 (mt: the 3 Hs corresponding to the other H of the CH$_2$ at 3γ and to the CH$_2$ at 2β); 1.99 (mt, 1H: the other H of the CH$_2$ at 3β); 2.13 (broad d, J=15 Hz, 1H: the other H of the CH$_2$ at 5β); 2.90 (dd, J=13 and 5 Hz, 1H: 1H of the CH$_2$ at 4, ); 2.98 (s, 6H: ArN(CH$_3$)$_2$); from 3.15 to 3.35 (mt, 2H: the other H of the CH$_2$ at 4β and 1H of the CH$_2$ at 3δ); 3.20 (s, 3H: NCH$_3$); 3.38 (d, J=14.5 Hz, 1H: 1H of the CH$_2$ at 5ε); 3.52 (mt, 1H: the other H of the CH$_2$ at 3δ); 3.90 (mt, 1H: CH at 5γ); 4.53 (t, J=7.5 Hz, 1H: CH at 3α); 4.81 (mt, 1H: CH at 2α); 4.88 (d, J=14.5 Hz, 1H: the other H of the CH$_2$ at 5ε); 4.91 (broad d, J=10 Hz 1H: CH at 1α); 5.03 (broad d, J=5.5 Hz, 1H: CH at 5α); 4.95 and 5.00 (2 broad s, 1H each: =CH$_2$); 5.17 (dd, J=11 and 5 Hz, 1H: CH at 4α); 5.70 (d, J=8 Hz, 1H: OH at 5γ); 5.77 (d, J=8.5 Hz, 1H: CH at 6α); 5.92 (broad q, J=7 Hz, 1H: CH at 1β); 6.54 (d, J=9.5 Hz, 1H: CONH at 2); 6.60 (d, J=8 Hz, 2H: aromatic Hs at 4ε); 6.92 (d, J=8 Hz, 2H: aromatic Hs at 4δ); from 7.20 to 7.35 (mt: the 5 Hs corresponding to the aromatic Hs at 6α); 7.38 (limiting AB, 2H: H$_4$ and H$_5$); 7.78 (mt, 1H: H$_6$); 8.44 (d, J=10 Hz, 1H: CONH at 1); 9.10 (d, J=8.5 Hz: CONH at 6); 11.66 (s, 1H: OH).

(5γR)-5γ-Hydroxy-5γ-deoxy-5δ-methylenepristinamycin I$_A$:
$^1$H NMR spectrum (400 MHz, CDCl$_3$); 0.17 (resolved t, J=12 and 5.5 Hz, 1H: 1H of the CH$_2$ at 5β); 0.91 (t, J=7.5 Hz, 3H: CH$_3$ at 2γ); 1.18 (mt, 1H: 1H of the CH$_2$ at 3β); 1.28 (mt, 1H: 1H of the CH$_2$ at 3γ); 1.34 (d, J=7 Hz, 3H: CH$_3$ at 1γ); 1.57 (mt: 1H: the other H of the CH$_2$ at 3γ); from 1.60 to 1.80 (mt, 2 Hs corresponding to the CH$_2$ at 3γ); from 1.60 to 1.80 (mt: 2 Hs corresponding to the CH$_2$ at 2β); 1.99 (mt, 1H: the other H of the CH$_2$ at 3β); 2.39 (dd, J=12 and 6 Hz, 1H: the other H of the CH$_2$ at 5β); 2.90 to 3.00 (mt, 1H: 1H of the CH$_2$ at 4β); 2.96 (s, 6H: ArN(CH$_3$)$_2$); 3.06 (d, J=14 Hz, 1H: 1H of the CH$_2$ at 5ε); 3.17 (s, 3H: NCH$_3$); 3.20 (dd, J=13.5 and 10 Hz, 1H: the other H of the CH$_2$ at 4β); 3.28 and 3.49 (2 mts, 1H each: CH$_2$ at 3δ); 4.55 (dd, J=8 and 7 Hz, 1H: CH at 3α); 4.70 (mt, 1H: CH at 5γ); 4.79 (mt, 1H: CH at 2α); 4.87 (broad d, J=10 Hz, 1H: CH at 1α); from 5.00 to 5.15 (mt, 3H: CH at 5α- the other H of the CH$_2$ at 5ε and 1H of the =CH$_2$); 5.17 (broad s, 1H: the other H of the =CH$_2$); 5.21 (dd, J=10 and 6.5 Hz, 1H: CH at 4α); 5.65 (d, J=8.5 Hz, 1H: CH at 6α); 5.90 (mt, 1H: CH at 1β); 6.56 (d, J=10 Hz, 1H: CONH at 2); 6.59 (d, J=8 Hz, 2H: aromatic Hs at 4ε); 6.91 (d, J=8 Hz, 2H: aromatic Hs at 4δ); from 7.20 to 7.45 (mt: the 7 Hs corresponding to the aromatic Hs at 6α- to H$_4$ and to H$_5$); 7.76 (broad d, J=4 Hz, 1H: H$_6$); 8.41 (d, J=10 Hz, 1H: CONH at 1); 8.61 (d, J=8.5 Hz: CONH at 6); 11.66 (s, 1H: OH).

EXAMPLE 2

21.2 g of 5δ-(1-morpholino)methyl-5γ-deoxy-5γ-hydroxypristinamycin I$_A$ (mixture of the 5δ and 5γ isomers) were introduced into a three-necked flask containing 350 cm$^3$ of dichloromethane. 14.3 cm$^3$ of diethylaminosulphur trifluoride were added to the mixture, cooled to 0° C. After addition, the reaction mixture was stirred at 20° C. for 18 hours and then poured into 400 cm$^3$ of water. The pH of the aqueous phase was brought to 7 by addition of saturated aqueous sodium bicarbonate solution. The organic phase was separated out after settling had taken place, washed with 200 cm$^3$ of water, dried over sodium sulphate, filtered, concentrated to dryness, and taken up in 200 cm$^3$ of ethyl acetate. The insoluble material formed was filtered off and the filtrate was concentrated to dryness at 45° C. under reduced pressure (2.7 kPa). 10.6 g of a crude product were obtained, which product was purified by chromatography on 250 g of silica (eluent: 97.5/2.5 dichloromethane/methanol by volume) to give 4.5 g of a solid which was purified in two batches (1.5 g and 3 g) by two successive preparative HPLCs on 450 g of 10 μm C$_8$ silica (eluent: 70/30 water/acetonitrile by volume, containing 0.1% trifluoroacetic acid). The fractions, 4 to 8 and 3 to 5 respectively, were combined, the acetonitrile was removed at 40° C. under reduced pressure (2.7 kPa), and the pH of the residual aqueous phase was adjusted to 7 by addition of saturated aqueous sodium bicarbonate solution. The precipitate formed was filtered off, rinsed with 20 cm$^3$ of water and 20 cm$^3$ of diisopropyl ether, and then dried at 40° C. under reduced pressure (90 Pa) to give 0.35 g (1.7%) of 5δ-(1-morpholino)methyl-5δ,5γ-dehydropristinamycin I$_E$.

$^1$H NMR spectrum (400 MHz, CDCl$_3$); 0.92 (t, J=7.5 Hz, 3H: CH$_3$ at 2γ); 1.08 (very broad d, J=16.5 Hz, 1H: 1H of the CH$_2$ at 5β); 1.27 (mt, 2H of the CH$_2$ at 3β and 1H of the CH$_2$ at 3γ); 1.30 (d, J=7 Hz, 3H: CH$_3$ at 1γ); 1.57 (mt: 1H: the other H of the CH$_2$ at 3γ); 1.66 and 1.72 (2 mts, 1H each: CH$_2$ at 2β); 2.00 (mt, 1H: the other H of the CH$_2$ at 3β); 2.36 (unres. mult., 4H: NCH$_2$ of the morpholine); 2.47 (broad dd, J=16.5 and 5 Hz, 1H: the other H of the CH$_2$ at 5β); 2.85 (s, 6H: CH$_2$N); 2.94 (s, 6H ArN(CH$_3$)$_2$); 2.99 (dd, J=14 and 6.5 Hz, 1H: 1H of the CH$_2$ at 4β); 3.17 (mt, 1H: the other H of the CH$_2$ at 4β); 3.17 (s, 3H: NCH$_3$); 3.27 (mt, 1H: 1H of the CH2 at 3δ); 3.34 (broad d, J=18 Hz, 1H: 1H of the CH$_2$ at 5ε); 3.47 (mt, 1H: the other H of the CH$_2$ at 3δ); 3.70 (mt, 4H: CH$_2$O of the morpholine); 4.57 (dd, J=8 and 5 Hz, 1H: CH at 3α); 4.78 (mt, 1H: CH at 2α); 4.82 (broad d, J=18 Hz, 1H: the other H of the CH$_2$ at 5ε); 4.89 (dd, J=10 and 1 Hz, 1H: CH at 1α); 5.11 (d, J=5 Hz, 1H: CH at 5α); 5.27 (dd, J=9 and 6.5 Hz, 1H: CH at 4α); from 5.50 to 5.55 (mt, 1H: CH at 5γ); 5.52 (d, J=8 Hz, 1H: CH at 6α); 5.87 (resolved q, J=7 and 1 Hz, 1H: CH at 1β); 6.58 (d, J=8 Hz, 2H: aromatic Hs at 4ε); 6.65 (d, J=9.5 Hz, 1tH: CONH at 2); 6.92 (d, J=8 Hz, 2H: aromatic Hs at 4δ); from 7.20 to 7.45 (mt: the 7 Hs corresponding to the aromatic Hs at 6α- to H$_4$ and to H$_5$); 7.76 (dd, J=4 and 1 Hz, 1H: H$_6$); 8.47 (d, =10 Hz, 1H: CONH at 1); 8.51 (d, J=8 Hz, 1H: CONH at 6); 11.69 (s, 1H: OH).

5δ-(1-Morpholino)methyl-5γ-deoxy-5γ-hydroxypristinamycin I$_A$ (mixture of the 5δ and 5γ isomers) was obtained in the following way:

11 g of 5δ-(1-morpholino)methylpristinamycin I$_A$ (90/10 mixture of the 5δS and 5δR isomers) were placed in 120 cm$^3$ of 1,2-dimethoxyethane in a round-bottomed flask, followed by addition of 0.42 g of sodium borohydride. After stirring overnight at 20° C., 60 cm³ of isopropanol and a further 0.42 g of sodium borohydride were added and stirring was then continued for 5 hours. The reaction mixture was concentrated to dryness under reduced pressure, diluted with 40 cm³ of dichloromethane and 400 cm³ of distilled water, and 1N hydrochloric acid was added so as to adjust the pH to 3. The aqueous phase was separated out after settling had taken place and was then washed with 3 times 30 cm³ of dichloromethane. The organic phases were combined, dried over sodium sulphate, filtered, and concentrated to dryness under reduced pressure to give 10.84 g of a solid which was purified by flash chromatography (eluent gradient: 98/2 to 96/4 $CH_2Cl_2$/MeOH by volume) to give 1.6 g of a product which was stirred in 50 cm³ of diethyl ether. After filtration and drying at 50° C. under reduced pressure (90 Pa), 1.14 g of 5δ-(1-morpholino)methyl-5γ-deoxy-5γ-hydroxypristinamycin $I_A$ (90/10 mixture of the 5δ isomers and 50/50 mixture of the 5γ isomers) were obtained in the form of a white solid melting at about 180° C. (not sharp).

$^1$H NMR spectrum (400 MHz, $CDCl_3$, δ in ppm); 0.42 (dt, J=15 and 5 Hz, 1H: 1H of the $CH_2$ at 5b); 0.89 (t, J=7.5 Hz, 3H: $CH_3$ at 2g); 1.02 (mt, 1H: 1H of the $CH_2$ at 3b); from 1.1 5 to 1.35 (mt, 1H: 1H of the $CH_2$ at 3d); 1.33 (d, J=7 Hz, 3H: $CH_3$ at 1g); from 1.45 to 1.80 (mt: the 4 Hs corresponding to the CH at 5d- to the other H of the $CH_2$ at 3g and to the $CH_2$ at 2b); 1.97 (mt, 1H: the other H of the $CH_2$ at 3b); 2.13 (broad d, J=15 Hz, 1H: the other H of the $CH_2$ at 5b); 2.27 (dd, J=12 at 6 Hz, 1H: 1H of the $CH_2$N); from 2.30 to 2.50 (mt, 4H: the other H of the $CH_2$-1H of the 2 $NCH_2$s of the morpholine and 1H of the $CH_2$ at 5e); from 2.45 to 2.60 (mt, 2H: the other H of the 2 $NCH_2$s of the morpholine); from 2.80 to 3.00 (mt, 1H: 1H of the $CH_2$ at 4b); 2.96 (s, 6H: $ArN(CH_3)_2$); from 3.10 to 3.30 (mt, 2H: 1H of the $CH_2$ at 3d and the other H of the $CH_2$ at 4b); 3.21 (s, 3H: $NCH_3$); from 3.40 to 3.60 (mt, 2H: the other 1H of the $CH_2$ at 3d and CH at 5g); 3.76 (mt, 4H: the 2 $OCH_2$s of the morpholine); 4.46 (broad d, J=13 Hz, 1H: the other H of the $CH_2$ at 5e); 4.50 (t, J=8 Hz, 1H: CH at 3a); 4.81 (mt, 1H: CH at 2a); 4.90 (dd, J=10 and 1 Hz, 1H: CH at 1a); 5.04 (broad d, J=5 Hz, 1H: CH at 5a); from 5.25 to 5.35 (mt, 2H: OH at 5g and CH at 4a); 5.80 (d, J=9 Hz, 1H: CH at 6a); 5.98 (resolved q, J=7 and 1 Hz, 1H; CH at 1b); 6.56 (d, J=10 Hz, 1H: CONH at 2); 6.59 (d, J=8.5 Hz, 2H: aromatic Hs at 4ε); 6.99 (d, J=8.5 Hz, 2H: aromatic Hs at 4d); from 7.15 to 7.35 (mt. 5 aromatic Hs at 6); 7.40 (limiting AB, 2H: $H_4$ and $H_5$); 7.86 (dd, J=4 and 2 Hz, 1H: $H_6$); 8.48 (d, J=10 Hz, 1H: CONH at 1); 9.15 (d, J=9 Hz, 1H: CONH at 6); 11.66 (s, 1H: OH).

5δ-(1-Morpholino)methylpristinamycin $I_A$ (90/1 0 mixture of the 5δR and 5δS isomers) can be obtained by the following method: 4g of 5δ-methylenepristinamycin $I_A$ dissolved in a mixture of 10 cm³ of dichloromethane and 50 cm³ of methanol were placed in a round-bottomed flask maintained under a nitrogen atmosphere, followed by addition of 1.8 cm³ of morpholine. The mixture was left stirring for 4 days, concentrated to dryness under reduced pressure at 30° C., and then stirred in 40 cm³ of diethyl ether. The supernatant was removed and the resulting solid was then stirred in 40 cm³ of diethyl ether, filtered, and then dried under reduced pressure (2.7 kPa) to give 3.54 g of 5δ-(1-morpholino)-methylpristinamycin $I_A$ (90/10 mixture of the 5δR and 5δS isomers) in the form of a whitish solid containing one mole of morpholine per mole of product. This solid was used without further purification.

$^1$H NMR spectrum (400 MHz, $CDCl_3$, δ in ppm); 0.68 (dd, J=15 and 5.5 Hz, 1H: 1H of the $CH_2$ at 5b); 0.91 (t, J=7.5 Hz, 3H: $CH_3$ at 2g); 1.12 (mt, 1H: 1H of the $CH_2$ at 3b); from 1.15 to 1.35 (mt, 1H: 1H of the $CH_2$ at 3g); 1.32 (d, J=7 Hz, 3H: $CH_3$ at 1g); from 1.45 to 1.70 (mt, 2H: the other H of the $CH_2$ at 3g and 1H of the $CH_2$ at 2b); 1.75 (mt, 1H: the other H of the $CH_2$ at 2b); 2.01 (mt, 1H: the other H of the $CH_2$ at 3b); from 2.20 to 2.45 (mt, 5H: CH at 5d- the other H of the $CH_2$ at 5b- 1H of the $NCH_2$ and 1H of the 2 $NCH_2$s of the morpholine); from 2.40 to 2.60 (mt, 3H: 1H of the $CH_2$ at 5e and the other H of the 2 $NCH_2$s of the morpholine); 2.79 (dd, J=12.5 and 4 Hz, 1H: the other H of the $NCH_2$); from 2.80 to 2.95 (mt, 1H: 1H of the $CH_2$ at 4b); 2.92 (s, 6H: $ArN(CH_3)_2$); from 3.15 to 3.25 (mt, 1H: 1H of the $CH_2$ at 3d); 3.25 (s, 3H: $NCH_3$); 3.32 (t, J=12 Hz, 1H: the other H of the $CH_2$ at 4b); 3.53 (mt, 1H: the other H of the $CH_2$ at 3d); 3.72 (mt: the 4 Hs corresponding to the 2 $CH_2$Os of the morpholine); 4.54 (t, J=8 Hz, 1H: CH at 3a); 4.82 (mt, 1H: CH at 2a); 4.87 (dd, J=10 and 1 Hz, 1H: CH at 1a); 4.95 (broad dd, J=13 and 6 Hz, 1H: the other H of the $CH_2$ at 5e); 5.25 (dd, J=12 and 4 Hz, 1H: CH at 4a); (broad d, J=5.5 Hz, 1H: CH at 5a); 5.85 (d, J=9.5 Hz, 1H: CH at 6a); 5.89 (mt, 1H: CH at 1b); 6.49 (d, J=10 Hz, 1H: CONH at 2); 6.61 (d, J=8 Hz, 2H: aromatic Hs at 4ε); 7.04 (d, J=8 Hz, 2H: aromatic Hs at 4d); from 7.10 to 7.35 (mt: the 5 aromatic Hs at 6); 7.44 (limiting AB, 2H: $H_4$ and $H_5$); 7.83 (dd, J=4 and 1.5 Hz, 1H: $H_6$) 8.40 (d, J=10 Hz, 1H: CONH at 1); 8.75 (d, J=9.5 Hz, 1H: CONH at 6).

EXAMPLE 3

The fractions 10 to 14 and 7 to 13, respectively, from the chromatography in Example 2, were treated under the same conditions as in Example 2 to give 0.37 g (1.8%) of (5δR, 5γS)-5γ-deoxy-5γ-fluoro-5δ-(1-morpholino) methylpristinamycin $I_A$, in the form of a white solid melting at 162–164° C.

$^1$H NMR spectrum (400 MHz, $CDCl_3$): 0.29 (mt, 1H: 1H of the $CH_2$ at 5β); 0.90 (t, J=7.5 Hz, 3H: $CH_3$ at 2γ); 1.10 (mt, 1H: 1H of the $CH_2$ at 3β); 1.26 (mt, 1H: 1H of the $CH_2$ at 3γ); 1.33 (d, J=7 Hz, 3H: $CH_3$ at 1γ); 1.55 (mt, 1H; the other H of the $CH_2$ at 3γ); 1.65 (mt, 1H: 1H of the $CH_2$ at 2β); 1.75 (mt, 2H: CH at 5δ and the other H of the $CH_2$ at 2β); 1.98 (mt, 1H: the other H of the $CH_2$ at 3β); 2.05 (t, J=13.5 Hz, 1H: 1H of the $CH_2$ at 5ε); 2.22 (broad t, J=11.5 Hz, 1H: 1H of the $CH_2$N); from 2.30 to 2.45 (mt, 3H: the other H of the $CH_2$ at 5β and 2H of the 2 $CH_2$Ns of the morpholine); from 2.55 to 2.65 (mt, 3H: the other H of the $CH_2$N and the 2 other Hs of the 2 $CH_2$Ns of the morpholine); from 2.90 to 3.00 (mt, 1H: 1H of the $CH_2$ at 4β); 2.95 (s, 6H: $ArN(CH_3)_2$); from 3.15 to 3.30 (mt, 2H: 1H of the $CH_2$at 3δ and the other H of the $CH_2$ at4β); 3.18 (s, 3H: $NCH_3$); 3.49 (mt, 1H: the other H of the $CH_2$ at 3δ); 3.77 (mt, 4H: the 2 $CH_2$Os of the morpholine); 4.53 (t, J=7.5 Hz, 1 tH: CH at 3α); from 4.65 to 4.90 (mt, 2H: CH at 5γ and the other H of the $CH_2$ at 5ε); 4.79 (mt, 1H: CH at 2α); 4.88 (broad d, J=10 Hz, 1H: CH at 1α); 5.09 (mt, 1H: CH at 5α); 5.27 (dd, J=10 and 6 Hz, 1H: CH at 4α); 5.65 (d, J=8 Hz, 1H: CH at 6α); 5.89 (broad q, 1H: CH at 1β); 6.55 (d, J=10 Hz, 1H: CONH at 2); 6.64 (d, J=8 Hz, 2H: aromatic Hs at 4ε); 6.97 (d, J=8 Hz, 2H: aromatic Hs at 4δ); from 7.15 to 7.45 (mt: the 5 Hs corresponding to the aromatic Hs at 6α); 7.36 (limiting AB, 2H: $H_4$ and $H_5$); 7.84 (dd, J=4 and 2 Hz, 1H: H6); 8.42 (d, J=10 Hz, 1H: CONH at 1); 8.70 (d, J=8 Hz, 1H: CONH at 6); 11.66 (s, 1H: OH).

EXAMPLE 4

The process was performed as in Example 1, but starting with 100 cm³ of acetonitrile, 5 g of a crude mixture containing 50 mol % of 5δ-chloromethyl-5δ,5γ-dehydropristinamycin $I_E$ and 1.2 cm³ of di-n-propylamine. The reaction mixture was refluxed for 2 hours and then concentrated under reduced pressure to give 5.2 g of a solid which was purified by chromatography on silica (eluent: 98/2 dichloromethane/methanol by volume). 1.35 g of a solid were thus obtained, which product was purified in two portions (0.5 g and 0.75 9) by 2 successive preparative HPLC chromatographies on 450 g of 10 μm $C_8$ silica (eluent: 60/40 water/acetonitrile by volume containing 0.1% trifluoroacetic acid). For each batch, the fractions containing the expected product were combined and the acetonitrile was removed at 40° C. under reduced pressure (2.7 kPa). The residual aqueous phase was brought to pH 7–8 by addition of saturated aqueous sodium bicarbonate solution and was then extracted with 400 cm³ of dichloromethane. The organic phase was separated out after settling had taken place, dried over sodium sulphate, filtered and concentrated to dryness under reduced pressure. The two solids thus obtained were each crystallized in 100 cm³ of cyclohexane to give 0.3 g and 0.28 g, respectively, of a solid. The two batches were combined, dissolved in 10 cm³ of dichloromethane and 3 cm³ of ethanol, concentrated to dryness and then stirred in 20 cm³ of diisopropyl ether. The precipitate was filtered off and dried at 40° C. under reduced pressure (90 Pa) to give 0.35 g of 5δ-dipropylaminomethyl-5δ,5γ-dehydropristinamycin $I_E$ in the form of white crystals melting at 200–202° C.

$^1$H NMR spectrum (400 MHz, CDCl$_3$): from 0.85 to 0.95 (mt, 9H: CH$_3$ at 2γ and the 2 CH$_3$s of the dipropylamine); 1.10 (very broad d, J=16 Hz, 1H: 1H of the CH$_2$ at 5β); 1.25 (mt, 2H: 1H of the CH$_2$ at 3β and 1H of the CH$_2$ at 3γ); 1.32 (d, J=7 Hz, 3H: CH$_3$ at 1γ); 1.45 (mt, 4H: the 2 central CH$_2$s of the dipropylamine); from 1.50 to 1.65 (mt: 1H corresponding to the other H of the CH$_2$ at 3γ); 1.66 and 1.74 (2 mts, 1H each: CH$_2$ at 2β); 1.99 (mt, 1H: the other H of the CH$_2$ at 3β); 2.30 (mt, 4H: the 2 NCH$_2$s of the dipropylamine); 2.47 (broad dd, J=16 and 4.5 Hz, 1H: the other H of the CH$_2$ at 5β); from 2.80 to 3.05 (mt, 3H: 1H of the CH$_2$ at 4β and CH$_2$N); 2.94 (s, 6H: ArN(CH$_3$)$_2$; from 3.15 to 3.30 (mt, 2H: 1H of the CH$_2$ at 3β and the other H of the CH$_2$ at 4β); 3.17 (s, 3H: NCH$_3$); 3.33 (broad d, J=18 Hz, 1H: 1H of the CH$_2$ at 5ε); 3.46 (mt, 1H: the other H of the CH$_2$ at 3δ); 4.57 (dd, J=8 and 6 Hz, 1H: CH at 3α); 4.78 (mt, 1H: CH at 2α); 4.84 (broad d, J=18 Hz, 1H: the other H of the CH$_2$ at 5ε); 4.89 (broad d, J=10 Hz, 1H: CH at 1α); 5.13 (broad d, J=5 Hz, 1H: CH at 5α); 5.24 (dd, J=10 and 8 Hz, 1H: CH at 4α); 5.47 (mt, 1H: CH at 5γ); 5.56 (d, J=8 Hz, 1H: CH at 6α); 5.88 (broad q, J=7 Hz, 1H: CH at 1β) 6.57 (d, J=10 Hz, 1H: CONH at 2); 6.60 (d, J=8 Hz, 2H: aromatic Hs at 4ε); 6.92 (d, J=8 Hz, 2H: aromatic Hs at 4δ); from 7.20 to 7.40 (mt: the 7 Hs corresponding to the aromatic Hs at 6α- to H$_4$ and to H$_5$); 7.70 (broad d, J=4 Hz, 1H: H$_6$); 8.39 (d, J=10 Hz, 1H: CONH at 1); 8.42 (d, J=8 Hz, 1H: CONH at 6); 11.66 (s, 1H: OH).

EXAMPLE 5

The process was performed as in Example 1, but starting with 70 cm³ of acetonitrile, 5 g of a crude mixture containing 50 mol % of 5δ-chloromethyl-5δ,5γ-dehydropristinamycin $I_E$ and 0.7 cm³ of piperidine. The reaction mixture was refluxed for 45 minutes and then concentrated under reduced pressure to give 5.7 g of a solid which was purified by chromatography on silica (eluent: 99/1 to 95/5 by volume gradient of dichloromethane/methanol). The fractions containing the expected product were combined and then concentrated to dryness. The solid was stirred in 100 cm³ of cyclohexane, filtered and dried under reduced pressure to give 0.58 g of solid, which was crystallized from 50 cm³ of cyclohexane and then from 40 cm³ of the same solvent. The solid thus obtained was filtered off and dried at 40° C. under reduced pressure (90 Pa) to give 0.37 g of 5δ-piperidinomethyl-5δ,5γ-dehydropristinamycin $I_E$ in the form of a white cottony solid melting at 200–202° C.

$^1$H NMR spectrum (400 MHz, CDCl$_3$): 0.92 (t, J=7.5 Hz, 3H: CH$_3$ at 2γ); 1.08 (very broad d, J=16.5 Hz, 1H: 1H of the CH$_2$ at 5β); from 1.15 to 1.35 (mt, 2H: 1H of the CH$_2$ at 3β and 1H of the CH$_2$ at 3γ); 1.31 (d, J=7 Hz, 3H: CH$_3$ at 1γ); from 1.35 to 1.75 (mt, the 8 Hs corresponding to the other H of the CH$_2$ at 3γ- to the CH$_2$CH$_2$CH$_2$ of the piperidine and to 1H of the CH$_2$ at 2β); 1.75 (mt, 1H: the other H of the CH$_2$ at 2β); 2.00 (mt, 1H: the other H of the CH$_2$ at 3β); 2.29 (unres. mult., 4H: NCH$_2$ of the piperidine); 2.48 (broad dd, J=16.5 and 5 Hz, 1H: the other H of the CH$_2$ at 5β); 2.81 (s, 2H: CH$_2$N); 2.94 (s, 6H: ArN(CH$_3$)$_2$); 2.98 (dd, J=14 and 6.5 Hz, 1H: 1H the CH$_2$ at 4β); from 3.10 to 3.30 (mt, 2H: the other H of the CH$_2$ at 4β and 1H of the CH$_2$ at 3δ); 3.18 (s, 3H: NCH$_3$); 3.36 (broad d, J=18 Hz, 1H: 1H of the CH$_2$ at 5ε); 3.46 (mt, 1H: the other H of the CH$_2$ at 3δ); 4.59 (dd, J=8 and 5.5 Hz, 1H: CH at 3α); 4.78 (mt, 1H: CH at 2α); 4.83 (broad d, J=18 Hz, 1H: the other H of the CH$_2$ at 5ε); 4.88 (broad d, J=10 Hz, 1H: CH at 1α); 5.12 (d, J=5 Hz, 1tH: CH at 5α), 5.23 (dd, J=9 and 6.5 Hz, 1H: CH at 4α); 5.47 (mt, 1H: CH at 5γ); 5.53 (d, J=8 Hz, 1H: CH at 6α); 5.89 (broad q, J=7 Hz, 1H: CH at 1β); 6.58 (d, J=9.5 Hz, 1H: CONH at 2); 6.60 (d, J=8 Hz, 2H: aromatic Hs at 4ε); 6.93 (d, J=8 Hz, 2H: aromatic Hs at 4δ); from 7.20 to 7.40 (mt: the 7 Hs corresponding to the aromatic Hs at 6α- to H$_4$ and to H$_5$); 7.72 (broad d, J=4 Hz, 1H: H$_6$); from 8.35 to 8.45 (mt, 2H: CONH at 1 and CONH at 6); 11.68 (s, 1H: OH).

EXAMPLE 6

The process was performed as in Example 1, but starting with 50 cm³ of acetonitrile, 5.3 g of a crude mixture containing 25 mol % of 5δ-chloromethyl-5δ,5γ-dehydropristinamycin $I_E$ prepared under conditions identical to those described in Example 1, and 0.4 cm³ of pyrrolidine. The reaction mixture was refluxed for 45 minutes and was then concentrated under reduced pressure at 45° C. (2.7 kPa). The solid obtained was stirred in 100 cm³ of cyclohexane and 100 cm³ of diethyl ether. The precipate formed was filtered off, washed with 25 cm³ of diethyl ether and then chromatographed by preparative HPLC on 450 g of 10 μm $C_8$ silica (eluent: 65/35 by volume water/acetonitrile containing 0.1% trifluoroacetic acid). The fractions containing the expected product were combined and the acetonitrile was removed at 40° C. under reduced pressure (2.7 kPa). The residual aqueous solution was adjusted to pH 7–8 by addition of saturated aqueous sodium bicarbonate solution and then extracted with 100 cm³ of dichloromethane. The organic phase was dried over sodium sulphate, filtered and then concentrated to dryness under reduced pressure to give a solid which was stirred in 20 cm³ of diisopropyl ether, filtered off and then dried under reduced pressure at 45° C. (90 Pa). 0.49 g of 5δ-(1-pyrrolidinylmethyl)-5δ,5γ-dehydropristinamycin $I_E$ was thus obtained in the form of white crystals melting at 164–166° C.

$^1$H NMR spectrum (400 MHz, CDCl$_3$): 0.92 (t, J=7.5 Hz, 3H: CH$_3$ at 2γ); 1.11 (very broad d, J=17 Hz, 1H: 1H of the CH$_2$ at 5β); 1.24 (mt, 2H: 1H of the CH$_2$ at 3β) and 1H of the CH$_2$ at 3γ); 1.31 (d, J=7 Hz, 3H: CH$_3$ at 1γ); 1.54 (mt, 1H: the other H of the CH$_2$ at 3γ); from 1.60 to 1.85 (mt: the 6 Hs corresponding to the CH$_2$ at 2β and to the CH$_2$ of the pyrrolidine); 1.99 (mt, 1H: the other H of the CH$_2$ at 3β); 2.42 (mt, 4H: NCH$_2$ of the pyrrolidine); 2.48 (broad dd, J=17 and 5.5 Hz, 1H: the other H of the CH$_2$ at 5β); from 2.90 to 3.05 (mt, 1H: 1H of the CH$_2$ at 4β); 2.93 (s, 6H: ArN(CH$_3$)$_2$); 2.98 (s, 2H: CH$_2$N); from 3.15 to 3.30 (mt, 2H: the other H of the CH$_2$ at 4β and 1H of the CH$_2$ at 3); 3.16 (s, 3H: NCH$_3$); 3.38 (broad d, J=18 Hz, 1H: 1H of the CH$_2$ at 5ε); 3.45 (mt, 1H: the other H of the CH$_2$ at 3δ); 4.58 (dd, J=8.5 and 5.5 Hz, 1H: CH at 3α); 4.77 (mt, 1H: CH at 2α); from 4.80 to 4.95 (mt, 2H: the other H of the CH$_2$ at 5ε and CH at 1α); 5.10 (d, J=5.5 Hz, 1H: CH at 5α); 5.24 (dd, J=10 and 7 Hz, 1H: CH at 4α); 5.50 (mt, 1H: CH at 5γ); 5.54 (d, J=8 Hz, 1H: CH at 6α); 5.86 (resolved q, J=7 and 1 Hz, 1H: CH at 1β); 6.57 (d, J=9.5 Hz, 1H: CONH at 2); 6.59 (d, J=8 Hz, 2H: aromatic Hs at 4ε); 6.91 (d, J=8 Hz, 2H: aromatic Hs at 4δ); from 7.20 to 7.40 (mt: the 7 Hs corresponding to the aromatic Hs at 6α- to H$_4$ and to H$_5$); 7.71 (broad d, J=4 Hz, 1H: H$_6$); 8.39 (d, J=10 Hz, 1H: CONH at 1); 8.43 (d, J=8 Hz, 1H: CONH at 6); 11.66 (broad s, 1H: OH).

EXAMPLE 7

The process was performed as in Example 1, but starting with 100 cm$^3$ of acetonitrile, 10 g of a crude mixture containing 50 mol % of 5δ-chloromethyl-5δ,5γ-dehydropristinamycin I$_E$ and 3.7 cm$^3$ of 2,6-dimethylmorpholine (mixture of cis and trans isomers). The reaction mixture was refluxed for 1 hour and then concentrated under reduced pressure at 45° C. (2.7 kPa) to give 13.4 g of a solid which was taken up in 100 cm$^3$ of saturated aqueous sodium bicarbonate solution. The resulting mixture was extracted with twice 100 cm$^3$ of dichloromethane. The organic phases were combined, dried over sodium sulphate, filtered, and then concentrated to dryness to give 12.1 g of a yellow solid which was purified by two successive chromatograhies on silica (eluent: 98/2 by volume dichloromethane/methanol) to give a solid which was stirred in 30 cm$^3$ of diethyl ether, filtered off, and then dried under reduced pressure at 40° C. (90 Pa). 0.5 g of 5δ-dimethylmorpholinomethyl)-5δ,5γ-dehydropristinamycin I$_E$ (mixture of isomers) was thus obtained in the form of a cream-colored solid melting at about 165° C.

$^1$H NMR spectrum (400 MHz, CDCl$_3$). A mixture of the two cis and trans diastereoisomers on the morpholine was observed: 0.92 (t, J=7.5 Hz, 3H: CH$_3$ at 2γ); 1.02 (very broad d, J=17 Hz, 1H: 1H of the CH$_2$ at 5β); 1.15 and 1.20 (2d, J=7 Hz, 3H each: CH$_3$ of the 2,6-dimethylmorpholine); from 1.20 to 1.45 (mt, 2H: 1H of the CH$_2$ at 3b and 1H of the CH$_2$ at 3γ); 1.30 (d, J=7 Hz, 3H: CH$_3$ at 1γ); 1.55 (mt, 1H: the other H of the CH$_2$ at 3γ); from 1.60 to 1.75 (mt: the 3 Hs corresponding to the 1H of CH$_2$ at 2β and to 2H of the NCH$_2$s of the 2,6-dimethylmorpholine); 1.74 (mt, 1H: the other H of the CH$_2$ at 2β); 2.00 (mt, 1H: the other H of the CH$_2$ at 3β); 2.45 (broad dd, J=17 and 5.5 Hz, 1H: the other H of the CH$_2$ at 5β); 2.68 (mt, 2H: the 2 other Hs of the NCH$_2$ of the 2,6-dimethylmorpholine); 2.77 and 2.86 (2d, J=13 Hz, 1H each: CH$_2$N); from 2.90 to 3.00 (mt, 1H: 1H of the CH$_2$ at 4β); 2.95 (s, 6H: ArN(CH$_3$)$_2$); from 3.15 to 3.30 (mt, 2H: the other H of the CH$_2$ at 4β and 1H of the CH$_2$ at 3δ); 3.17 (s, 3H: NCH$_3$); 3.32 (broad d, J=18 Hz, 1H: 1H of the CH$_2$ at 5ε); 3.47 (mt, 1H: the other H of the CH$_2$ at 3δ); 3.60 and 3.70 (2 mts, 1H each: CHO of the morpholine); 4.58 (dd, J=8.5 and 5.5 Hz, 1H: CH at 3α); 4.77 (mt, 1H: CH at 2α); 4.84 (broad d, J=18 Hz, 1H: the other H of the CH$_2$ at 5ε); 4.88 (dd, J=10 and 1 Hz, 1H: CH at 1α); 5.10 (d, J=5.5 Hz, 1H: CH at 5α); 5.21 (dd, J=9 and 6.5 Hz, 1H: CH at 4α); 5.48 (mt, 1H: CH at 5γ); 5.52 (d, J=8 Hz, 1H: CH at 6α); 5.87 (resolved q, J=7 and 1 Hz, 1H: CH at 1β); 6.56 (d, J=9.5 Hz, 1H: CONH at 2); 6.58 (d, J=8 Hz, 2H: aromatic Hs at 4ε); 6.90 (d, J=8 Hz, 2H: aromatic Hs at 4δ); from 7.20 to 7.40 (mt: the 7 Hs corresponding to the aromatic Hs at 6α- to H$_4$ and to H$_5$); 7.72 (dd, J=4 and 1 Hz, 1H: H$_5$); 8.39 (d, J=10 Hz, 1H: CONH at 1); 8.48 (d, J=8 Hz, 1H: CONH at 6); 11.66 (s, 1H: OH).

EXAMPLE 8

The process was performed as in Example 1, but starting with 100 cm$^3$ of acetonitrile, 10 g of a crude mixture containing 40 mol % of 5δ-chloromethyl-5δ,5γ-dehydropristinamycin I$_E$ and 3.8 g of 4-(4-fluorophenyl)-1,2,3,6-tetrahydropyridine hydrochloride and 2.75 cm$^3$ of triethylamine. The reaction mixture was refluxed for 1 hour and then concentrated under reduced pressure (45° C.; 2.7 kPa) to give 14.3 g of a brown-colored solid which was purified by 2 preparative HPLC chromatographies on 450 g of 10 μm C$_8$ silica (eluent: 65/35 by volume water/acetonitrile containing 0.1% trifluoroacetic acid). The fractions containing the expected product were combined and the acetonitrile was removed at 40° C. under reduced pressure (2.7 kPa). The pH of the residual aqueous phase was adjusted to 7–8 by addition of saturated aqueous sodium bicarbonate solution. The precipitate obtained was filtered off, rinsed with 50 cm$^3$ of diisopropyl ether, and then dried at 40° C. (90 Pa) to give 0.63 g of 5δ-[4-(4-fluorophenyl)-1,2,3,6-tetrahydropyridylmethyl]-5δ,5γ-dehydropristinamycin I$_E$ in the form of a yellow solid melting at 172° C.

$^1$H NMR spectrum (600 MHz, CDCl$_3$): 0.90 (t, J=7.5 Hz, 3H: CH$_3$ at 2γ); 1.13 (very broad d, J=16 Hz, 1H: 1H of the CH$_2$ at 5β); 1.21 (mt, 2H: 1H of the CH$_2$ at 3β and 1H of the CH$_2$ at 3γ); 1.30 (d, J=7 Hz, 3H: CH$_3$ at 1γ); 1.53 (mt, 1H: the other H of the CH$_2$ at 3γ); 1.65 and 1.73 (2 mts: the 2 Hs corresponding to the CH$_2$ at 2β); 1.98 (mt, 1H: the other H of the CH$_2$ at 3β); from 2.40 to 2.65 (mt, 5H: NCH$_2$CH$_2$ of the 1,2,3,6-tetrahydropyridine and the other H of the CH$_2$ at 5β); from 2.90 to 3.05 (mt, 3H: CH$_2$N and 1H of the CH$_2$ at 4β); 2.93 (s, 6H: ArN(CH$_3$)$_2$); 3.06 (mt, 2H: NCH$_2$ of the 1,2,3,6-tetrahydropyridine); from 3.10 to 3.30 (mt, 2H: the other H of the CH$_2$ at 4β and 1H of the CH$_2$ at 3δ); 3.15 (s, 3H: NCH$_3$); 3.40 (broad d, J=18 Hz, 1H: 1H of the CH$_2$ at 5ε); 3.45 (mt, 1H: the other H of the CH$_2$ at 3δ); 4.56 (dd, J=8 and 6 Hz, 1H: CH at 3α); 4.76 (mt, 1H: CH at 2α); 4.83 (d, J=18 Hz, 1H: the other H of the CH$_2$ at 5ε); 4.86 (broad d, J=10 Hz, 1H: CH at 1α); 5.12 (d, J=5.5 Hz, 1H: CH at 5α); 5.22 (dd, J=9 and 7 Hz, 1H: CH at 4α); 5.54 (d, J=8 Hz, 1H: CH at 6α); 5.56 (mt, 1H: CH at 5γ); 5.87 (broad q, J=7 Hz, 1H: CH at 1β); 6.00 (mt, 1H: CH= of the 1,2,3,6-tetrahydropyridine); 6.56 (d, J=9.5 Hz, 1H: CONH at 2); 6.59 (d, J=8 Hz, 2H: aromatic Hs at 4ε); 6.92 (d, J=8 Hz, 2H: aromatic Hs at 4δ); 6.97 (t, J=8.5 Hz, 2H: aromatic Hs ortho to the F); from 7.20 to 7.30 (mt: the 5 Hs corresponding to the aromatic Hs at 6α); from 7.30 to 7.40 (mt, 4H: aromatic Hs meta to the F—H$_4$ and H$_5$); 7.71 (d, J=4 Hz, 1H: H$_6$); 8.48 (d, J=10 Hz, 1H: CONH at 1); 8.45 (d, J=8 Hz, 1H: CONH at 6); 11.65 (s, 1H: OH).

EXAMPLE 9

The process was performed as in Example 1, but starting with 50 cm$^3$ of acetonitrile, 5 g of a crude mixture containing 50 mol % of 5δ-chloromethyl-5δ,5γ-dehydropristinamycin I$_E$ and 0.6 g of thiomorpholine. The reaction mixture was heated for 2 hours and then concentrated under reduced pressure at 45° C. (2.7 kPa). The solid was taken up in 100 cm³ of water. The insoluble material was filtered off and washed with 20 cm³ of water to give 5.4 g of a brown-colored solid which was purified by chromatography on silica (eluent: 99/1 to 98/2 by volume gradient of dichloromethane/methanol), and then by preparative HPLC on 450 g of 10 μm C₈ silica (eluent: 65/35 by volume water/acetonitrile containing 0.1% trifluoroacetic acid). The fractions containing the expected product were combined, the acetonitrile was removed at 40° C. under reduced pressure (2.7 kPa), and the pH of the residual aqueous phase was adjusted to 7–8 by addition of saturated aqueous sodium bicarbonate solution. The precipitate obtained was filtered off, washed with 20 cm³ of water, and dried at 45° C. (90 Pa) to give 0.31 g of 5δ-thiomorpholinomethyl-5δ,5γ-dehydropristinamycin $I_E$ in the form of a white solid melting at 160° C.

¹H NMR spectrum (400 MHz, CDCl₃): 0.91 (t, J=7.5 Hz, 3H: CH₃ at 2γ); 1.04 (very broad d, J=16 Hz, 1H: 1H of the CH₂ at 5β); from 1.15 to 1.35 (mt, 2H: 1H of the CH₂ at 3β and 1H of the CH₂ at 3γ); 1.31 (d, J=7 Hz, 3H: CH₃ at 1γ); 1.55 (mt, 1H: the other H of the CH₂ at 3γ); from 1.60 to 1.85 (mt: the 2 Hs corresponding to the CH₂ at 2β); 2.00 (mt, 1H: the other H of the CH₂ at 3β); 2.46 (very broad d, J=16 Hz, 1H: the other H of the CH₂ at 5β); 2.65 (unres. mult., 8H: NCH₂CH₂S of the thiomorpholine); 2.90 (broad s, 2H: CH₂N); 2.95 (s, 6H: ArN(CH₃)₂); from 2.95 to 3.05 (mt, 1H: 1H of the CH₂ at 4β); from 3.10 to 3.25 (mt, 2H: the other H of the CH₂ at 4β and 1H of the CH₂ at 3δ); 3.19 (s, 3H: NCH₃); 3.29 (broad d, J=18 Hz, 1H: 1H of the CH₂ at 5ε); 3.47 (mt, 1H: the other H of the CH₂ at 3δ); 4.59 (dd, J=8 and 6.5 Hz, 1H: CH at 3α); from 4.75 to 4.85 (mt, 1H: CH at 2α); 4.82 (broad d, J=18 Hz, 1H: the other H of the CH₂ at 5ε); 4.89 (broad d, J=10 Hz, 1H: CH at 1α); 5.11 (broad d, J=5 Hz, 1H: CH at 5α); 5.24 (mt, 1H: CH at 4α); 5.50 (mt, 1H: CH at 5γ); 5.53 (d, J=8.5 Hz, 1H: CH at 6α); 5.89 (broad q, J=7 Hz, 1H: CH at 1β); from 6.55 to 6.65 (mt, 1H: CONH at 2); 6.59 (d, J=8 Hz, 2H: aromatic Hs at 4ε); 6.92 (d, J=8 Hz, 2H: aromatic Hs at 4δ); from 7.20 to 7.45 (mt: the 7 Hs corresponding to the aromatic Hs at 6α- to H₄ and to H₅); 7.74 (mt, 1H: H₆); 8.41 (d, J=10 Hz, 1H: CONH at 1); 8.51 (d, J=8.5 Hz, 1H: CONH at 6); 11.68 (s, 1H: OH).

EXAMPLE 10

The process was performed as in Example 1, but starting with 200 cm³ of acetonitrile, 6 g of a crude mixture containing 50 mol % of 5δ-chloromethyl-5δ,5γ-dehydropristinamycin $I_E$ and 4.8 g of 4-acetyl-4-phenylpiperidine. The reaction mixture was heated for 3 hours and then concentrated under reduced pressure at 45° C. (2.7 kPa). The solid was taken up in 100 cm³ of water and 100 cm³ of dichloromethane. The organic phase was separated out after settling had taken place and then dried over sodium sulphate, filtered, and concentrated to dryness to give 10.6 g of a brown-colored solid which was purified by 2 successive chromatographies on silica (eluent: 97/3 by volume dichloromethane/methanol). A solid was thus obtained which was stirred in 30 cm³ of diethyl ether, filtered off, and then dried at 45° C. (90 Pa) to give 0.46 g of 5δ-(4-acetyl-4-phenylpiperidinomethyl)-5δ,5γ-dehydropristinamycin $I_E$, in the form of a yellow solid melting at 171° C.

¹H NMR spectrum (400 MHz, CDCl₃): 0.93 (t, J=7.5 Hz, 3H: CH₃ at 2γ); 1.06 (very broad d, J=16 Hz, 1H: 1H of the CH₂ at 5β); from 1.15 to 1.35 (mt, 2H: 1H of the CH₂ at 3β and 1H of the CH₂ at 3γ); 1.31 (d, J=7 Hz, 3H: CH₃ at 1γ); 1.53 (mt, 1H: the other H of the CH₂ at 3γ); from 1.60 to 1.85 (mt: the 2 Hs corresponding to the CH₂ at 2β); from 1.90 to 2.25–2.45 and 2.62 (3 series of in total mt, 8H: NCH₂CH₂ of the piperidine); 1.91 (s, 3H: COCH₃); 2.00 (mt, 1H: the other H of the CH₂ at 3β); from 2.40 to 2.45 (mt, 1H: the other H of the CH₂ at 5β); 2.82 (broad s, 2H: CH₂N); from 2.85 to 3.05 (mt, 1H: 1H of the CH₂ at 4β); 2.94 (s, 6H: ArN(CH₃)₂); from 3.10 to 3.30 (mt, 2H: the other H of the CH₂ at 4β and 1H of the CH₂ at 3δ); 3.16 (s, 3H: NCH₃); 3.31 (broad d, J=18 Hz, 1H: 1H of the CH₂ at 5ε); 3.48 (mt, 1H: the other H of the CH₂ at 3δ); 4.58 (dd, J=8 and 5.5 Hz, 1H: CH at 3α); from 4.70 to 4.85 (mt, 2H: CH at 2α and the other H of the CH₂ at 5ε); 4.89 (broad d, J=10 Hz, 1H: CH at 1α); 5.10 (broad d, J=5.5 Hz, 1H: CH at 5); 5.23 (dd, J=9 and 7 Hz, 1H: CH at 4α); 5.47 (mt, 1H: CH at 5γ); 5.56 (d, J=8 Hz, 1H: CH at 6α); 5.89 (broad q, J=7 Hz, 1H: CH at 1β); from 6.55 to 6.65 (mt, 1H: CONH at 2); 6.60 (d, J=8 Hz, 2H: aromatic Hs at 4ε); 6.91 (d, J=8 Hz, 2H: aromatic Hs at 4δ); from 7.15 to 7.40 (mt: the 12 Hs corresponding to the aromatic Hs at 6α- to the aromatic Hs of the phenyl- to H₄ and to H₅); 7.74 (broad d, J=4 Hz, 1H: H₆); 8.42 (d, J=10 Hz, 1H: CONH at 1); 8.49 (d, J=8 Hz, 1H: CONH at 6); 11.67 (s, 1H: OH).

EXAMPLE 11

The process was performed as in Example 1, but starting with 100 cm³ of acetonitrile, 6 g of a crude mixture containing 40 mol % of 5δ-chloromethyl-5δ,5γ-dehydropristinamycin $I_E$ and 2.4 cm³ of N-methylbutylamine. The reaction mixture was heated for 3 hours and then concentrated under reduced pressure at 45° C. (2.7 kPa). The solid was taken up in 100 cm³ of water and the resulting mixture was extracted with twice 70 cm³ of dichloromethane. The organic phase was separated out after settling had taken place and then dried over sodium sulphate, filtered, and concentrated to dryness to give 6.5 g of crude product, which product was purified by 2 successive chromatographies on silica (eluent: 97/3 by volume dichloromethane/methanol). A solid was thus obtained which was stirred in 30 cm³ of diethyl ether, filtered off, and then dried at 40° C. (90 Pa) to give 0.50 g of 5δ-N-methyl-N-butylaminomethyl-5δ,5γ-dehydropristinamycin $I_E$ in the form of a yellow solid melting at 168° C.

¹H NMR spectrum (500 MHz, CDCl₃): from 0.85 to 0.95 (mt, 6H: CH₃ at 2γ and CH₃ of butyl); 1.10 (very broad d, J=16 Hz, 1H: 1H of the CH₂ at 5β); from 1.15 to 1.30 (mt, 2H: 1H of the CH₂ at 3β and 1H of the CH₂ at 3γ); 1.30 (d, J=7 Hz, 3H: CH₃ at 1γ); 1.34 and 1.44 (2 mts, 2H each: central CH₂CH₂ of the butyl); 1.54 (mt, 1H: the other H of the CH₂ at 3γ); 1.66 (mt: 1H of the CH₂ at 2β); 1.74 (mt: 1H corresponding to the other H of the CH₂ at 2β); 1.99 (mt, 1H: the other H of the CH₂ at 3β); 2.11 (s, 3H: NCH₃); 2.27 (mt, 2H: NCH₂ of the butyl); 2.47 (broad dd, J=16 and 5 Hz, 1H: the other H of the CH₂ at 5β); 2.83 (AB, J=13 Hz, 2H: CH₂N); 2.93 (s, 6H: ArN(CH₃)₂); 2.98 (dd, J=14 and 6.5 Hz, 1H: 1H of the CH₂ at 4β); from 3.15 to 3.30 (mt, 2H: 1H of the CH₂ at 3δ and the other H of the CH₂ at 4β); 3.17 (s, 3H: NCH₃); 3.34 (broad d, J=18 Hz, 1H: 1H of the CH₂ at 5ε); 3.46 (mt, 1H: the other H of the CH₂ at 3δ); 4.57 (dd, J=8 and 5.5 Hz, 1H: CH at 3α); from 4.75 to 4.85 (mt, 1H: CH at 2α); 4.80 (broad d, J=18 Hz, 1H: the other H of the CH₂ at 5ε); 4.87 (dd, J=10 and 1 Hz, 1H: CH at 1α); 5.11 (broad d, J=5 Hz, 1H: CH at 5α); 5.24 (dd, J=9 and 6.5 Hz, 1H: CH at 4α); 5.48 (mt, 1H: CH at 5γ); 5.56 (d, J=8 Hz, 1H: CH at 6α); 5.87 (resolved q, J=7 and 1 Hz, 1H: CH at 1b); 6.60 (d, J=8 Hz, 2H: aromatic Hs at 4ε); 6.52 (d, J=10 Hz, 1H: CONH at 2); 6.92 (d, J=8 Hz, 2H: aromatic Hs at 4δ); from 7.20 to 7.35 (mt: the 7 Hs corresponding to the aromatic Hs at 6α- to H₄ and to H₅); 7.72 (broad d, J=4 Hz, 1H: H₆); 8.39

(d, J=10 Hz, 1H: CONH at 1); 8.43 (d, J=8 Hz, 1H: CONH at 6); 11.68 (broad s, 1H: OH).

EXAMPLE 12

The process was performed as in Example 1, but starting with 100 cm$^3$ of acetonitrile, 6 g of a crude mixture containing 40 mol % of 5δ-chloromethyl-5δ,5γ-dehydropristinamycin I$_E$, and 2 cm$^3$ of (S)-prolinol. The reaction mixture was heated for 3 hours and then concentrated under reduced pressure at 45° C. (2.7 kPa). The solid was taken up in 200 cm$^3$ of water and 100 cm$^3$ of dichloromethane. The organic phase was separated out after settling had taken place and then dried over sodium sulphate, filtered, and concentrated to dryness to give 6.2 g of crude product, which product was chromatographed on silica (eluent: 95/5 by volume dichloromethane/methanol). A solid was obtained, which was stirred in 30 cm$^3$ of diethyl ether and 30 cm$^3$ of petroleum ether, filtered off, and then dried at 40° C. (90 Pa) to give 0.67 g of 5δ-[(S)-2-hydroxymethylpyrrolidon]methyl-5δ,5γ-dehydropristinamycin I$_E$ in the form of a yellow solid melting at 147° C.

$^1$H NMR spectrum (400 MHz, CDCl$_3$): 0.92 (t, J=7.5 Hz, 3H: CH$_3$ at 2γ); 1.01 (very broad d, J=17 Hz, 1H: 1H of the CH$_2$ at 5β); from 1.15 to 1.30 (mt, 2H: 1H of the CH$_2$ at 3β and 1H of the CH$_2$ at 3γ); 1.31 (d, J=7 Hz, 3H: CH$_3$ at 1γ); 1.57 (mt, 1H: the other H of the CH$_2$ at 3γ); from 1.60 to 2.00 (mt: the 6 Hs corresponding to the CH$_2$ at 2β and to the CH$_2$s of the pyrrolidine); 2.02 (mt, 1H: the other H of the CH$_2$ at 3β); 2.30 (mt, 1H: 1H of the NCH$_2$ of the pyrrolidine); 2.44 (broad dd, J=17 and 5 Hz, 11H: the other H of the CH$_2$ at 5β); 2.62 (mt, 1H: NCH of the pyrrolidine); 2.77 (broad d, J=12 Hz, 1H: 1H of the CH$_2$N); from 2.85 to 3.05 (mt, 1H: 1H of the CH$_2$ at 4β); 2.94 (s, 6H: ArN(CH$_3$)$_2$); from 3.05 to 3.35 (mt, 5H: the other H of the NCH$_2$ of the pyrrolidine- the other H of the CH$_2$ at 4β- the other H of the CH$_2$N-1H of the CH$_2$ at 3δ and 1H of the CH$_2$ at 5ε); 3.19 (s, 3H: NCH$_3$); 3.40 (mt, 1H: 1H of the CH$_2$O); 3.46 (mt, 1H: the other H of the CH$_2$ at 3δ); 3.64 (dd, J=11.5 and 3 Hz, 1H: the other H of the CH$_2$O); 4.56 (dd, J=8 and 5.5 Hz, 1H: CH at 3α); 4.78 (mt, 1H: CH at 2α); 4.88 (dd, J=10 and 1 Hz, 1H: CH at 1α); 4.94 (broad d, J=18 Hz, 1H: the other H of the CH$_2$ at 5ε); 5.12 (d, J=5.5 Hz, 1H: CH at 5α); 5.24 (dd, J=9 and 6.5 Hz, 1H: CH at 4α); 5.51 (mt, 1H: CH at 5γ); 5.59 (d, J=8 Hz, 1H: CH at 6α); 5.87 (resolved q, J=7 and 1 Hz, 1H: CH at 1α); from 6.55 to 6.70 (mt, 1H: CONH at 2); 6.59 (d, J=8 Hz, 2H: aromatic Hs at 4ε); 6.94 (d, J=8 Hz, 2H: aromatic Hs at 4δ); from 7.20 to 7.40 (mt: the 7 Hs corresponding to the aromatic Hs at 6α- to H$_4$ and to H$_5$); 7.74 (dd, J=4 and 1.5 Hz, 1H: H$_6$); 8.41 (d, J=10 Hz, 1H: CONH at 1); 8.49 (d, J=8 Hz, 1H: CONH at 6); 11.68 (broad s, 1H: OH).

EXAMPLE 13

The process was performed as in Example 1, but starting with 50 cm$^3$ of acetonitrile, 2 g of a crude mixture containing 40 mol % of 5δ-chloromethyl-5δ,5γ-dehydropristinamycin I$_E$ and 0.75 cm$^3$ of 2-(N-methyl-N-aminomethyl)-1,3-dioxolane. The reaction mixture was heated for 3 hours and then concentrated under reduced pressure at 45° C. (2.7 kPa). The solid was taken up in 100 cm$^3$ of water and 100 cm$^3$ of dichloromethane. The organic phase was separated out after settling had taken place and then dried over sodium sulphate, filtered and concentrated to dryness to give 2.0 g of a yellow solid which was purified by chromatography on silica (eluent: 97/3 by volume dichloromethane/methanol). After concentration of the fractions, the solid obtained was dried at 40° C. (90 Pa) to give 0.24 g of 5δ-[N-methyl-N-2-(1,3-dioxolanyl)methyl]aminomethyl-5δ,5γ-dehydropristinamycin I$_E$, in the form of a yellow solid melting at 149° C.

$^1$H NMR spectrum (400 MHz, CDCl$_3$): 0.91 (t, J=7.5 Hz, 3H: CH$_3$ at 2γ); 1.01 (very broad d, J=16 Hz, 1H: 1H of the CH$_2$ at 5β); from 1.15 to 1.35 (mt, 2H: 1H of the CH$_2$ at 3β and 1H of the CH$_2$ at 3γ); 1.30 (d, J=7 Hz, 3H: CH$_3$ at 1γ); 1.53 (mt, 1H: the other H of the CH$_2$ at 3γ); from 1.60 to 1.80 (mt: the 2 Hs corresponding to the CH$_2$ at 2β); 1.98 (mt, 1H: the other H of the CH$_2$ at 3β); 2.28 (s, 3H: NCH$_3$); 2.44 (broad dd, J=16 and 5 Hz, 1H: the other H of the CH$_2$ at 5β); 2.50 and 2.58 (2 dd, J=13 and 4.5 Hz, 1H each: NCH$_2$); from 2.85 to 3.05 (mt, 3H: 1H of the CH$_2$ at 4β and CH$_2$N at 5δ); 2.94 (s, 6H: ArN(CH$_3$)$_2$); from 3.10 to 3.30 (mt, 2H: the other H of the CH$_2$ at 4β and 1H of the CH$_2$ at 3); 3.17 (s, 3H: NCH$_3$); 3.36 (broad d, J=18 Hz, 1H of CH$_2$ at 5ε); 3.44 (mt, 1H: the other H of the CH$_2$ at 3δ); from 3.75 to 4.00 (mt, 4H: OCH$_2$CH$_2$O); 4.56 (dd, J=8 and 5.5 Hz, 1H: CH at 3α); 4.76 (mt, 1H: CH at 2α); 4.83 (broad d, J=18 Hz, 1H: the other H of CH$_2$ at 5ε); 4.88 (dd, J=10 and 1 Hz, 1H: CH at 1α); 4.97 (t, J=4.5 Hz 1H: OCHO); 5.11 (d, J=5.5 Hz, 1H: CH at 5α); 5.21 (dd, J=9 and 6 Hz, 1H: CH at 4α); 5.48 (mt, 1H: CH at 5γ); 5.57 (d, J=8 Hz, 1H: CH at 6α); 5.87 (resolved q, J=7 and 1 Hz, 1H: CH at 1β); 6.57 (d, J=9 Hz, 1H: CONH at 2); 6.62 (d, J=8 Hz, 2H: aromatic Hs at 4ε); 6.93 (d, J=8 Hz, 2H: aromatic Hs at 4δ); from 7.20 to 7.40 (mt: the 7 Hs corresponding to the aromatic Hs at 6α- to H$_4$ and to H$_5$); 7.72 (dd, J=4 and 1 Hz, 1H: H$_6$); 8.39 (d, J=10 Hz, 1H: CONH at 1); 8.44 (d, J=8 Hz, 1H: CONH at 6); 11.67 (broad s, 1H: OH).

EXAMPLE 14

The process was performed as in Example 1, but starting with 100 cm$^3$ of acetonitrile, 10 g of a crude mixture containing 33 mol % of 5δ-chloromethyl-5δ,5γ-dehydropristinamycin I$_E$ and 3.5 g of 4-piperidinoethanol. The reaction mixture was heated for 2 hours and then concentrated under reduced pressure at 45° C. (2.7 kPa). The solid obtained was taken up in 50 cm$^3$ of water and 50 cm$^3$ of dichloromethane. The organic phase was separated out after settling had taken place, dried over sodium sulphate, filtered, and concentrated to dryness to give 6.2 g of a brown-colored solid which was purified on silica (eluent: 95/5 by volume dichloromethane/methanol) and then by HPLC on 450 g of 10 μm C$_8$ silica (eluent: 70/30 by volume water/acetonitrile containing 0.1% trifluoroacetic acid). The fractions containing the expected product were combined, the acetonitrile was removed at 40° C. under reduced pressure (2.7 kPa), and the pH of the residual aqueous phase was adjusted to 7–8 by addition of saturated aqueous sodium bicarbonate solution. The aqueous phase was extracted with twice 50 cm$^3$ of dichloromethane. The organic phases were combined and then dried over sodium sulphate, filtered, and concentrated to dryness. The solid obtained was stirred in 25 cm$^3$ of diethyl ether, filtered off, washed with 10 cm$^3$ of diisopropyl ether, and then dried at 40° C. (90 Pa) to give 0.70 g of 5δ-[4-(-2-hydroxyethyl)piperidino]methyl-5δ,5γ-dehydropristinamycin I$_E$ in the form of a white solid melting at 240° C.

$^1$H NMR spectrum (500 MHz, CDCl$_3$): 0.93 (t, J=7.5 Hz, 3H: CH$_3$ at 2γ); 1.10 (very broad d, J=16.5 Hz, 1H: 1H of the CH$_2$ at 5β); from 1.15 to 1.35 (mt, 2H: 1H of the CH$_2$ at 3β and 1H of the CH$_2$ at 3β); from 1.15 to 1.80 (mt, 5H: CH$_2$ of the piperidine and CH of the piperidine); 1.32 (d, J=7 Hz, 3H: CH$_3$ at 1γ); from 1.45 to 1.60 (mt, 1H: the other H of the CH$_2$ at 3γ); 1.51 (q, J=7 Hz, 2H: CH$_2$ of the hydroxyethyl); from 1.60 to 1.80 (mt, 2H: CH$_2$ at 2β); 1.84 (broad t, J=11 Hz, 2H: axial Hs of the NCH$_2$s of the piperidine); 2.00 (mt, 1H: the other H of the CH$_2$ at 3β); 2.49 (broad dd, J=16.5 and 5.5 Hz, 1H: the other H of the CH$_2$ at 5β); from 2.75 to 2.90 (mt, 4H: CH$_2$N and equatorial Hs of the NCH$_2$s of the piperidine); 2.95 (s, 6H: ArN(CH$_3$)$_2$); 2.99 (dd, J=14 and 6.5 Hz, 1H: 1H of the CH$_2$ at 4β); from 3.15 to 3.35 (mt, 2H: the other H of the CH$_2$ at 4β and 1H of the CH$_2$ at 3δ); 3.18 (s, 3H: NCH$_3$); 3.35 (broad d, J=17.5 Hz, 1H: 1H of the CH$_2$ at 5ε); 3.47 (mt, 1H: the other H of the CH$_2$ at 3δ); 3.70 (t, J=7 Hz, 2H: CH$_2$O); 4.59 (dd, J=8.5 and 6 Hz, 1H: CH at 3α); 4.78 (mt, 1H: CH at 2α); 4.83 (broad d, J=17.5 Hz, 1H: the other H of the CH$_2$ at 5ε); 4.87 (broad d, J=10 Hz, 1H: CH at 1α); 5.12 (d, J=5.5 Hz, 1H: CH at 5α); 5.24 (dd, J=8 and 6.5 Hz, 1H: CH at 4α); 5.48 (mt, 1H: CH at 5γ); 5.54 (d, J=7.5 Hz, 1H: CH at 6α); 5.89 (q, J=7 Hz, 1H: CH at 1β); from 6.55 to 6.65 (mt, 1H: CONH at 2); 6.59 (d, J=8 Hz, 2H: aromatic Hs at 4ε); 6.92 (d, J=8 Hz, 2H: aromatic Hs at 4δ); from 7.25 to 7.40 (mt: the 7 Hs corresponding to the aromatic Hs at 6α- to H$_4$ and to H$_5$); 7.73 (broad d, J=4 Hz, 1H: H$_6$); 8.39 (d, J=10 Hz, 1H: CONH at 1); 8.43 (d, J=7.5 Hz, 1H: CONH at 6): 11.67 (broad s, 1H: OH).

EXAMPLE 15

The process was performed as in Example 1, but starting with 100 cm$^3$ of acetonitrile, 7 g of a crude mixture containing 33 mol % of 5δ-chloromethyl-5δ,5γ-dehydropristinamycin I$_E$, and 1.25 cm$^3$ of 1-(2-pyridyl) piperazine. The reaction mixture was heated for 2 hours at 60° C. and then concentrated under reduced pressure at 45° C. (2.7 kPa). The solid was taken up in 50 cm$^3$ of water and 100 cm$^3$ of dichloromethane. The aqueous phase was re-extracted with 30 cm$^3$ of dichloromethane. The organic phases were combined, dried over magnesium sulphate, filtered, and concentrated to dryness to give 7.6 g of a beige-colored solid which was purified by two successive flash chromatographies on silica (eluent: 95/5 and then 98/2 by volume dichloromethane/methanol). A solid was thus obtained, which was stirred in 60 cm$^3$ of diethyl ether, filtered off, and dried at 40° C. (90 Pa) to give 1.5 g of 5δ-[4-(2-pyridyl)piperazin-1-yl]methyl-5δ,5γ-dehydropristinamycin I$_E$ in the form of a beige-colored powder melting at 148° C.

$^1$H NMR spectrum (400 MHz, CDCl$_3$): 0.91 (t, J=7.5 Hz, 3H: CH$_3$ at 2γ); 1.06 (very broad d, J=16 Hz, 1H: 1H of the CH$_2$ at 5β); 1.22 (mt, 2H: 1H of the CH$_2$ at 3β and 1H of the CH$_2$ at 3γ); 1.32 (d, J=7 Hz, 3H: CH$_3$ at 1γ); 1.55 (mt, 1H: the other H of the CH$_2$ at 3γ); from 1.60 to 1.80 (mt: the 2 Hs corresponding to the CH$_2$ at 2β); 1.98 (mt, 1H: the other H of the CH$_2$ at 3β); from 2.40 to 2.55 (mt, 5: the other H of the CH$_2$ at 5β and CH$_2$N of the piperazine); 2.90 (s, 2H: CH$_2$N); 2.95 (s, 6H: ArN(CH$_3$)$_2$); 2.98 (dd, J=14 and 6.5 Hz, 1H: 1H of the CH$_2$ at 4β); from 3.10 to 3.30 (mt, 2H: 1H of the CH$_2$ at 3δ and the other H of the CH$_2$ at 4β); 3.18 (s, 3H: NCH$_3$); 3.36 (broad d, J=18 Hz, 1H: 1H of the CH$_2$ at 5ε); from 3.40 to 3.65 (mt, 5H: the other H of the CH$_2$ at 3δ and CH$_2$NAr of the piperazine); 4.60 (dd, J=8 and 5.5 Hz, 1H: CH at 3α); 4.78 (mt, 1H: CH at 2α); 4.88 (broad d, J=18 Hz, 1H: the other H of the CH$_2$ at 5ε); 4.88 (dd, J=10 and 1 Hz, 1H: CH at 1ε); 5.12 (broad d, J=5.5 Hz, 1H: CH at 5α); 5.24 (dd, J=9 and 6.5 Hz, 1H: CH at 4α); 5.51 (mt, 1H: CH at 5γ); 5.54 (d, J=8.5 Hz, 1H: CH at 6α); 5.88 (resolved q, J=7 and 1 Hz, 1H: CH at 1β); from 6.50 to 6.70 (mt, 3H: CONH at 2 —H at 3 of the pyridine and H at 5 of the pyridine); 6.60 (d, J=8 Hz, 2H: aromatic Hs at 4ε); 6.92 (d, J=8 Hz, 2H: aromatic Hs at 4δ); from 7.20 to 7.40 (mt: the 7 Hs corresponding to the aromatic Hs at 6α- to H$_4$ and to H$_5$); 7.46 (resolved t, J=8 and 2 Hz, 1H: H at 4 of the pyridine); 7.73 (dd, J=4 and 1.5 Hz, 1H: H$_6$); 8.18 (dd, J=5 and 2 Hz, 1H: H at 6 of the pyridine); 8.40 (d, J=10 Hz, 1H: CONH at 1); 8.48 (d, J=8.5 Hz, 1H: CONH at 6); 11.67 (s, 1H: OH).

EXAMPLE 16

The process was performed as in Example 1, but starting with 30 cm$^3$ of acetonitrile, 3 g of a crude mixture containing 33 mol% of 5δ-chloromethyl-5δ,5γ-dehydropristinamycin I$_E$, and 1.4 cm$^3$ of N-benzylethanolamine. The reaction mixture was refluxed for 8 hours and then concentrated under reduced pressure at 45° C. (2.7 kPa). The solid was taken up in 50 cm$^3$ of water and 10 cm$^3$ of 2N hydrochloric acid. The aqueous phase was extracted with twice 100 cm$^3$ of ethyl acetate and twice 100 cm$^3$ of diethyl ether, followed by addition of 2 g of sodium bicarbonate. The white precipitate formed was filtered off and then taken up in 50 cm$^3$ of dichloromethane. The solution obtained was washed successively with 3 times 50 cm$^3$ of water and 3 times 50 cm$^3$ of saturated aqueous sodium chloride solution and then dried over magnesium sulphate, filtered, and concentrated to dryness to give 2 g of a white product, which product was purified by chromatography on silica (eluent: 99/1 to 96/4 by volume gradient of dichloromethane/methanol). A solid was thus obtained which was stirred in 60 cm$^3$ of diethyl ether, filtered off, and dried at 40° C. (90 Pa) to give 0.68 g of 5δ-[N-benzyl-N-(2-hydroxyethyl)aminomethyl-5δ,5γ-dehydropristinamycin I$_E$ in the form of a solid melting at 148° C.

0.063 g of methanesulphonic acid was added to this solid dissolved in 10 cm$^3$ of ethyl acetate. The mixture obtained was stirred for 1 hour and then diluted with 10 cm$^3$ of diethyl ether. After stirring overnight, the precipitate was filtered off, washed with twice 5 cm$^3$ of diethyl ether, and then dried under reduced pressure at 20° C. (90 Pa) over phosphorus pentoxide. 0.5 g of 5δ-[N-benzyl-N-(2-hydroxyethyl)] aminomethyl-5δ,5γ-dehydropristinamycin I$_E$ methane-sulphonate was thus obtained in the form is of white crystals melting at 165° C.

$^1$H NMR spectrum (400 MHz, CDCl$_3$): from 0.85 to 1.05 (mt, 1H: 1H of the CH$_2$ at 5β); 0.91 (t, J=7.5 Hz, 3H: CH$_3$ at 2γ); from 1.10 to 1.35 (mt, 2H: 1H of the CH$_2$ at 3β and 1H of the CH$_2$ at 3γ); 1.30 (d, J=7 Hz, 3H: CH$_3$ at 1γ); 1.56 (mt, 1H: the other H of the CH$_2$ at 3γ); 1.65 and 1.72 (2 mts, 1H each: CH$_2$ at 2β); 2.02 (mt, 1H: the other H of the CH$_2$ at 3β); 2.44 (very broad d, J=16 Hz, 1H: the other H of the CH$_2$ at 5β); 2.84 (s, 3H: SO$_2$CH$_3$); from 2.90 to 3.30 (mt, 2H: NCH$_2$); from 2.95 to 3.05 (mt, 1H: 1H of the CH$_2$ at 4β); 2.98 (broad s, 6H: ArN(CH$_3$)$_2$); from 3.10 to 3.25 (mt, 2H: 1H of the CH$_2$ at 3δ and the other H of the CH$_2$ at 4β); 3.18 (s, 3H, NCH$_3$); from 3.35 to 4.00 (2 broad unres. mults, 2H in total: CH$_2$N); from 3.40 to 3.55 (mt, 2H: 1H of the CH$_2$ at 5ε and the other H of the CH$_2$ at 3δ); 3.90 (very broad s, 2H: CH$_2$O); 4.40 and 4.54 (2 mts, 1H each: ArCH$_2$N); 4.54 (mt, 1H: CH at 3α); 4.76 (mt, 1H: CH at 2α); from 4.85 to 4.95 (mt, 1H: the other H of the CH$_2$ at 5ε); 4.87 (broad d, J=10 Hz, 1H: CH at 1α); 5.13 (broad d, J=5 Hz, 1H: CH at 5α); 5.18 (dd, J=9.5 and 5.5 Hz, 1H: CH at 4α; 5.66 (mt, 1H: CH at 6α); from 5.80 to 5.95 (unres. mult., 1H: CH at 5γ); 5.86 (broad q, J=7 Hz, 1H: CH at 1β); 6.53 (d, J=9 Hz, 1H: CONH at 2); from 6.55 to 6.95 (broad unres. mult., 2H: aromatic Hs at 4ε); 6.98 (unres. mult., 2H: aromatic Hs at 4δ); from 7.20 to 7.55 (mt, the 12 Hs corresponding to aromatic Hs at 6α- to the aromatic Hs of the benzyl—to H$_4$ and to H$_5$); 7.73 (unres. mult., 1H: H$_6$); 8.34 (d, J=10 Hz, 1H: CONH at 1); 8.72 (unres. mult., 1H: CONH at 6); from 9.60 to 10.50 (very broad unres. mult., 1H: OH of the methanesulphonate); 11.64 (s, 1H: OH).

EXAMPLE 17

The process was performed as in Example 1, but starting with 80 cm$^3$ of acetonitrile, 8 g of a crude mixture containing 33 mol % of 5δ-chloromethyl-5δ,5γ-dehydropristinamycin I$_E$ and 1.48 g of N-ethyloxycarbonylpiperazine. The reaction mixture was refluxed for 3 hours and then concentrated under reduced pressure at 45° C. (2.7 kPa). The solid was taken up in 200 cm$^3$ of dichloromethane. The solution obtained was washed with twice 100 cm$^3$ of water, the phases were separated after settling had taken place and the organic phase was then dried over magnesium sulphate, filtered and concentrated to dryness to give 7.4 g of a green solid which was purified by 2 flash chromatographies on silica (eluent: 95/5 and then 98/2 by volume dichloromethane/methanol) and then by 2 preparative HPLC chromatographies on 500 g of 20–45 μm silica (eluent: 98/2 and 99/1 dichloromethane/methanol) and finally by preparative HPLC on 450 g of 10 μm C$_8$ silica (eluent: 60/40 by volume water/acetonitrile containing 0.1% trifluoroacetic acid). The fractions containing the expected product were combined, the acetonitrile was removed at 40° C. under reduced pressure (2.7 kPa) and the pH of the aqueous phase was adjusted to 7 by addition of saturated aqueous sodium bicarbonate solution. The precipitate formed was filtered off, washed with 30 cm$^3$ of water, rinsed with twice 30 cm$^3$ of diisopropyl ether and then dried at 40° C. (90 Pa) to give 0.36 g of 5δ-[4-ethyloxycarbonylpiperazin-1-yl]methyl-5δ,5γ-dehydropristinamycin I$_E$ in the form of a white powder melting at about 165° C.

$^1$H NMR spectrum (400 MHz, CDCl$_3$): 0.91 (t, J=7.5 Hz, 3H: CH$_3$ at 2γ); 1.06 (very broad d, J=16 Hz, 1H: 1H of the CH$_2$ at 5β); from 1.15 to 1.35 (mt, 2H: 1H of the CH$_2$ at 3β and 1H of the CH$_2$ at 3γ); 1.25 (t, J=7.5 Hz, 3H: CH$_3$ of the ethyl); 1.31 (d, J=7 Hz, 3H: CH$_3$ at 1γ); 1.55 (mt, 1H: the other H of the CH$_2$ at 3γ); from 1.60 to 1.80 (mt, the 2 Hs corresponding to the CH$_2$ at 2β); 1.98 (mt, 1H: the other H of the CH$_2$ at 3β); from 2.15 to 2.60 (broad unres. mult., 4H: CH$_2$N of the piperazine); 2.46 (dd, J=16 and 5.5 Hz, 1H: the other H of the CH$_2$ at 5β); from 2.85 to 3.05 (mt, 3H: CH$_2$N and 1H of the CH$_2$ at 4β); 2.93 (s, 6H: ArN(CH$_3$)$_2$); from 3.15 to 3.30 (mt, 2H: 1H of the CH$_2$ at 3δ and the other H of the CH$_2$ at 4β); 3.17 (s, 3H: NCH$_3$); from 3.30 to 3.75 (broad unres. mult., 4H: CH$_2$NCO of the piperazine); 3.34 (broad d, J=18 Hz, 1H: 1H of the CH$_2$ at 5ε); 3.46 (mt, 1H: the other H of the CH$_2$ at 3δ); 4.13 (q, J=7.5 Hz, 2H: COOCH$_2$); 4.57 (dd, J=8 and 5.5 Hz, 1H: CH at 3α); 4.77 (mt, 1H: CH at 2α); 4.83 (broad d, J=18 Hz, 1H: the other H of the CH$_2$ at 5ε); 4.87 (dd, J=10 and 1 Hz, 1H: CH at 1α); 5.11 (broad d, J=5.5 Hz, 1H: CH at 5α); 5.21 (dd, J=9 and 6.5 Hz, 1H: CH at 4α); from 5.50 to 5.60 (mt, 1H: CH at 5γ); 5.53 (d, J=7.5 Hz, 1H: CH at 6α); 5.88 (resolved q, J=7 and 1 Hz, 1H: CH at 1β); from 6.50 to 6.60 (mt, 1H: CONH at 2); 6.58 (d, J=8 Hz, 2H: aromatic Hs at 4ε); 6.90 (d, J=8 Hz, 2H: aromatic Hs at 4δ); from 7.20 to 7.40 (mt: the 7 Hs corresponding to the aromatic Hs at 6α- to H$_4$ and to H$_5$); 7.72 (dd, J=4 and 1.5 Hz, 1H: H$_6$); 8.38 (d, J=10 Hz, 1H: CONH at 1); 8.51 (d, J=7.5 Hz, 1H: CONH at 6); 11.66 (s, 1H: OH).

EXAMPLE 18

The process was performed as in Example 1, but starting with 30 cm$^3$ of acetonitrile, 3 g of a crude mixture containing 33 mol % of 5δ-chloromethyl-5δ,5γ-dehydropristinamycin I$_E$, and 1.8 g of 1-(2-furoyl)piperazine. The reaction mixture was refluxed for 24 hours and then concentrated under reduced pressure at 45° C. (2.7 kPa). The solid obtained was taken up in 50 cm$^3$ of water and 10 cm$^3$ of 2N hydrochloric acid. The solution obtained was extracted with 3 times 100 cm$^3$ of ethyl acetate and twice 100 cm$^3$ of diethyl ether, followed by addition of 2 g of sodium bicarbonate. The white precipitate formed was filtered off, washed with 6 times 20 cm$^3$ of water ,and then dissolved in 80 cm$^3$ of dichloromethane. The solution obtained was washed with 3 times 50 cm$^3$ of water and twice 50 cm$^3$ of saturated aqueous sodium chloride solution, and then concentrated to dryness to give 2.15 g of a solid which was chromatographed on silica (eluent: 100/0 to 97/3 by volume gradient of dichloromethane/methanol). A solid was obtained, which was taken up in 80 cm$^3$ of diethyl ether, filtered off, rinsed with 3 times 10 cm$^3$ of diethyl ether and then dried at 40° C. (90 Pa) to give 0.73 g of 5δ-[4-(2-furoyl)piperazin-1-yl]methyl-5δ,5γ-dehydropristinamycin I$_E$ in the form of off-white crystals melting at about 148° C.

$^1$H NMR spectrum (400 MHz, CDCl$_3$): 0.91 (t, J=7.5 Hz, 3H: CH$_3$ at 2γ); 1.08 (very broad d, J=16 Hz, 1H: 1H of the CH$_2$ at 5β); 1.25 (mt, 2H: 1H of the CH$_2$ at 3β and 1H of the CH$_2$ at 3γ); 1.30 (d, J=7 Hz, 3H: CH$_3$ at 1γ); 1.56 (mt; 1H: the other H of the CH$_2$ at 3γ); from 1.60 to 1.80 (mt, the 2 Hs corresponding to the CH$_2$ at 2β); 2.00 (mt, 1H: the other H of the CH$_2$ at 3β); from 2.25 to 2.55 (broad unres. mult., 4H: the 2 CH$_2$Ns of the piperazine); 2.46 (dd, J=16 and 5 Hz, 1H: the other H of the CH$_2$ at 5β); 2.88 (s, 2H: CH$_2$N); 2.93 (s, 6H: ArN(CH$_3$)$_2$); 2.98 (dd, J=14 and 6.5 Hz, 1H: 1H of the CH$_2$ at 4β); from 3.15 to 3.30 (mt, 2H: 1H of the CH$_2$ at 3δ and the other H of the CH$_2$ at 4β); 3.19 (s, 3H: NCH$_3$); 3.34 (broad d, J=18 Hz, 1H: 1H of the CH$_2$ at 5ε); 3.46 (mt, 1H: the other H of the CH$_2$ at 3δ); from 3.50 to 4.10 (very broad unres. mult., 4H: the 2 CH$_2$NCOs of the piperazine); 4.58 (dd, J=8 and 5.5 Hz, 1H: CH at 3α); 4.77 (mt, 1H: CH at 2α); 4.84 (broad d, J=18 Hz, 1H: the other H of the CH$_2$ at 5ε); 4.87 (dd, J=10 and 1 Hz, 1H: CH at 1α); 5.12 (broad d, J=5.5 Hz, 1H: CH at 5α); 5.24 (dd, J=9.5 and 6.5 Hz, 1H: CH at 4α); 5.50 (mt, 1H: CH at 5γ); 5.53 (d, J=8 Hz, 1H: CH at 6α); 5.87 (resolved q, J=7 and 1 Hz, 1H: CH at 1β); 6.46 (dd, J=3 and 2 Hz, 1H: H at 4 of the furan); from 6.55 to 6.65 (mt, 1H: CONH at 2); 6.58 (d, J=8 Hz, 2H: aromatic Hs at 4ε); 6.92 (d, J=8 Hz, 2H: aromatic Hs at 4δ); 6.98 (dd, J=3 Hz, 1H: H at 3 of the furan); from 7.20 to 7.40 (mt: the 7 Hs corresponding to the aromatic Hs at 6α- to H$_4$ and to H$_5$); 7.48 (dd, J=2 Hz, 1H: H at 5 of the furan); 7.73 (dd, J=4 and 1.5 Hz, 1H: H$_6$); 8.41 (d, J=10 Hz, 1H: CONH at 1); 8.53 (d, J=8 Hz, 1H: CONH at 6); 11.67 (broad s, 1H: OH).

EXAMPLE 19

The process was performed as in Example 1, but starting with 60 m$^3$ of acetonitrile, 6 g of a crude mixture containing 33 mol % of 5δ-chloromethyl-5δ,5γ-dehydropristinamycin I$_E$ and 4.1 cm$^3$ of N'-benzyl-N,N-dimethylethylenediamine. The reaction mixture was refluxed for 15 hours and then concentrated to dryness under reduced pressure at 45° C. (2.7 kPa). The solid obtained was taken up with 100 cm$^3$ of water and with 2N hydrochloric acid solution so as to obtain a pH of 1. The aqueous phase was extracted with twice 100 cm$^3$ of diethyl ether and twice 100 cm$^3$ of ethyl acetate, adjusted to pH 7 by addition of saturated aqueous sodium bicarbonate solution, and then extracted with twice 100 cm$^3$ of dichloromethane. The organic phase was dried over sodium sulphate, filtered, and concentrated to dryness under reduced pressure to give 7.4 g of a solid which was chromatographed on silica (eluent: 98/2 by volume dichloromethane/methanol). A solid was obtained, which was stirred in 50 cm³ of ether and then filtered off and dried to give 0.64 g of a white solid, which was taken up in 20 cm³ of water and in hydrochloric acid solution so as to obtain a pH of 1. This mixture was extracted with twice 20 cm³ of diethyl ether. Saturated sodium bicarbonate solution was added to the aqueous phase and the precipitate was filtered off and dried at 20° C. (90 Pa) over $P_2O_5$ to give 0.14 g of 5δ-N-benzyl-N-(2-dimethylaminoethyl)aminomethyl-5δ,5γ-dehydropristinamycin $I_E$ in the form of a white powder melting at 182° C.

¹H NMR spectrum (400 MHz, CDCl₃): 0.92 (t, J=7.5 Hz, 3H: CH₃ at 2γ); 1.06 (very broad d, J=16 Hz, 1H: 1H of the CH₂ at 5β), from 1.20 to 1.35 (mt, 2H: 1H of the CH₂ at 3β and 1H of the CH₂ at 3γ); 1.29 (d, J=7 Hz, 3H: CH₃ at 1γ); from 1.50 to 1.85 (mt: the 3 Hs corresponding to the other H of the CH₂ at 3γ and to CH₂ at 2β); 2.02 (mt, 1H: the other H of the CH₂ at 3β); 2.33 (unres. mult., 6H: the 2 NCH₃s of the dimethylamine); 2.43 (broad dd, J=16 and 5 Hz, 1H: the other H of the CH₂ at 5β); 2.59 (unres. mult., 4H: NCH₂CH₂N); from 2.85 to 3.05 (mt, 1H: 1H of the CH₂ at 4β); 2.91 (s, 6H: ArN(CH₃)₂); 3.00 (s, 2H: CH₂N); from 3.15 to 3.30 (mt, 2H: 1H of the CH₂ at 3δ and the other H of the CH₂ at 4β); 3.17 (s, 3H: NCH₃); 3.33 (broad d, J=18 Hz, 1H: 1H of the CH₂ at 5ε); 3.46 (mt, 1H: the other H of the CH₂ at 3δ); 3.55 (s, 2H: ArCH₂N); 4.57 (dd, J=8 and 6 Hz, 1H: CH at 3α); 4.78 (mt, 1H: CH at 2ε); 4.87 (broad d, J=18 Hz, 1H: the other H of the CH₂ at 5ε); 4.87 (dd, J=10 and 1 Hz, 1H: CH at 1α); 5.13 (broad d, J=5 Hz, 1H: CH at 5α); 5.24 (dd, J=10 and 6 Hz, 1H: CH at 4α); 5.46 (d, J=8 Hz, 1H: CH at 6α); 5.55 (mt, 1H: CH at 5γ); 5.85 (resolved q, J=7 and 1 Hz, 1H: CH at 1β); 6.54 (d, J=8 Hz; 2H: aromatic Hs at 4ε); 6.57 (d, J=10 Hz, 1H: CONH at 2); 6.88 (d, J=8 Hz, 2H: aromatic Hs at 4δ); from 7.15 to 7.40 (mt: the 7 Hs corresponding to the aromatic Hs at 6α- to H₄ and to H₅); 7.71 (dd, J=4 and 1.5 Hz, 1H: H₆); 8.38 (d, J=10 Hz, 1H: CONH at 1); 8.53 (d, J=8 Hz, 1H: CONH at 6); 11.66 (unres. mult., 1H: OH).

EXAMPLE 20

The process was performed as in Example 1, but starting with 100 cm³ of acetonitrile, 20 g of a crude mixture containing 33 mol % of 5δ-chloromethyl-5δ,5γ-dehydropristinamycin $I_E$, 4.5 g of 4-phenyl-1,2,3,6-tetrahydropyridine hydrochloride and 3.25 cm³ of triethylamine. The reaction mixture was refluxed for 1.5 hours and then concentrated to dryness under reduced pressure at 45° C. (2.7 kPa). The solid obtained was taken up in 100 cm³ of water and then filtered off, washed with 20 cm³ of water, and dried under reduced pressure to give 26 g of solid. This solid was purified by chromatography on silica (eluent: 97/3 by volume dichloromethane/methanol) and then by preparative HPLC on 450 g of 10 μm C₈ silica (eluent: 65/35 by volume water/acetonitrile containing 0.1% trifluoroacetic acid). The fractions containing the expected product were combined, the acetonitrile was removed at 40° C. under reduced pressure (2.7 kPa) and the pH of the aqueous solution was adjusted to 7–8 by addition of saturated aqueous sodium bicarbonate solution. The precipitate formed was filtered off, washed with 20 cm³ of water and dried under reduced pressure at 40° C. (90 Pa) to give 0.47 g of 5δ-[1-(4-phenyl)-1,2,3,6-tetrahydropyridyl]methyl-5δ,5γ-dehydropristinamycin $I_E$ in the form of a white solid melting at 154° C.

¹H NMR spectrum (400 MHz, CDCl₃): 0.92 (t, J=7.5 Hz, 3H: CH₃ at 2γ); from 1.00 to 1.15 (broad unres. mult., 1H: 1H of the CH₂ at 5); 1.22 (mt, 2H: 1H of the CH₂ at 3β and 1H of the CH₂ at 3γ); 1.32 (d, J=7 Hz, 3H: CH₃ at 1γ); 1.54 (mt, 1H: the other H of the CH₂ at 3γ); from 1.60 to 1.85 (mt, the 2 Hs corresponding to the CH₂ at 2β); 1.99 (mt, 1H: the other H of the CH₂ at 3β); from 2.40 to 2.80 (mt, 5H: NCH₂CH₂ of the 1,2,3,6-tetrahydropyridine and the other H of the CH₂ at 5β); from 2.90 to 3.30 (mt, 7H: CH₂N—CH₂ at 4β-NCH₂ of the 1,2,3,6-tetrahydropyridine and 1H of the CH₂ at 3β); 2.95 (s, 6H: ArN(CH₃)₂); 3.17 (s, 3H: NCH₃); from 3.35 to 3.55 (mt, 2H: 1H of the CH₂ at 5ε and the other H of the CH₂ at 3δ); 4.57 (dd, J=8 and 5.5 Hz, 1H: CH at 3α); 4.77 (mt, 1H: CH at 2α); from 4.80 to 4.95 (mt, 1H: the other H of the CH₂ at 5ε); 4.87 (dd, J=10 and 1 Hz, 1H: CH at 1α); 5.14 (d, J=5.5 Hz, 1H: CH at 5α); 5.22 (mt, 1H: CH at 4α); from 5.50 to 5.65 (unres. mult., 1H: CH at 5γ); 5.57 (d, J=8 Hz, 1H: CH at 6α); 5.88 (resolved q, J=7 and 1 Hz, 1H: CH at 5β); 6.06 (mt, 1H: CH═ of the 1,2,3,6-tetrahydropyridine); 6.56 (d, J=9 Hz, CONH at 2); 6.60 (d, J=8 Hz, 2H: aromatic Hs at 4ε); 6.93 (d, J=8 Hz, 2H: aromatic Hs at 4δ); from 7.20 to 7.45 (mt: the 12 Hs corresponding to the aromatic Hs at 6α- to the aromatic Hs of the phenyl—to H₄ and to H₅); 7.73 (dd, J=4 and 1 Hz, 1H: H₆); 8.39 (d, J=10 Hz, 1H: CONH at 1); 8.49 (unres. mult., 1H: CONH at 6); 11.66 (s, 1H: OH).

EXAMPLE 21

The process was performed as in Example 1, but starting with 30 cm³ of acetonitrile, 3 g of a crude mixture containing 33 mol % of 5δ-chloromethyl-5δ,5γ-dehydropristinamycin $I_E$ and 1.9 g of 4-benzyl-4-hydroxypiperidine. The reaction mixture was refluxed for 20 hours and then concentrated to dryness under reduced pressure at 45° C. (2.7 kPa). The solid obtained was taken up in 50 cm³ of water and 10 cm³ of 2N hydrochloric acid. The solution obtained was extracted successively with 4 times 50 cm³ of ethyl acetate and with twice 50 cm³ of diethyl ether, adjusted to pH 7–8 by addition of 2 g of sodium bicarbonate, and then extracted with 3 times 100 cm³ of dichloromethane. The organic phase was separated out after settling had taken place, dried over sodium sulphate, filtered, and concentrated to dryness at 45° C. under reduced pressure (2.7 kPa) to give 2.6 g of a solid, which was chromatographed on silica (eluent: 99.5/0.5 and then 90/10 by volume gradient of dichloromethane/methanol). A solid was obtained, which was stirred in 50 cm³ of diisopropyl ether and then filtered off and dried under reduced pressure at 40° C. (90 Pa) to give 0.2 g of 5δ-(4-benzyl-4-hydroxypiperidinomethyl)-5δ,5γ-dehydropristinamycin $I_E$ in the form of off-white crystals melting at 172° C.

¹H NMR spectrum (400 MHz, CDCl₃): 0.92 (t, J=7.5 Hz, 3H: CH₃ at 2γ); 1.03 (very broad d, J=16 Hz, 1H: 1H of the CH₂ at 5β); from 1.15 to 1.35 (mt, 2H: 1H of the CH₂ at 3β and 1H of the CH₂ at 3γ); 1.30 (d, J=7 Hz, 3H: CH₃ at 1γ); from 1.50 to 1.90 (mt: the 3 Hs corresponding to the other H of the CH₂ at 3γ and to the CH₂ at 2β); from 1.50 to 1.90—from 2.10 to 2.35 and from 2.50 to 2.65 (3 series of mt: the 10 Hs corresponding to the NCH₂CH₂ of the piperidine and CH₂Ar); 2.00 (mt, 1H: the other H of the CH₂ at 3β); 2.45 (mt, 1H: the other H of the CH₂ at 5β); from 2.75 to 3.05 (mt, 3H: CH₂N and 1H of the CH₂ at 4β); 2.93 (s, 6H: ArN(CH₃)₂); from 3.15 to 3.30 (mt, 2H: the other H of the CH₂ at 4β and 1H of the CH₂ at 3δ); 3.18 (s, 3H: NCH₃); 3.30 (broad d, J=18 Hz, 1H: 1H of CH₂ at 5ε); 3.47 (mt, 1H: the other H of the CH₂ at 3δ); 4.58 (dd, J=8 and 5.5 Hz, 1H: CH at 3α); 4.78 (mt, 1H: CH at 2α); from 4.80 to 4.90 (mt, 1H: the other H of the CH₂ at 5ε); 4.87 (broad d, J=10 Hz, 1H: CH at 1α); 5.11 (broad d, J=5.5 Hz, 1H: CH at 5α); 5.22

(dd, J=9 and 7 Hz, 1H: CH at 4α); 5.47 (mt, 1H: CH at 5γ); 5.54 (d, J=8 Hz, 1H: CH at 6α); 5.87 (broad q, J=7 Hz, 1H: CH at 1β); from 6.55 to 6.65 (mt, 1H: CONH at 2); 6.58 (d, J=8 Hz, 2H: aromatic Hs at 4ε); 6.91 (d, J=8 Hz, 2H: aromatic Hs at 4δ); from 7.10 to 7.40 (mt: the 12 Hs corresponding to the aromatic Hs at 6α- to the aromatic Hs of the phenyl—to $H_4$ and to $H_5$); 7.72 (broad d, J=4 Hz, 1H: $H_6$); 8.39 (d, J=10 Hz, 1H: CONH at 1); 8.46 (d, J=8 Hz, 1H: CONH at 6); 11.67 (s, 1H: OH).

EXAMPLE 22

The process was performed as in Example 1, but starting with 30 cm³ of acetonitrile, 3 g of a crude mixture containing 33 mol % of 5δ-chloromethyl-5δ,5γ-dehydropristinamycin $I_E$ and (5δR)-5δ-methylene-5γ-chloropristinamycin $I_E$ (in a 33/67 proportion) and 1.25 g of N-allylcyclopentylamine. The reaction mixture was refluxed for 28 hours and then concentrated to dryness under reduced pressure at 45° C. (2.7 kPa). The solid obtained was taken up in 50 cm³ of water and 10 cm³ of 2N hydrochloric acid. The solution obtained was extracted successively with 4 times 50 cm³ of ethyl acetate and with twice 50 cm³ of diethyl ether and was then adjusted to pH 8 by addition of 2 g of sodium bicarbonate. The precipitate formed was filtered off, washed with water to remove any remaining mineral salts, and then dissolved in 50 cm³ of dichloromethane. The resulting solution was washed with 4 times 50 cm³ of water and with twice 50 cm³ of saturated aqueous sodium chloride solution, and then dried over sodium sulphate, filtered, and concentrated to dryness at 45° C. under reduced pressure (2.7 kPa). 2.3 g of a solid were thus obtained, which product was chromatographed on silica (eluent: 100/0 and then 98/2 by volume gradient of dichloromethane/methanol). A solid was obtained, which was stirred in 50 cm³ of diisopropyl ether, filtered off, washed with 3 times 10 cm³ of diisopropyl ether, and then dried under reduced pressure at 20° C. (90 Pa) to give 0.59 g of 5δ-(N-allyl-N-cyclopentyl)aminomethyl-5δ,5γ-dehydropristinamycin $I_E$ in the form of white crystals melting at 140° C.

¹H NMR spectrum (400 MHz, CDCl₃): 0.93 (t, J=7.5 Hz, 3H: $CH_3$ at 2γ); 1.07 (very broad d, J=16 Hz, 1H: 1H of the $CH_2$ at 5β); from 1.15 to 1.35 (mt, 2H: 1H of the $CH_2$ at 3β and 1H of the $CH_2$ at 3γ); 1.31 (d, J=7 Hz, 3H: $CH_3$ at 1γ); from 1.35 to 1.85 (mt: the 11 Hs corresponding to the other H of the $CH_2$ at 3γ- to the $CH_2$s of the cyclopentane and to the $CH_2$ at 2β); 2.00 (mt, 1H: the other H of the $CH_2$ at 3β); 2.47 (mt, 1H: the other H of the $CH_2$ at 5β); from 2.85 to 3.05 (mt, 3H: 1H of the $CH_2$ at 4β-$CH_2$N); 2.93 (s, 6H: ArN($CH_3$)₂); from 3.05 to 3.20 (mt, 3H: NCH and $NCH_2$ of the allyl); from 3.15 to 3.45 (mt, 3H: 1H of the $CH_2$ at 3δ- the other H of the $CH_2$ at 4β and 1H of the $CH_2$ at 5ε); 3.17 (s, 3H: $NCH_3$); 3.47 (mt, 1H: the other H of the $CH_2$ at 3δ); 4.58 (dd, J=8.5 and 6 Hz, 1H: CH at 3α); 4.78 (mt, 1H: CH at 2α); from 4.80 to 4.95 (mt, 1H: the other H of the $CH_2$ at 5ε); 4.86 (broad d, J=10 Hz, 1H: CH at 1α); from 5.00 to 5.30 (mt, 4H: =$CH_2$ of the allyl—CH at 5α and CH at 4α); 5.47 (mt, 1H: CH at 5γ); 5.55 (d, J=8 Hz, 1H: CH at 6α); from 5.80 to 5.95 (mt, 21H: CH= of the allyl and CH at 1β); 6.56 (d, J=10 Hz, 1H: CONH at 2); 6.60 (d, J=8 Hz, 2H: aromatic Hs at 4ε); 6.91 (d, J=8 Hz, 2H: aromatic Hs at 4δ); from 7.20 to 7.40 (mt: the 7 Hs corresponding to the aromatic Hs at 6α- to $H_4$ and to $H_5$); 7.73 (dd, J=4 and 1 Hz, 1H: $H_6$); from 8.35 to 8.45 (mt, 2H: CONH at 1 and CONH at 6); 11.66 (s, 1H: OH).

EXAMPLE 23

Working as in Example 1, but starting with a crude mixture containing 5δ-chloromethyl-5δ,5γ-dehydro-4ε-chloropristinamycin $I_E$, 0.5 g of 5δ-morpholinomethyl-5δ,5γ-dehydro-4ε-chloropristinamycin $I_E$ was prepared in the form of a white solid melting at 150° C.

¹H NMR spectrum (400 MHz, CDCl₃): 0.92 (t, J=7.5 Hz, 3H: $CH_3$ at 2γ); from 1.10 to 1.35 (mt, 3H: 1H of the $CH_2$ at 5β-1H of the $CH_2$ at 3β and 1H of the $CH_2$ at 3γ); 1.31 (d, J=7 Hz, 3H: $CH_3$ at 1γ); 1.57 (mt, 1H: the other H of the $CH_2$ at 3γ); 1.67 and 1.75 (2 mts, 1H each: $CH_2$ at 2β); 1.99 (mt, 1H: the other H of the $CH_2$ at 3β); 2.35 (unres. mult., 4H: $NCH_2$ of the morpholine); 2.57 (broad dd, J=16 and 5 Hz, 1H: the other H of the $CH_2$ at 5β); 2.80 (s. 6H: ArN($CH_3$)₂); 2.88 (limiting AB, J=14 Hz, 2H: $CH_2$N); 3.02 (dd, J=14 and 7.5 Hz, 1H: 1H of the $CH_2$ at 4β); from 3.10 to 3.25 (mt, 1H: the other H of the $CH_2$ at 4β); 3.14 (s, 3H, $NCH_3$); 3.28 (mt, 1H: 1H of the $CH_2$ at 3δ); 3.36 (broad d, J=18 Hz, 1H: 1H of the $CH_2$ at 5ε); 3.48 (mt, 1H: the other H of the $CH_2$ at 3δ); 3.70 (mt, 4H: $CH_2$O of the morpholine); 4.56 (dd, J=8 and 6 Hz, 1H: CH at 3α); from 4.75 to 4.85 (mt, 2H: CH at 2α and the other H of the $CH_2$ at 5ε); 4.87 (dd, J=10 and 1 Hz, 1H: CH at 1α); 5.13 (d, J=5 Hz, 1H: CH at 5α); 5.26 (dd, J=8 and 7.5 Hz, 1H: CH at 4α); 5.50 (d, J=8 Hz, 1H: CH at 6α); 5.55 (mt, 1H: CH at 5γ); 5.88 (resolved q, J=7 and 1 Hz, 1H: CH at 1β); 6.56 (d, J=9.5 Hz, 1H: CONH at 2); 6.87 (limiting AB, 2H: aromatic H at 4ε and aromatic H at 4δ and para to the Cl); 7.09 (d, J=2 Hz, 1H: aromatic H at 4δ and ortho to the Cl); from 7.25 to 7.40 (mt: the 7 Hs corresponding to the aromatic Hs at 6α- to $H_4$ and to $H_5$); 7.69 (dd, J=4 and 2 Hz, 1H: $H_6$); 8.33 (d, J=10 Hz, 1H: CONH at 1); 8.46 (d, J=8 Hz, 1H: CONH at 6); 11.68 (s, 1H: OH).

5δ-Chloromethyl-5δ,5γ-dehydro-4ε-chloropristinamycin was prepared from 4ε-chloro-5δ-methylenepristinamycin $I_A$ by analogy with the method described in Example 1.

4ε-Chloro-5δ-methylenepristinamycin $I_A$ was obtained in the following way:

1.9 g of N-chlorosuccinimide were added, under an argon atmosphere, to 11.4 g of 5δ-methylenepristinamycin $I_A$ dissolved in 120 cm³ of acetonitrile. The mixture was refluxed for 2 hours, followed by addition of a further 346 mg of N-chlorosuccinimide. After refluxing for a further 1.5 hours and stirring for 18 hours at 20° C., the reaction mixture was concentrated to dryness under reduced pressure (2.7 kPa) at 30° C. The solid obtained was stirred for 4 hours in 250 cm³ of diethyl ether, filtered off, rinsed, and then dried in a fume cupboard at 20° C. to give 11.7 g of 4ε-chloro-5δ-methylenepristinamycin $I_A$ in the form of a pink powder which was used without purification.

EXAMPLE 24

The process was performed as in Example 1, but starting with a crude mixture containing 5δ-chloromethyl-5δ,5γ-dehydro-4ε-chloropristinamycin $I_E$, to give 0.25 g of 5δ-piperidinomethyl-5δ,5γ-dehydro-4ε-chloropristinamycin $I_E$ in the form of a white solid which decomposed at about 160° C.

¹H NMR spectrum (500 MHz, CDCl₃): 0.91 (t, J=7.5 Hz, 3H: $CH_3$ at 2γ); from 1.10 to 1.35 (mt, 3H: 1H of the $CH_2$ at 5β-1H of the $CH_2$ at 3β and 1H of the $CH_2$ at 3γ); 1.30 (d, J=7 Hz, 3H: $CH_3$ at 1γ); from 1.35 to 1.75 (mt, the 8 Hs corresponding to the other H of the $CH_2$ at 3γ- to the $CH_2CH_2CH_2$s of the piperidine and to 1H of the $CH_2$ at 2β); 1.74 (mt, 1H: the other H of the $CH_2$ at 2β); 1.98 (mt, 1H: the other H of the $CH_2$ at 3β); 2.27 (unres. mult., 4H: $NCH_2$ of the piperidine); from 2.50 to 2.65 (mt, 1H: the other H of the $CH_2$ at 5β); 2.78 (s, 6H: ArN($CH_3$)₂); 2.80 (s, 2H: $CH_2$N); 3.01 (mt, 1H: 1H of the $CH_2$ at 4); from 3.10 to 3.25

(mt, 1H: the other H of the CH$_2$ at 4β); 3.14 (s, 3H: NCH$_3$); 3.26 (mt, 1H: 1H of the CH$_2$ at 3δ); 3.36 (mt, 1H: 1H of the CH$_2$ at 5ε); 3.46 (mt, 1H: the other H of the CH$_2$ at 3δ); 4.56 (dd, J=7 and 6 Hz, 1H: CH at 3α); from 4.70 to 4.85 (mt, 2H: CH at 2α and the other H of the CH$_2$ at 5ε); 4.86 (broad d, J=10 Hz, 1H: CH at 1α); 5.12 (d, J=5 Hz, 1H: CH at 5α); 5.25 (mt, 1H: CH at 4α); from 5.45 to 5.55 (mt, 2H: CH at 5γ and CH at 6α); 5.87 (broad q, J=7 Hz, 1H: CH at 1β); 6.55 (d, J=9 Hz, 1H: CONH at 2); 6.86 (mt, 2H: aromatic H at 4ε and aromatic H at 4δ para to the Cl); 7.09 (broad s, 1H: aromatic H at 4δ ortho to the Cl); from 7.20 to 7.40 (mt, the 7 Hs corresponding to the aromatic Hs at 6α- to H$_4$ and to H$_5$); 7.69 (mt, 1H: H$_6$); from 8.30 to 8.45 (mt, 2H: CONH at 1 and CONH at 6); 11.68 (s, 1H: OH).

EXAMPLE 25

The process was performed as in Example 1, but starting with a crude mixture containing 5δ-chloromethyl-5δ,5γ-dehydro-4ε-chloropristinamycin I$_E$ to give 0.35 g of 5δ-(2,6-dimethylmorpholino)methyl-5δ,5γ-dehydro-4ε-chloropristinamycin I$_E$, in the form of a white solid melting at 170° C.

$^1$H NMR spectrum (400 MHz, CDCl$_3$): We observed a mixture of two cis and trans diastereoisomers on the morpholine, as well as the presence of tiny traces of other unidentified pristinamycins and of conformers. 0.92 (t, J=7.5 Hz, 3H: CH$_3$ at 2γ); from 1.05 to 1.40 (mt, 3H: 1H of the CH$_2$ at 5β-1H of the CH$_2$ at 3β and 1H of the CH$_2$ at 3γ); 1.15 and 1.19 (2d, J=7 Hz, 3H each: CH$_3$ of the 2,6-dimethylmorpholine); 1.31 (d, J=7 Hz, 3H: CH$_3$ at 1γ); from 1.50 to 1.75 (mt: the 4 Hs corresponding to the other H of the CH$_2$ at 3γ- to 1H of the CH$_2$ at 2β and to 2H of the NCH$_2$s of the 2,6-dimethylmorpholine); 1.75 (mt, 1H: the other H of the CH$_2$ at 2β); 2.00 (mt, 1H: the other H of the CH$_2$ at 3β); 2.57 (broad dd, J=16 and 5.5 Hz, 1H: the other H of the CH$_2$ at 5β); 2.66 (mt, 2H: the other 2 Hs of the NCH$_2$ of the 2,6-dimethylmorpholine); 2.80 (s, 6H: ArN(CH$_3$)$_2$; 2.85 (broad s, 2H: CH$_2$N); 3.03 (dd, J=14 and 7 Hz, 1H: 1H of the CH$_2$ at 4β), from 3.10 to 3.25 (mt, 1H: the other H of the CH$_2$ at 4β); 3.16 (s, 3H: NCH$_3$); 3.30 (mt, 1H: 1H of the CH$_2$ at 3δ); 3.35 (broad d, J=18 Hz, 1H: 1H of the CH$_2$ at 5ε); 3.48 (mt, 1H: the other H of the CH$_2$ at 3δ); 3.59 and 3.69 (2 mts, 1H each: CHO of the morpholine); 4.58 (dd, J=7 and 5 Hz, 1H: CH at 3α); from 4.70 to 4.85 (mt, 2H: CH at 2α and the other H of the CH$_2$ at 5ε); 4.87 (broad d, J=10 Hz, 1H: CH at 1α); 5.13 (d, J=5.5 Hz, 1H: CH at 5α); 5.27 (mt, 1H: CH at 4α); 5.51 (d, J=7.5 Hz, 1H: CH at 6α); 5.53 (mt, 1H: CH at 5γ); 5.88 (broad q, J=7 Hz, 1H: CH at 1β); 6.57 (d, J=9.5 Hz, 1H: CONH at 2); 6.87 (mt, 2H: aromatic H at 4ε and aromatic H at 4δ para to the Cl); 7.11 (broad s, 1H: aromatic H at 4δ ortho to the Cl); from 7.20 to 7.40 (mt: the 7 Hs corresponding to the aromatic Hs at 6α- to H$_4$ and to H$_5$); 7.70 (mt, 1H; H$_6$); 8.35 (d, J=10 Hz, 1H: CONH at 1); 8.46 (d, J=8 Hz, 1H: CONH at 6); 11.68 (s, 1H: OH).

EXAMPLE 26

The process was performed as in Example 1, but starting with a crude mixture containing 5δ-chloromethyl-5δ,5γ-dehydro-4ε-chloropristinamycin I$_E$. 0.46 g of 5δ-N,N-dipropylaminomethyl-5δ,5γ-dehydro-4ε-chloropristinamycin I$_E$ was thus obtained in the form of a yellow solid melting at 139° C.

$^1$H NMR spectrum (400 MHz, CDCl$_3$): from 0.85 to 0.95 (mt, 9H: CH$_3$ at 2γ and CH$_3$ of the dipropylamine); 1.14 (very broad d, J=16 Hz, 1H: 1H of the CH$_2$ at 5β); from 1.20 to 1.35 (mt, 2H: 1H of the CH$_2$ at 3β and 1H of the CH$_2$ at 3γ); 1.30 (d, J=7 Hz, 3H: CH$_3$ at 1γ); 1.44 (mt, 4H: central CH$_2$s of the dipropylamine); 1.57 (mt: 1H corresponding to the other H of the CH$_2$ at 3γ); from 1.60 to 1.80 (2 mts: the 2 Hs corresponding to the CH$_2$ at 2β); 1.98 (mt, 1H: the other H of the CH$_2$ at 3β); from 2.15 to 2.40 (mt, 4H: NCH$_2$ of the dipropylamine); 2.56 (broad dd, J=16 and 5.5 Hz, 1H: the other H of the CH$_2$ at 5β); 2.78 (s, 6H: ArN(CH$_3$)$_2$); 2.84 and 2.98 (2d, J=13 Hz, 1H each: CH$_2$N); 3.02 (dd, J=14 and 7 Hz, 1H: 1H of the CH$_2$ at 4β); from 3.15 to 3.30 (mt, 2H: 1H of the CH$_2$ at 3δ and the other H of the CH$_2$ at 4β); 3.15 (s, 3H: NCH$_3$); 3.38 (broad d, J=18 Hz, 1H: 1H of the CH$_2$ at 5ε); 3.47 (mt, 1H: the other H of the CH$_2$ at 3δ); 4.55 (dd, J=8 and 5.5 Hz, 1H: CH at 3α); from 4.70 to 4.85 (mt, 2H: CH at 2α and the other H of the CH$_2$ at 5ε); 4.88 (dd, J=10 and 1 Hz, 1H: CH at 1α); 5.14 (broad d, J=5 Hz, 1H: CH at 5α); 5.27 (dd, J=7.5 and 7 Hz, 1H: CH at 4α); 5.49 (mt, 1H: CH at 5γ); 5.54 (d, J=8 Hz, 1H: CH at 6α); 5.88 (resolved q, J=7 and 1 Hz, 1H: CH at 1β); 6.57 (d, J=9.5 Hz, 1H: CONH at 2); 6.86 (d, J=8 Hz, 1H: aromatic H at 4ε); 6.89 (dd, J=8 and 1.5 Hz, 1H: aromatic H at 4δ para to the Cl); 7.11 (d, J=1.5 Hz, 1H: aromatic H at 4δ ortho to the Cl); from 7.20 to 7.40 (mt: the 7 Hs corresponding to the aromatic Hs at 6α- to H$_4$ and to H$_5$); 7.67 (mt, 1H: H$_6$); 8.34 (d, J=10 Hz, 1H: CONH at 1); 8.40 (d, J=8 Hz, 1H: CONH at 6); 11.68 (unres. mult., 1H: OH).

EXAMPLE 27

The process was performed as in Example 1, but starting with a crude mixture containing 5δ-chloromethyl-4ζ-methylamino-4ζ-dedimethylamino-5δ,5γ-dehydropristinamycin I$_E$ 0.5 g of 5δ-morpholinomethyl-4ζ-methylamino-4ζ-dedimethylamino-5δ,5γ-dehydropristinamycin I$_E$ was obtained in the form of a yellow solid melting 173° C.

$^1$H NMR spectrum (400 MHz, CDCl$_3$): 0.91 (t, J=7.5 Hz, 3H: CH$_3$ at 2γ); from 1.15 to 1.40 (mt, 2H: 1H of the CH$_2$ at 3β and 1H of the CH$_2$ at 3γ); 1.16 (very broad d, J=16.5 Hz, 1H: 1H of the CH$_2$ at 5β); 1.31 (d, J=7 Hz, 3H: CH$_3$ at 1γ); 1.56 (mt, 1H: the other H of the CH$_2$ at 3γ); from 1.60 to 1.80 (mt: the 2 Hs corresponding to the CH$_2$ at 2β); 2.00 (mt, 1H: the other H of the CH$_2$ at 3β); 2.35 (unres. mult., 4H: NCH$_2$ of the morpholine); 2.49 (broad dd, J=16.5 and 5 Hz, 1H: the other H of the CH$_2$ at 5β); 2.84 and 2.86 (2s, 5H in total: ArNCH$_3$ and CH$_2$N); 2.97 (dd, J=14 and 6.5 Hz, 1H: 1H of the CH$_2$ at 4β); from 3.10 to 3.20 (mt, 1H: the other H of the CH$_2$ at 4β); 3.17 (s, 3H: NCH$_3$); 3.26 (mt, 1H: 1H of the CH$_2$ at 3δ); 3.33 (broad d, J=18 Hz, 1H: 1H of the CH$_2$ at 5ε); 3.47 (mt, 1H: the other H of the CH$_2$ at 3δ); 3.70 (mt, 4H: CH$_2$O of the morpholine); 4.56 (dd, J=8 and 5.5 Hz, 1H: CH at 3α); 4.77 (mt, 1H: CH at 2α); 4.82 (broad d, J=18 Hz, 1H: the other H of the CH$_2$ at 5ε); 4.87 (dd, J=10 and 1 Hz, 1H: CH at 1α); 5.12 (d, J=5 Hz, 1H: CH at 5α); 5.25 (dd, J=9 and 6.5 Hz, 1H: CH at 4α); 5.52 (d, J=8 Hz, 1H: CH at 6γ); 5.53 (mt, 1H: CH at 5γ); 5.87 (resolved q, J=7 and 1 Hz, 1H: CH at 1β); 6.45 (d, J=8 Hz, 2H: aromatic Hs at 4ε); 6.60 (d, J=10 Hz, 1H: CONH at 2); 6.86 (d, J=8 Hz, 2H: aromatic Hs at 4δ); from 7.20 to 7.40 (mt: the 7 Hs corresponding to the aromatic Hs at 6α- to H$_4$ and to H$_5$); 7.72 (dd, J=4 and 1 Hz, 1H: H$_6$); 8.42 (d, J=10 Hz, 1H: CONH at 1); 8.50 (d, J=8 Hz, 1H: CONH at 6); 11.68 (s, 1H: OH).

EXAMPLE 28

The process was performed as in Example 1, but starting with a crude mixture containing 5δ-chloromethyl-4ζ-methylamino-4ζ-dedimethylamino-4ε-chloro-5δ,5γ- dehydropristinamycin $I_E$. 0.88 g of 5δ-morpholinomethyl-4ζ-methylamino-4ζ-dedimethylamino-5δ,5γ-dehydro-4ζ-chloropristinamycin $I_E$ was obtained in the form of a yellow solid melting at 170° C.

$^1$H NMR spectrum (400 MHz, CDCl$_3$): 0.93 (t, J=7.5 Hz, 3H: CH$_3$ at 2γ); from 1.15 to 1.40 (mt, 3H: 1H of the CH$_2$ at 3β-1H of the CH$_2$ at 3γ and 1H of the CH$_2$ at 5β); 1.30 (d, J=7 Hz, 3H: CH$_3$ at 1γ); 1.57 (mt, 1H: the other H of the CH$_2$ at 3γ); from 1.60 to 1.85 (mt: the 2 Hs corresponding to the CH$_2$ at 2β); 1.98 (mt, 1H: the other H of the CH$_2$ at 3β); 2.35 (unres. mult., 4H: NCH$_2$ of the morpholine); 2.59 (broad dd, J=16.5 and 5.5 Hz, 1H: the other H of the CH$_2$ at 5β); from 2.85 to 3.05 (mt, 3H: CH$_2$N and 1H of the CH$_2$ at 4β); 2.88 (d, J=5 Hz, 3H: ArNCH$_3$); from 3.05 to 3.25 (mt, 1H: the other H of the CH$_2$ at 4β); 3.14 (s, 3H: NCH$_3$); 3.28 (mt, 1H: 1H of the CH$_2$ at 3δ); 3.36 (broad d, J=18 Hz, 1H: 1H of the CH$_2$ at 5ε); 3.47 (mt, 1H: the other H of the CH$_2$ at 3δ); 3.68 (mt, 4H: CH$_2$O of the morpholine); 4.30 (q, J=5 Hz, 1H: ArNH); 4.56 (dd, J=8 and 5.5 Hz, 1H: CH at 3α); from 4.70 to 4.85 (mt, 2H: CH at 2α and the other H of the CH$_2$ at 5ε); 4.87 (dd, J=10 and 1 Hz, 1H: CH at 1α); 5.18 (d, J=5 Hz, 1H: CH at 5α); from 5.20 to 5.35 (mt, 1H: CH at 4α); 5.52 (d, J=8 Hz, 1H: CH at 6α); 5.57 (mt, 1H: CH at 5γ); 5.88 (resolved q, J=7 and 1 Hz, 1H: CH at 1β); 6.43 (d, J=8 Hz, 1H: aromatic H at 4ε); 6.57 (d, J=10 Hz, 1H: CONH at 2); 6.83 (dd, J=8 and 1.5 Hz, 1H: aromatic H at 4δ para to the Cl); 6.95 (d, J=1.5 Hz, 1H: aromatic H at 4δ ortho to the Cl); from 7.20 to 7.40 (mt: the 7 Hs corresponding to the aromatic Hs at 6α- to H$_4$ and to H$_5$); 7.64 (dd, J=4 and 1 Hz, 1H: H$_6$); 8.35 (d, J=10 Hz, 1H: CONH at 1); 8.51 (d, J=8 Hz, 1H: CONH at 6); 11.68 (s, 1H: OH).

EXAMPLE 29

The process was performed as in Example 1, but starting with a crude mixture containing 5δ-chloromethyl-4ζ-(N-methyl-N-allyloxycarbonyl)amino-4ζ-dedimethylamino-4ε-chloro-5δ,5γ-dehydropristinamycin $I_E$. 0.85 g of 5δ-morpholinomethyl-4ζ-(N-methyl-N-allyloxycarbonyl) amino-4ζ-dedimethylamino-5δ,5γ-dehydropristinamycin $I_E$ was obtained in the form of a cream-colored solid melting at 154° C.

$^1$H NMR spectrum (400 MHz, CDCl$_3$): 0.92 (t, J=7.5 Hz, 3H: CH$_3$ at 2γ); 1.13 (very broad d, J=16 Hz, 1H: 1H of the CH$_2$ at 5β); from 1.15 to 1.40 (mt, 2H: 1H of the CH$_2$ at 3β and 1H of the CH$_2$ at 3γ); 1.31 (d, J=7 Hz, 3H: CH$_3$ at 1γ); 1.55 (mt, 1H: the other H of the CH$_2$ at 3γ); from 1.55 to 1.80 (mt: the 2 Hs corresponding to the CH$_2$ at 2β); 2.00 (mt, 1H: the other H of the CH$_2$ at 3β); 2.35 (unres. mult., 4H: NCH$_2$ of the morpholine); 2.55 (broad dd, J=16 and 5.5 Hz, 1H: the other H of the CH$_2$ at 5β); 2.85 (s, 2H: CH$_2$N); 3.08 (dd, J=14.5 and 7 Hz, 1H: 1H of the CH$_2$ at 4β); 3.15 (s, 3H: NCH$_3$); from 3.20 to 3.35 (mt, 2H: the other H of the CH$_2$ at 4β and 1H of the CH$_2$ at 3δ); 3.29 (s, 3H: ArNCH$_3$); 3.35 (broad d, J=18 Hz, 1H: 1H of the CH$_2$ at 5ε); 3.48 (mt, 1H: the other H of the CH$_2$ at 3δ); 3.68 (mt, 4H: CH$_2$O of the morpholine); 4.56 (dd, J=8.5 and 6 Hz, 1H: CH at 3α); 4.64 (d, J=5.5 Hz, 2H: ArNCOOCH$_2$); 4.78 (mt, 1H: CH at 2α); 4.82 (broad d, J=18 Hz, 1H: the other H of the CH$_2$ at 5ε); 4.85 (dd, J=10 and 1 Hz, 1H: CH at 1α); 5.12 (d, J=5.5 Hz, 1H: CH at 5α); 5.19 and 5.27 (2 broad ds, J=11 Hz and J=18 Hz respectively, 1H each; =CH$_2$); 5.31 (dd, J=9 and 7 Hz, 1H: CH at 4α); from 5.50 to 5.60 (mt, 1H: CH at 5γ); 5.53 (d, J=8 Hz, 1H: CH at 6α); from 5.80 to 6.00 (mt 1H: CH=); 5.87 (resolved q, J=7 and 1 Hz, 1H: CH at 1β); 6.56 (d, J=9.5 Hz, 1H: CONH at 2); 7.03 (d, J=8 Hz, 2H: aromatic Hs at 4ε); 7.12 (d, J=8 Hz, 2H: aromatic Hs at 4δ); from 7.20 to 7.40 (mt: the 7 Hs corresponding to the aromatic Hs at 6α- to H$_4$ and to H$_5$); 7.68 (dd, J=4 and 1 Hz, 1H: H$_6$); 8.37 (d, J=10 Hz, 1H: CONH at 1); 8.44 (d, J=8 Hz, 1H: CONH at 6); 11.67 (s, 1H: OH).

Working as in Example 1, 5δ-chloromethyl-4ζ-(N-methyl-N-allyloxycarbonyl)amino-4ζ-dedimethylamino-4ε-chloro-5δ,5γ-dehydropristinamycin $I_E$ was prepared.

EXAMPLE 30

The process was performed as in Example 1, but starting with 150 cm$^3$ of acetonitrile, 15 g of a crude mixture containing 33 mol % of 5δ-chloromethyl-5δ,5γ-dehydropristinamycin $I_E$ and 2.5 cm$^3$ of tetrahydroisoquinoline. The reaction mixture was refluxed for 1 hour and then concentrated to dryness. The solid obtained was taken up 3 times in a mixture of dichloromethane/saturated aqueous sodium bicarbonate solution. After separation of the phases by settling, the organic phase was concentrated to dryness (45° C., 2.7 kPa) to give 15.4 g of solid. This solid was purified by chromatography on silica (eluent: 99.5/0.5 to 98.5/1.5 by volume gradient of dichloromethane/methanol) and then by preparative HPLC on 450 g of 100 Å 10 μm C$_8$ Kromasil silica, eluting with a water/acetonitrile mixture (60/40 by volume containing 0.1% trifluoroacetic acid). After concentration of the fractions to remove the acetonitrile, the aqueous phase was brought to pH 7–8 by addition of saturated sodium bicarbonate solution. The precipitate formed was filtered off, washed with 25 cm$^3$ of water and stirred overnight in saturated sodium bicarbonate solution. The solid thus obtained was filtered off, washed with 20 cm$^3$ of water and then dried at 40° C. under reduced pressure (90 Pa) to give 0.73 g of 5δ-(tetrahydroisoquinolyl) methyl-5δ,5γ-dehydropristinamycin $I_E$ in the form of white crystals melting at 212–214° C.

$^1$H NMR spectrum (400 MHz, CDCl$_3$): 0.92 (t, J=7.5 Hz, 3H: CH$_3$ at 2γ); 1.12 (very broad d, J=16.5 Hz, 1H: 1H of the CH$_2$ at 5); 1.23 (mt, 2H: 1H of the CH$_2$ at 3β and 1H of the CH$_2$ at 3γ); 1.33 (d, J=7 Hz, 3H: CH$_2$ at 1γ); 1.54 (mt, 1H: the other H of the CH$_2$ at 3γ); from 1.60 to 1.85 (mt: the 2 Hs corresponding to the CH$_2$ at 2β); 1.96 (mt, 1H: the other H of the CH$_2$ at 3β); 2.51 (broad d, J=16.5 and 5.5 Hz, 1H: the other H of the CH$_2$ at 5β); 2.66 (mt, 2H: ArCH$_2$); from 2.80 to 3.05 (mt, 3H: 1H of the CH$_2$ at 4β and NCH$_2$); 2.94 (s, 6H: ArN(CH$_3$)$_2$); 3.03 (AB, J=13 Hz, 2H: CH$_2$N); from 3.10 to 3.35 (mt, 2H: the other H of the CH$_2$ at 4β and 1H of the CH$_2$ at 3δ); 3.16 (s, 3H: NCH$_3$); 3.39 (broad d, J=18 Hz, 1H: 1H of the CH$_2$ at 5ε); 3.46 (mt, 1H: the other H of the CH$_2$ at 3δ); 3.57 (s, 2H: ArCH$_2$N); 4.57 (dd, J=8 and 6 Hz, 1H: CH at 3α); 4.77 (mt, 1H: CH at 2α); 4.84 (broad d, J=18 Hz, 1H: the other H of the CH$_2$ at 5ε); 4.87 (dd, J=10 and 1 Hz, 1H: CH at 1α); 5.13 (broad d, J=5 Hz, 1H: CH at 5α); 5.23 (dd, J=9 and 7 Hz, 1H: CH at 4α); 5.51 (d, J=8 Hz, 1H: CH at 6α), 5.58 (mt, 1H: CH at 5γ); 5.88 (resolved q, J=7 and 1 Hz, 1H: CH at 1β); 6.58 (d, J=9.5 Hz, 1H: CONH at 2); 6.62 (d, J=8 Hz, 2H: aromatic Hs at 4ε); 6.93 (d, J=8 Hz, 2H: aromatic Hs at 4δ); from 7.00 to 7.40 (mt: the 11 Hs corresponding to the aromatic Hs at 6α- to the 4 aromatic Hs of the 3,4-dihydro-1H-isoquinoline—to H$_4$ and to H$_5$); 7.73 (dd, J=4 and 1 Hz, 1H: H$_6$); from 8.35 to 8.45 (mt, 2H: CONH at 1 and CONH at 6); 11.68 (s, 1H: OH).

EXAMPLE 31

The process was performed as in Example 1, but starting with 150 cm$^3$ of acetonitrile, 15 g of a crude mixture containing 33 mol % of 5δ-chloromethyl-5δ,5γ-dehydropristinamycin $I_E$ and 3.6 g of 4-fluorophenylpiperazine. The reaction mixture was refluxed for 4 hours and then concentrated to dryness. The solid obtained was taken up in 250 cm³ of ethyl acetate.

The resulting solution was washed with 3 times 150 cm³ of water and 3 times 150 cm³ of hydrochloric acid. The aqueous phases were combined and then brought to pH 7–8 by addition of saturated sodium bicarbonate solution. The precipitate formed was filtered off, washed with 50 cm³ of water and then dried to give 11.2 g of solid. The solid obtained was purified by chromatography on silica (eluent: 99/1 by volume dichloromethane/methanol) and then by two preparative HPLCs on 450 g of 100 Å 10 μm C₈ Kromasil silica, eluting with a water/acetonitrile mixture (60/40 by volume containing 0.1% trifluoroacetic acid). After concentration of the fractions to remove the acetonitrile, the residual aqueous phase was brought to pH 7–8 by addition of saturated sodium bicarbonate solution. The precipitate formed was filtered off to give 0.7 g of a solid, which was stirred in 20 cm³ of ether, filtered off and then dried at 40° C. under reduced pressure (90 Pa). 285 mg of 5δ-[4-(4-fluoropheny)piperazin-1-yl]methyl-5δ,5γ-dehydropristinamycin $I_E$, were thus obtained in the form of off-white crystals melting at 165–167° C.

¹H NMR spectrum (400 MHz, CDCl₃): 0.91 (t, J=7.5 Hz, 3H: CH₃ at 2γ); 1.03 (very broad d, J=16 Hz, 1H: 1H of the CH₂ at 5β); 1.21 (mt, 2H: 1H of the CH₂ at 3β and 1H of the CH₂ at 3γ); 1.32 (d, J=7 Hz, 3H: CH₃ at 1γ); 1.53 (mt, 1H: the other H of the CH₂ at 3γ); from 1.60 to 1.80 (mt: the 2 Hs corresponding to the CH₂ at 2β); 1.98 (mt, 1H: the other H of the CH₂ at 3β); 2.46 (mt, 1H: the other H of the CH₂ at 5β); from 2.55 to 3.35 (mt, 10H: CH₂N of the piperazine at CH₂N); 2.95 (s, 6H: ArN(CH₃)₂); 2.98 (mt, 1H: 1H of the CH₂ at 4β); from 3.10 to 3.35 (mt, 2H: 1H of the CH₂ at 3δ and the other H of the CH₂ at 4β); 3.18 (s, 3H: NCH₃); from 3.35 to 3.50 (mt, 2H: 1H of the CH₂ at 5ε and the other H of the CH₂ at 3δ); 4.56 (dd, J=8 and 6 Hz, 1H: CH at 3α); 4.77 (mt, 1H: CH at 2α); 4.83 (mt, 1H: the other H of the CH₂ at 5ε); 4.88 (broad d, J=10 Hz, 1H: CH at 1α); 5.14 (broad d, J=5 Hz, 1H: CH at 5α); 5.20 (dd, J=9 and 6 Hz, 1H: CH at 4α); 5.54 (d, J=8 Hz, 1H: CH at 6α); 5.65 (unres. mult., 1H: CH at 5γ); 5.88 (broad q, J=7 Hz, 1H: CH at 1β); 6.56 (d, J=9.5 Hz, 1H: CONH at 2); 6.60 (d, J=8 Hz, 2H: aromatic Hs at 4ε); from 6.80 to 7.05 (mt, 6H: aromatic Hs at 4δ and aromatic Hs of the fluorophenyl); from 7.20 to 7.40 (mt: the 7 Hs corresponding to the aromatic Hs at 6α- to H₄ and to H₅); 7.73 (broad d, J=4 Hz, 1H: H₆); 8.38 (d, J=10 Hz, 1H: CONH at 1); 8.57 (unres. mult., 1H: CONH at 6); 11.66 (s, 1H: OH).

EXAMPLE 32

The process was performed as in Example 1, starting with a crude mixture containing 5δ-chloromethyl-4ζ-methylamino-4ζ-dedimethylamino-5δ,5γ-dehydropristinamycin $I_E$, to give 0.61 g of 5δ-piperidinomethyl-4ζ-methylamino-4ζ-dedimethylamino-5δ,5γ-dehydropristinamycin $I_E$ in the form of white crystals melting at 234° C.

¹H NMR spectrum (600 MHz, CDCl₃, δ in ppm). We observed the presence of minute traces of other unidentified pristinamycins and of conformers. 0.91 (t, J=7.5 Hz, 3H: CH₃ at 2γ); 1.16 (very broad d, J=17.5 Hz, 1H: 1H of the CH₂ at 5β); 1.23 (mt, 2H: 1H of the CH₂ at 3β and 1H of the CH₂ at 3γ); 1.31 (d, J=7 Hz, 3H: CH₃ at 1γ); from 1.35 to 1.65 (mt, 7H: the other H of the CH₂ at 3γ and CH₂ of the piperidine); from 1.60 to 1.80 (mt: the 2 Hs corresponding to the CH₂ at 2β); 1.97 (mt, 1H: the other H of the CH₂ at 3β); from 2.20 to 2.40 (unres. mult., 4H: NCH₂ of the piperidine); 2.49 (broad dd, J=17.5 and 5.5 Hz, 1H: the other H of the CH₂ at 5β); 2.78 (s, 2H: CH₂N); 2.82 (s, 3H: ArNCH₃); 2.95 (dd, J=14 and 7 Hz, 1H: 1H of the CH₂ at 4β); from 3.10 to 3.30 (mt, 2H: the other H of the CH₂ at 4β and 1H of the CH₂ at 3δ); 3.15 (s, 3H: NCH₃); 3.35 (broad d, J=18 Hz, 1H: 1H of the CH₂ at 5ε); 3.45 (mt, 1H: the other H of the CH₂ at 3δ); from 3.60 to 3.80 (broad unres. mult., 1H: ArNH); 4.55 (dd, J=8 and 5.5 Hz, 1H: CH at 3α); from 4.70 to 4.90 (mt, 2H: CH at 2α and the other H of the CH₂ at 5ε); 4.86 (broad d, J=10 Hz, 1H: CH at 1α); 5.10 (d, J=5.5 Hz, 1H: CH at 5α); 5.22 (dd, J=10 and 7 Hz, 1H: CH at 4α); 5.48 (mt, 1H: CH at 5γ); 5.52 (d, J=8 Hz, 1H: CH at 6α); 5.85 (broad q, J=7 Hz, 1H: CH at 1); 6.45 (d, J=8 Hz, 2H: aromatic Hs at 4ε); 6.58 (d, J=9.5 Hz, 1H: CONH at 2); 6.85 (d, J=8 Hz, 2H: aromatic Hs at 4δ); from 7.20 to 7.40 (mt: the 7 Hs corresponding to the aromatic Hs at 6α-H₄ and H₅); 7.71 (broad, d, J=4 Hz, 1H: H₆); 8.41 (mt, 2H: CONH at 1 and CONH at 6); 11.67 (s, 1H: OH).

EXAMPLE 33

The process was performed as in Example 1, but starting with 100 cm³ of acetonitrile, 30 g of a crude mixture containing 33 mol % of 5δ-chloromethyl-5δ,5γ-dehydropristinamycin $I_E$, and 2.9 cm³ of 2-methoxyethylamine. The reaction mixture was refluxed for 2 hours and was then concentrated to dryness under reduced pressure at 45° C. (2.7 kPa). The solid obtained was taken up in 50 cm³ of dichloromethane and 3 times 50 cm³ of 0.1 N hydrochloric acid. The aqueous solution was adjusted to pH 7–8 by addition of saturated aqueous sodium bicarbonate solution, and was extracted with twice 50 cm³ of dichloromethane. The organic phase was separated out after settling had taken place, dried over sodium sulphate, filtered, and concentrated to dryness at 45° C. under reduced pressure (2.7 kPa). 8.5 g of solid were thus obtained, which product was chromatographed on silica (eluent: 98/3 and then 97/3 by volume gradient of dichloromethane/methanol). A solid was obtained, which was stirred in 25 cm³ of diethyl ether, filtered off, washed with 10 cm³ of diethyl ether, and then dried under reduced pressure at 45° C. (90 Pa), to give 0.77 g of 5δ-(2-methoxyethylaminomethyl)-5δ,5γ-dehydropristinamycin $I_E$ in the form of a cream-colored solid melting at 200° C.

¹H NMR spectrum (400 MHz, CDCl₃, δ in ppm). We observed the presence of minute traces of other unidentified pristinamycins and of conformers. 0.92 (t, J=7.5 Hz, 3H: CH₃ at 2γ); 1.20 (very broad d, J=17 Hz, 1H: 1H of the CH₂ at 5β); 1.25 (mt, 2H: 1H of the CH₂ at 3β and 1H of the CH₂ at 3γ); 1.31 (d, J=7 Hz, 3H: CH₃ at 1γ); 1.55 (mt, 1H: the other H of the CH₂ at 3γ); from 1.60 to 1.80 (mt: the 2 Hs corresponding to the CH₂ at 2β); 1.98 (mt, 1H: the other H of the CH₂ at 3β); 2.51 (broad dd, J=17 and 5.5 Hz, 1H: the other H of the CH₂ at 5β); 2.71 (mt, 2H: NCH₂); from 2.85 to 2.95 (mt, 1H: NH); 2.93 (s, 6H: ArN(CH₃)₂); 2.99 (dd, J=14 and 7 Hz, 1H: 1H of the CH₂ at 4β); from 3.10 to 3.30 (mt, 4H: the other H of the CH₂ at 4β-1H of the CH₂ at 3δ and CH₂N); 3.13 (s, 3H: NCH₃); from 3.30 to 3.40 (mt, 1H: 1H of the CH₂ at 5ε); 3.33 (s, 3H: OCH₃); from 3.40 to 3.55 (mt, 1H: the other H of the CH₂ at 3δ); 3.48 (t, J=5.5 Hz, 2H: OCH₂); 4.57 (dd, J=8.5 and 5 Hz, 1H: CH at 3α); from 4.70 to 4.85 (mt, 2H: CH at 2α and the other H of the CH₂ at 5ε); 4.87 (broad d, J=10 Hz, 1H: CH at 1α); 5.12 (d, J=5.5 Hz, 1H: CH at 5α); 5.25 (dd, J=8 and 7 Hz, 1H: CH at 4α); 5.53 (mt, 1H: CH at 5γ); 5.56 (d, J=8 Hz, 1H: CH at 6α); 5.86 (broad q, J=7 Hz, 1H: CH at 1β); from 6.50 to 6.65 (mt, 1H: CONH at 2); 6,57 (d, J=8 Hz, 2H: aromatic Hs at 4ε); 6.89

(d, J=8 Hz, 2H: aromatic Hs at 4δ); from 7.20 to 7.40 (mt: the 7 Hs corresponding to the aromatic Hs at 6α-$H_4$ and $H_5$); 7.69 (broad d, J=4 Hz, 1H: $H_6$); 8.39 (d, J=10 Hz, 1H: CONH at 1); 8.54 (d, J=8 Hz, 1H: CONH at 6); 11.65 (broad unres. mult., 1H: OH).

EXAMPLE 34

The process was performed as in Example 1, but starting with 100 cm$^3$ of acetonitrile, 10 g of a crude mixture containing 33 mol % of 5δ-chloromethyl-5δ,5γ-dehydropristinamycin $I_E$, and 2.27 g of bis(2-methoxyethyl) amine. The reaction mixture was refluxed for 18 hours and then concentrated to dryness under reduced pressure at 45° C. (2.7 kPa) to give a solid, which was taken up in 200 cm$^3$ of dichloromethane and 100 cm$^3$ of aqueous solution. The pH of the aqueous phase was adjusted to pH 7–8 by addition of sodium bicarbonate. The organic phase was separated out after settling had taken place, dried over sodium sulphate, filtered, and concentrated to dryness at 45° C. under reduced pressure (2.7 kPa) to give 9.4 g of a yellow foam, which was chromatographed on silica (eluent: 97/3 by volume dichloromethane/methanol). The fractions containing the expected product were concentrated to dryness. The solid thus obtained was taken up in 200 cm$^3$ of methylene chloride. The solution obtained was extracted with 3 times 150 cm$^3$ of 0.1 N hydrochloric acid solution. The aqueous phase was taken up in saturated aqueous sodium bicarbonate solution, and then extracted with 3 times 150 cm$^3$ of methylene chloride. The organic phases were combined and then concentrated to dryness to give 2 g of product, which was recrystallized from 30 cm$^3$ of methanol. The solid thus obtained was filtered off, washed with twice 5 cm$^3$ of methanol, and then dried under reduced pressure at 45° C. (90 Pa) to give 1.38 g of 5δ-[bis(2-methoxyethyl) aminomethyl]-5δ,5γ-dehydropristinamycin $I_E$ in the form of white crystals melting at 180–182° C.

$^1$H NMR spectrum (400 MHz, CDCl$_3$, δ in ppm). We observed the presence of minute traces of other unidentified pristinamycins and of conformers. 0.91 (t, J=7.5 Hz, 3H: CH$_3$ at 2γ); 1.05 (very broad d, J=17 Hz, 1H: 1H of the CH$_2$ at 5β); 1.24 (mt, 2H: 1H of the CH$_2$ at 3β and 1H of the CH$_2$ at 3γ); 1.31 (d, J=7 Hz, 3H: CH$_3$ at 1γ); from 1.45 to 1.65 (mt: 1H corresponding to the other H of the CH$_2$ at 3γ); 1.66 and 1.73 (2 mts, 1H each: CH$_2$ at 2β); 1.99 (mt, 1H: the other H of the CH$_2$ at 3β); 2.46 (broad d, J=17 Hz, 1H: the other H of the CH$_2$ at 5β); 2.68 (mt, 4H: NCH$_2$); from 2.90 to 3.05 (mt, 1H: 1H of the CH$_2$ at 4β); 2.94 (s, 6H: ArN(CH$_3$)$_2$); 3.05 (broad s, 2H: CH$_2$N); from 3.10 to 3.30 (mt, 2H: the other H of the CH$_2$ at 4β and 1H of the CH$_2$ at 3δ); 3.18 (s, 3H: NCH$_3$); from 3.25 to 3.40 (mt, 1H: 1H of the CH$_2$ at 5ε); 3.33 (s, 6H: OCH$_3$); from 3.40 to 3.55 (mt, 1H: the other H of the CH$_2$ at 3δ); 3.48 (t, J=6 Hz, 4H: OCH$_2$); 4.58 (mt, 1H: CH at 3α); 4.78 (mt, 1H: CH at 2α); from 4.80 to 4.95 (mt, 1H: the other H of the CH$_2$ at 5ε); 4.87 (broad d, J=10 Hz, 1H: CH at 1α); 5.12 (d, J=5 Hz, 1H: CH at 5α); 5.22 (mt, 1H: CH at 4α); 5.48 (mt, 1H: CH at 5γ); 5.57 (d, J=8 Hz, 1H: CH at 6α); 5.86 (broad q, J=7 Hz, 1H: CH at 1β); 6.55 (d, J=9.5 Hz, 1H: CONH at 2); 6.62 (d, J=8 Hz, 2H: aromatic Hs at 4ε); 6.92 (d, J=8 Hz, 2H: aromatic Hs at 4δ); from 7.20 to 7.40 (mt: the 7 Hs corresponding to the aromatic Hs at 6α-$H_4$ and at $H_5$); 7.70 (broad d, J=4 Hz, 1H: $H_6$); 8.37 (d, J=10 Hz, 1H: CONH at 1); 8.45 (d, J=8 Hz, 1H: CONH at 6); 11.66 (s, 1H: OH).

EXAMPLE 35

0.14 g of 2-mercapto-1-methylimidazole were introduced into a three-necked flask containing 50 cm$^3$ of acetonitrile, followed by 62 mg of sodium hydride, 0.33 cm$^3$ of triethylamine, and 2.5 g of a crude mixture containing 33 mol % of 5δ-chloromethyl-5δ,5γ-dehydropristinamycin $I_E$. The reaction mixture was heated at 40° C. for 48 hours. After addition of 2 cm$^3$ of water, the reaction mixture was concentrated to dryness under reduced pressure (45° C., 2.7 kPa). The residue was taken up in 25 cm$^3$ of dichloromethane and the mixture obtained was washed with twice 20 cm$^3$ of water. The organic phase was separated out after settling had taken place, and was then extracted with 3 times 20 cm$^3$ of 0.1 N hydrochloric acid. After separation of the phases by settling, the aqueous phase was brought to pH 7 by addition of saturated aqueous sodium bicarbonate solution. The organic phase was extracted with twice 25 cm$^3$ of dichloromethane, dried over sodium sulphate, filtered, and then concentrated to dryness. The residue was taken up in 20 cm$^3$ of diisopropyl ether, filtered and dried at 40° C. under 90 Pa to give 0.6 g of 5δ-(1-methyl-2-imidazolylthiomethyl)-5δ,5γ-dehydropristinamycin $I_E$ in the form of a cream-colored solid melting at 147° C.

$^1$H NMR spectrum (400 MHz, CDCl$_3$, δ in ppm). We observed the presence of minute traces of other unidentified pristinamycins and of conformers. 0.91 (t, J=7.5 Hz, 3H: CH$_3$ at 2γ); from 1.15 to 1.35 (mt, 3H: 1H of the CH$_2$ at 5β-1H of the CH$_2$ at 3β and 1H of the CH$_2$ at 3γ); 1.29 (d, J=7 Hz, 3H: CH$_3$ at 1γ); 1.56 (mt, 1H: the other H of the CH$_2$ at 3γ); 1.64 and 1.72 (2 mts, 1H each: CH$_2$ at 2β); 1.98 (mt: 1H corresponding to the other H of the CH$_2$ at 3β); 2.38 (broad dd, J=17 and 5 Hz, 1H: the other H of the CH$_2$ at 5β); from 2.90 to 3.00 (mt, 1H: 1H of the CH$_2$ at 4β); 2.92 (s, 6H: ArN(CH$_3$)$_2$); from 3.10 to 3.30 (mt, 2H: the other H of the CH$_2$ at 4β-1H of the CH$_2$ at 3δ); 3.18 (s, 3H: NCH$_3$); 3.30 (broad d, J=18 Hz, 1H: 1H of the CH$_2$ at 5ε); 3.47 (mt, 1H: the other H of the CH$_2$ at 3δ); 3.55 (d, J=14 Hz, 1H: 1H of the SCH$_2$); 3.65 (s, 3H: NCH$_3$); 3.81 (d, J=14 Hz, 1H: the other H of the SCH$_2$); 4.56 (dd, J=8 and 7 Hz, 1H: CH at 3α); 4.76 (mt, 1H: CH at 2α); 4.87 (broad d, J=10 Hz, 1H: CH at 1α); 5.00 (broad d, J=18 Hz, 1H: the other H of the CH$_2$ at 5ε); 5.05 (d, J=5.5 Hz, 1H: CH at 5α); 5.17 (dd, J=10 and 6 Hz, 1H: CH at 4α); 5.50 (mt, 1H: CH at 5γ); 5.58 (d, J=8 Hz, 1H: CH at 6α); 5.87 (broad q, J=7 Hz, 1H: CH at 1β); 6.53 (d, J=8 Hz, 2H: aromatic Hs at 4ε); 6.57 (d, J=9 Hz, 1H: CONH at 2); 6.87 (d, J=8 Hz, 2H: aromatic Hs at 4δ); 6.93 and 7.10 (2 broad s, 1H each: CH=CH of the imidazole); from 7.20 to 7.40 (mt: the 7 Hs corresponding to the aromatic Hs at 6α- at $H_4$ and at $H_5$); 7.68 (broad d, J=4 Hz, 1H: $H_6$); 8.39 (d, J=10 Hz, 1H: CONH at 1); 8.45 (d, J=8 Hz, 1H: CONH at 6); 11.65 (broad unres. mult., 1H: OH).

EXAMPLE 36

0.57 cm$^3$ of 2-(diethylamino)ethanethiol, 18 mg of sodium hydride, and 0.54 cm$^3$ of triethylamine were introduced successively into a three-necked flask containing 25 cm$^3$ of acetonitrile. A solution of 50 cm$^3$ of acetonitrile and 7.5 g of a crude mixture containing 40 mol % of 5δ-chloromethyl-5δ,5γ-dehydropristinamycin $I_E$ (obtained as in Example 1), pre-adjusted to pH 7 by addition of triethylamine, was added to the resulting solution. The reaction mixture was heated at 45° C. for 48 hours. 2 cm$^3$ of water were then added, and the resulting mixture was concentrated to dryness under reduced pressure (45° C., 2.7 kPa). The residue was taken up in 50 cm$^3$ of dichloromethane, and the solution obtained was washed with twice 25 cm$^3$ of water. The organic phase was separated out after settling had taken place, dried over sodium sulphate, filtered, and concentrated to dryness to give 6 g of a crude product which was chromatographed on silica (eluent: 98/2 to 95/5 by volume gradient of dichloromethane/methanol). The fractions containing the expected product were concentrated to dryness, and the residue was taken up in 20 cm³ of dichloromethane. The solution obtained was filtered and then concentrated to dryness (45° C., 2.7 kPa). The residue was taken up in 25 cm³ of diisopropyl ether, filtered and dried at 40° C. under 90 Pa to give 1 g of 5δ-diethylaminoethylthiomethyl-5δ,5γ-dehydropristinamycin $I_E$ in the form of a pale yellow semi-hydrochloride melting at 135° C.

¹H NMR spectrum (600 MHz, CDCl₃, δ in ppm). 0.92 (t, J=7.5 Hz, 3H: CH₃ at 2γ); 1.10 (mt, 1H: 1H of the CH₂ at 5β); 1.17 (unres. mult., 6H: CH₃ ethyl); from 1.15 to 1.35 (mt, 2H: 1H of the CH₂ at 3β and 1H of the CH₂ at 3γ); 1.31 (d, J=7 Hz, 3H: CH₃ at 1γ); 1.57 (mt, 1H: the other H of the CH₂ at 3γ); 1.66 and 1.73 (2 mts, 1H each: CH₂ at 2β); 2.01 (mt, 1H: the other H of the CH₂ at 3β); 2.47 (broad dd, J=17 and 5.5 Hz, 1H: the other H of the CH₂ at 5β); from 2.55 to 2.95 (mt, 6H: NCH₂); 2.94 (s, 6H: ArN(CH₃)₂); 3.00 (dd, J=14 and 6.5 Hz, 1H: 1H of the CH₂ at 4β); 3.09 (d, J=15 Hz, 1H: 1H of the CH₂S); from 3.10 to 3.30 (mt, 3H: the other H of the CH₂ at 4β-1H of the CH₂ at 3δ and the other H of the CH₂S); 3.18 (s, 3H: NCH₃); 3.46 (mt, 1H: 1H of the CH₂ at 3δ); 3.53 (broad d, J=18 Hz, 1H: the other H of the CH₂ at 5ε); 4.58 (dd, J=8 and 6 Hz, 1H: CH at 3α); from 4.70 to 4.85 (mt, 2H: CH at 2α and the other H of the CH₂ at 5ε); 4.87 (broad d, J=10 Hz, 1H: CH at 1α); 5.11 (d, J=5 Hz, 1H: CH at 5α); 5.22 (dd, J=10 and 6.5 Hz, 1H: CH at 4α); 5.47 (d, J=8 Hz, 1H: CH at 6α); 5.56 (mt, 1H: CH at 5γ); 5.86 (broad q, J=7 Hz, 1H: CH at 1β); 6.55 to 6.65 (mt, 1H: CONH at 2); 6.60 (d, J=8 Hz, 2H: aromatic Hs at 4ε); 6.93 (d, J=8 Hz, 2H: aromatic Hs at 4δ); from 7.20 to 7.40 (mt: the 7 Hs corresponding to the aromatic Hs at 6α- to H₄ and to H₅); 7.72 (broad d, J=4 Hz, 1H: H₆); 8.40 (d, J=10 Hz, 1H: CONH at 1); 8.54 (d, J=8 Hz, 1H: CONH at 6); 11.67 (unres. mult., 1H: OH).

EXAMPLE 37

The process was performed as in Example 36, but starting with 25 cm³ of acetonitrile, 0.32 cm³ of (4-pyridyl)methanethiol, 120 mg of sodium hydride, on the one hand, and 5 g of a crude mixture containing 40 mol % of 5δ-chloromethyl-5δ,5γ-dehydropristinamycin $I_E$ and triethylamine dissolved in 40 cm³ of acetonitrile, on the other hand. The reaction mixture was heated at 45° C. for 1.5 hours and then treated as in Example 36 to give 5 g of a crude product which was chromatographed by flash chromatography on 0.04–0.063 mm silica (eluent: 99/1 to 98/2 by volume gradient of dichloromethane/methanol). The fractions containing the expected product were concentrated to dryness to give 1.2 g of a yellow foam, which was disintegrated in 25 cm³ of diisopropyl ether for 1 hour with stirring. The solid obtained was filtered off, washed with 10 cm³ of diisopropyl ether, and then dried at 45° C. under 90 Pa. 0.85 g of 5δ-(4-pyridylmethyl)thiomethyl-5δ,5γ-dehydropristinamycin $I_E$ was thus obtained in the form of a pale yellow solid melting at 138° C.

4-Pyridylmethanethiol was prepared according to J. Barnes et al., *Eur. J. Med. Chem.*, 23, 211–16, (1988), the disclosure of which is incorporated herein by reference.

¹H NMR spectrum (400 MHz, CDCl₃, δ in ppm). 0.92 (t, J=7.5 Hz, 3H: CH₃ at 2γ); 1.08 (very broad d, J=17 Hz, 1H: 1H of the CH₂ at 5β); from 1.20 to 1.35 (mt, 2H: 1H of the CH₂ at 3β and 1H of the CH₂ at 3γ); 1.33 (d, J=7 Hz, 3H: CH₃ at 1γ); 1.58 (mt, 1H: the other H of the CH₂ at 3γ); 1.67 and 1.74 (2 mts, 1H each: CH₂ at 2β); 2.01 (mt, 1H: the other H of the CH₂ at 3); 2.53 (broad dd, J=17 and 5 Hz, 1H: the other H of the CH₂ at 5β); from 2.85 to 3.00 (mt, 2H: CH₂S); 2.95 (s, 6H: ArN(CH₃)₂); 3.00 (dd, J=14 and 6.5 Hz, 1H: 1H of the CH₂ at 4β); from 3.10 to 3.25 (mt, 1H: the other H of the CH₂ at 4β); 3.19 (s, 3H: NCH₃); 3.32 (mt, 1H: 1H of the CH₂ at 3δ); from 3.45 to 3.60 (mt, 1H: 1H of the CH₂ at 5ε); 3.50 (mt, 1H: the other H of the CH₂ at 3δ); 3.54 and 3.62 (2 d, J=14 Hz, 1H each: SCH₂Ar); 4.60 (dd, J=8 and 6 Hz, 1H: CH at 3α); from 4.70 to 4.85 (mt, 2H: CH at 2α and the other H of the CH₂ at 5ε); 4.90 (broad d, J=10 Hz, 1H: CH at 1α); 5.13 (broad d, J=5 Hz, 1H: CH at 5α); 5.26 (dd, J=9.5 and 6.5 Hz, 1H: CH at 4α); 5.39 (broad d, J=4 Hz, 1H: CH at 5γ); 5.60 (d, J=8 Hz, 1H: CH at 6α); 5.89 (broad q, J=7 Hz, 1H: CH at 1β); from 6.50 to 6.65 (mt, 1H: CONH at 2); 6.60 (d, J=8 Hz, 2H: aromatic Hs at 4ε); 6.93 (d, J=8 Hz, 2H: aromatic Hs at 4δ); from 7.20 to 7.40 (mt: the 9 Hs corresponding to the aromatic Hs at 6α- to H₄- to H₅ and to the aromatic Hs in the β position of the pyridine); 7.74 (broad d, J=4 Hz, 1H: H₆); 8.40 (d, J=10 Hz, 1H: CONH at 1); 8.45 to 8.60 (mt, 3H: CONH at 6 and aromatic Hs in the a position of the pyridine); 11.68 (s, 1H. OH).

EXAMPLE 38

The process was performed as in Example 36, but starting with 25 cm³ of acetonitrile, 0.84 g of (3-pyridyl)methanethiol and 0.24 g of sodium hydride, on the one hand, and 10 g of a crude mixture containing 40 mol % of 5δ-chloromethyl-5δ,5γ-dehydropristinamycin $I_E$ and triethylamine in 75 cm³ of acetonitrile, on the other hand. The reaction mixture was heated at 60° C. for 2 hours and then treated as in Example 3 to give 8 g of a crude product, which was chromatographed on silica (eluent: 99/1 to 98/2 by volume gradient of dichloromethane/methanol). 2.1 g of product were thus obtained, and were repurified by flash chromatography on 0.040–0.063 mm silica (eluent: 99/1 to 97/3 gradient of dichloromethane/methanol). The fractions containing the expected product were concentrated, and the residue obtained was dried at 45° C. under 90 Pa to give 0.19 g of 5δ-3-pyridylmethylthiomethyl-5δ,5γ-(-dehydropristinamycin $I_E$ in the form of a yellow solid melting at 128° C.

(3-Pyridyl)methanethiol was prepared according to T. Brown et al., *J. Med. Chem.*, 35, 3613–24, (1992), the disclosure of which is incorporated herein by reference.

¹H NMR spectrum (400 MHz, CDCl₃, δ in ppm). 0.92 (t, J=7.5 Hz, 3H: CH₃ at 2γ); 1.08 (very broad d, J=17 Hz, 1H: 1H of the CH₂ at 5β); 1.27 (mt, 2H: 1H of the CH₂ at 3β and 1H of the CH₂ at 3γ); 1.33 (d, J=7 Hz, 3H: CH₃ at 1γ); 1.58 (mt, 1H: the other H of the CH₂ at 3γ); from 1.60 to 1.80 (mt, the 2 Hs corresponding to the CH₂ at 2β); 2.01 (mt, 1H: the other H of the CH₂ at 3β); 2.55 (dd, J=17 and 5.5 Hz, 1H: the other H of the CH₂ at 5β); 2.93 (s, 6H: ArN(CH₃)₂); from 2.85 to 3.05 (mt, 3H: 1H of the CH₂ at 4β and SCH₂); from 3.15 to 3.25 (mt, 1H: the other H of the CH₂ at 4β); 3.18 (s, 3H: NCH₃); 3.31 (mt, 1H: 1H of the CH₂ at 3δ); from 3.45 to 3.60 (mt, 2H: 1H of the CH₂ at 5ε and the other H of the CH₂ at 3δ); 3.57 and 3.66 (2d, J=14 Hz, 1H each: SCH₂Ar); 4.60 (dd, J=8 and 5.5 Hz, 1H: CH at 3α); from 4.75 to 4.85 (mt, 2H: CH at 2α and the other H of the CH₂ at 5ε); 4.88 (dd, J=10 and 1.5 Hz, 1H: CH at 1α); 5.12 (d, J=5.5 Hz, 1H: CH at 5α); 5.24 (dd, J=9 and 6.5 Hz, 1H: CH at 4α); 5.54 (very broad d, J=5 Hz, 1H: 5γ); 5.60 (d, J=8 Hz, 1H: CH at 6α); 5.88 (resolved q, J=7 and 1 Hz, 1H: CH at 1β); 6.57 (d, J=9 Hz, 1H: CONH at 2); 6.59 (d, J=8 Hz, 2H: aromatics Hs at 4ε); 6.93 (d, J=8 Hz, 2H: aromatic Hs at 4δ); from 7.25 to 7.45 (mt: the 8 Hs corresponding to the aromatic Hs at 6α- to the H at 5 of the pyridine- to H₄ to H₅); from 7.70 to 7.80

(mt, 2H: $H_6$ and H at 4 of the pyridine); 8.41 (d, J=10 Hz, 1H: CONH at 1); 8.48 (dd, J=5 and 1 Hz, 1H: H at 6 of the pyridine); 8.51 (d, J=8 Hz, 1H: CONH at 6); 8.58 (d, J=1 Hz, 1H: H at 2 of the pyridine); 11.68 (s, 1H: OH).

EXAMPLE 39

The process was performed as in Example 36, but starting with 2 liters of acetonitrile, 12.2 g of 2-piperidinoethanethiol, and 4.7 g of sodium hydride, on the one hand, and 190 g of a crude mixture containing 40 mol % of 5δ-chloromethyl-5δ,5γ-dehydropristinamycin $I_E$ and triethylamine dissolved in 1 liter of acetonitrile, on the other hand. The reaction mixture was heated at 55° C. for 4 hours and then treated as in Example 3 to give 215 g of crude product, which was purified by flash chromatography on 0.04–0.063 mm silica (eluent: 100/0 to 95/5 by volume gradient of dichloromethane/methanol). The fractions containing the expected product were concentrated and then repurified by preparative high performance liquid chromatography (HPLC) on 500 g of 100 Å 10 μm $C_8$ Kromasil silica, eluted with a water/acetonitrile mixture (70/30 by volume containing 0.1% trifluoroacetic acid). After concentration of the fractions containing the expected product, the residual aqueous phase was brought to pH 7–8 by addition of saturated sodium bicarbonate solution, and then extracted with 100 cm³ of dichloromethane. The organic phase was separated out after settling had taken place, dried over magnesium sulphate, filtered, and then concentrated to dryness. The residue was dried at 45° C. under 90 Pa to give 5.2 g of 5δ-piperidinoethylthiomethyl-5δ,5γ-dehydropristinamycin $I_E$ in the form of a yellow foam melting at 128° C.

2-Piperidinoethanethiol was prepared according to Clinton et al., *J. Am. Chem. Soc.*, 70, 950–51, (1948), the disclosure of which is incorporated herein by reference.

¹H NMR spectrum (400 MHz, $CDCl_3$, δ in ppm). 0.92 (t, J=7.5 Hz, 3H: $CH_3$ at 2γ); 1.10 (very broad d, J=16.5 Hz, 1H: 1H of the $CH_2$ at 5β); 1.26 (mt, 2H: 1H of the $CH_2$ at 3β and 1H of the $CH_2$ at 3γ); 1.31 (d, J=7 Hz, 3H: $CH_3$ at 1γ); 1.43 (mt, 2H: $CH_2$); 1.59 (mt, 5H: 2 $CH_2$ and the other H of the $CH_2$ at 3γ); from 1.60 to 1.80 (mt, 2H: $CH_2$ at 2β); 1.99 (mt, 1H: the other H of the $CH_2$ at 3β); from 2.35 to 2.60 (mt, 5H: $SCH_2CH_2N$ and the other H of the $CH_2$ at 5β); 2.58 (unres. mult., 4H: $NCH_2$); 2.95 (s, 6H: $ArN(CH_3)_2$); 2.99 (dd, J=14 and 7 Hz, 1H: 1H of the $CH_2$ at 4β); 3.09 (broad s, 2H: $SCH_2$); from 3.10 to 3.20 (mt, 1H: the other H of the $CH_2$ at 4β); 3.17 (s, 3H: $NCH_3$); 3.28 (mt, 1H: 1H of the $CH_2$ at 3δ); from 3.40 to 3.55 (mt, 2H: 1H of the $CH_2$ at 5ε and the other H of the $CH_2$ at 3δ); 4.57 (dd, J=8 and 5 Hz, 1H: CH at 3α); 4.78 (mt, 1H: CH at 2α); 4.84 (broad d, J=18 Hz, 1H: the other H of the $CH_2$ at 5ε); 4.87 (dd, J=10 and 1.5 Hz, 1H: CH at 1α); 5.09 (broad d, J=5.5 Hz, 1H: CH at 5α); 5.22 (dd, J=9 and 7 Hz, 1H: CH at 4α); 5.50 (very broad d, J=4.5 Hz, 1H: 5γ); 5.52 (d, J=8 Hz, 1H: CH at 6α); 5.87 (resolved q, J=7 and 1.5 Hz, 1H: CH at 1β); 6.58 (d, J=9 Hz, 1H: CONH at 2); 6.61 (d, J=8 Hz, 2H: aromatic Hs at 4ε); 6.91 (d, J=8 Hz, 2H: aromatic Hs at 4δ); from 7.20 to 7.40 (mt: the 7 Hs corresponding to the aromatic Hs at 6α- to $H_4$ and to $H_5$); 7.70 (dd, J=4 and 1 Hz, 1H: $H_6$); 8.38 (d, J=10 Hz, 1H: CONH at 1); 8.45 (d, J=8 Hz, 1H: CONH at 6); 11.67 (unres. mult., 1H: OH).

EXAMPLE 40

The process was performed as in Example 36, but starting with 4 cm³ of acetonitrile, 67.3 mg of 2-mercaptobenzimidazole and 21.5 mg of sodium hydride, on the one hand, and 750 mg of a crude mixture containing 40 mol % of 5δ-chloromethyl-5δ,5γ-dehydropristinamycin $I_E$ and triethylamine in 2 cm³ of acetonitrile, on the other hand. The reaction mixture was heated at 45° C. for 4 hours and then treated as in Example 36 to give a crude product which was chromatographed by flash chromatography on 32–63 μm silica (eluent: 99/1 to 95/5 by volume gradient of dichloromethane/methanol). The fractions containing the expected product were concentrated and the residue obtained was dried at 45° C. under 90 Pa to give 115 mg of 5δ-2-benzimidazolylthiomethyl-5δ,5γ-dehydropristinamycin $I_E$ in the form of a white solid.

EXAMPLES 41 TO 49

Working by analogy with Example 29 or with the method described in International patent application WO 99/43699, the disclose of which is incorporated herein by reference, the following products were prepared:

EXAMPLE 41

4ζ-Dedimethylamino-4ζ-(N-methyl-N-4-pyridylmethyl)amino-5δ-morpholinomethyl-5δ,5γ-dehydropristinamycin $I_E$ in the form of a salmon-pink solid ¹H NMR spectrum (400 MHz, $CDCl_3$, δ in ppm). 0.91 (t, J=7.5 Hz, 3H: $CH_3$ at 2γ); 1.03 (unres. mult., 1H: 1H of the $CH_2$ at 5β); 1.25 (mt, 2H: 1H of the $CH_2$ at 3β and 1H of the $CH_2$ at 3γ); 1.33 (d, J=7 Hz, 3H: $CH_3$ at 1γ); from 1.40 to 1.80 (mt: the 3 Hs corresponding to the other H of the $CH_2$ at 3γ and to the $CH_2$ at 2β); 1.99 (mt, 1H: the other H of the $CH_2$ at 3β); 2.39 (unres. mult., 4H: $NCH_2$); 2.48 (very broad d, J=17 Hz, 1H: the other H of the $CH_2$ at 5β); from 2.85 to 3.05 (mt, 3H: 1H of the $CH_2$ at 4β and $NCH_2$); 3.09 (s, 3H: $ArNCH_3$); from 3.10 to 3.45 (mt, 3H: the other H of the $CH_2$ at 4β-1H of the $CH_2$ at 3δ and 1H of the $CH_2$ at 5ε); 3.16 (s, 3H: $NCH_3$); 3.46 (mt, 1H: the other H of the $CH_2$ at 3δ); 3.73 (unres. mult., 4H: $CH_2O$); 4.53 (AB, J=17 Hz, 2H: $ArNCH_2Ar$); 4.57 (dd, J=8.5 and 5.5 Hz, 1H: CH at 3α); from 4.70 to 4.85 (mt, 2H: CH at 2α and the other H of the $CH_2$ at 5ε); 4.87 (dd, J=10 and 1.5 Hz, 1H: CH at 1α); 5.10 (broad d, J=5.5 Hz, 1H: CH at 5α); 5.20 (dd, J=10 and 7 Hz, 1H: CH at 4α); from 5.50 to 5.65 (unres. mult., 1H: CH at 5γ); 5.53 (d, J=8 Hz, 1H: CH at 6α); 5.86 (resolved q, J=7 and 1.5 Hz, 1H: CH at 1β); 6.52 (d, J=8 Hz, 2H: aromatic Hs at 4ε); 6.90 (d, J=8 Hz, 2H: aromatic Hs at 4δ); 7.00 (unres. mult., 1H: CONH at 2); from 7.20 to 7.40 (mt: the 9 Hs corresponding to the aromatic Hs at 6α- to the aromatic Hs in the β position of the pyridine- to $H_4$ and to $H_5$); 7.62 (broad d, J=4 and 1 Hz, 1H: $H_6$); 8.37 (d, J=10 Hz, 1H: CONH at 1); 8.48 (broad d, J=8 Hz, 1H: CONH at 6); 8.60 (d, J=6 Hz, 2H: aromatic Hs in the a position of the pyridine); 11.65 (s, 1H: OH).

EXAMPLE 42

4ζ-Dedimethylamino-4ζ-(N-methyl-N-phenyloxycarbonyl)amino-5δ-morpholinomethyl-5δ,5γ-dehydropristinamycin $I_E$ in the form of an amorphous white powder Mass spectrum—DCI (Desorption Chemical Ionization—ammonia) m/z 1056 corresponding to M+H⁺ Purity 85% (HPLC eluent 50/50 by volume water/$CH_3CN$+0.1% trifluoroacetic acid).

EXAMPLE 43

4ζ-Dedimethylamino-4ζ-(N-methyl-N-propyloxycarbonyl)amino-5δ-morpholinomethyl-5δ,5γ-dehydropristinamycin $I_E$ in the form of an amorphous white powder Mass spectrum—DCI (Desorption Chemical Ionization—ammonia) m/z 1022 corresponding to M+H⁺ Purity 86% (HPLC eluent 50/50 by volume water/CH₃CN+0.1% trifluoroacetic acid).

EXAMPLE 44

4ζ-Dedimethylamino-4ζ-(N-methyl-N-isobutyloxycarbonyl)amino-5δ-morpholinomethyl-5δ,5γ-dehydropristinamycin $I_E$ in the form of an amorphous white powder melting at about 148° C. (dec.)

¹H NMR spectrum (400 MHz, CDCl₃, δ in ppm). From 0.80 to 1.00 (mt, 9H: CH₃ at 2γ and the CH₃s of the isobutyl); from 1.15 to 1.35 (mt, 3H: 1H of the CH₂ at 5β-1H of the CH₂ at 3β and 1H of the CH₂ at 3γ); 1.32 (d, J=7 Hz, 3H: CH₃ at 1γ); from 1.55 to 1.80 (mt: the 3 Hs corresponding to the other H of the CH₂ at 3γ and to the CH₂ at 2β); from 1.85 to 2.05 (mt, 2H: the other H of the CH₂ at 3β and the CH of the isobutyl); 2.36 (unres. mult., 4H: NCH₂); 2.59 (broad dd, J=18 and 5 Hz, 1H: the other H of the CH₂ at 5β); 2.86 (s, 2H: NCH₂); 3.09 (dd, J=14 and 6.5 Hz, 1H: 1H of the CH₂ at 4); 3.14 (s, 3H: NCH₃); from 3.20 to 3.35 (mt, 2H: the other H of the CH₂ at 4β and 1H of the CH₂ at 3δ); 3.30 (s, 3H: ArNCH₃); 3.36 (broad d, J=17 Hz, 1H: 1H of the CH₂ at 5ε); 3.49 (mt, 1H: the other H of the CH₂ at 3δ); 3.70 (mt, 4H: CH₂O); 3.93 (d, J=7 Hz, 2H: ArNCOOCH₂); 4.56 (dd, J=7 and 5.5 Hz, 1H: CH at 3α); from 4.75 to 4.90 (mt, 3H: CH at 2α- the other H of the CH₂ at 5ε and CH at 1α); 5.15 (broad d, J=5 Hz, 1H: CH at 5α); 5.35 (mt, 1H: CH at 4α); 5.54 (d, J=8 Hz, 1H: CH at 6α); 5.56 (mt, 1H: CH at 5γ); 5.88 (resolved q, J=7 and 1.5 Hz, 1H: CH at 1β); 6.57 (d, J=9 Hz, 1H: CONH at 2); 7.03 (d, J=8 Hz, 2H: aromatic Hs at 4ε); 7.13 (d, J=8 Hz, 2H: aromatic Hs at 4δ); from 7.15 to 7.40 (mt: the 7 Hs corresponding to the aromatic Hs at 6α- to H₄ and to H₅); 7.70 (broad d, J=4.5 Hz, 1H: H₆); 8.37 (d, J=10 Hz, 1H: CONH at 1); 8.46 (d, J=8 Hz, 1H: CONH at 6); 11.68 (s, 1H: OH).

EXAMPLE 45

4ζ-Dedimethylamino-4ζ-(N-methyl-N-ethyloxycarbonyl)amino-5δ-morpholinomethyl-5δ,5γ-dehydropristinamycin $I_E$ in the form of an amorphous white powder melting at about 158° C. (dec.)

¹H NMR spectrum (400 MHz, CDCl₃, δ in pm). 0.93 (t, J=7.5 Hz, 3H: CH₃ at 2γ); from 1.05 to 1.20 (mt, 1H: 1H of the CH₂ at 5β) from 1.20 to 1.40 (mt, 2H: 1H of the CH₂ at 3β and 1H of the CH₂ at 3γ); 1.26 (t, J=7 Hz, 3H: CH₃); 1.30 (d, J=7 Hz, 3H: CH₃ at 1γ); from 1.50 to 1.80 (mt: the 3 Hs corresponding to the other H of the CH₂ at 3γ and to the CH₂ at 2β); 2.01 (mt, 1H: the other H of the CH₂ at 3β); 2.37 (unres. mult., 4H: NCH₂); 2.54 (mt, 1H: the other H of the CH₂ at 5β); 2.86 (s, 2H: NCH₂); 3.08 (dd, J=13 and 7 Hz, 1H: 1H of the CH₂ at 4β); 3.17 (s, 3H: NCH₃); from 3.20 to 3.40 (mt, 2H: the other H of the CH₂ at 4β and 1H of the CH₂ at 3δ); 3.28 (s, 3H: ArNCH₃); 3.35 (broad d, J=17 Hz, 1H: 1H of the CH₂ at 5ε); 3.50 (mt, 1H: the other H of the CH₂ at 3δ); 3.70 (mt, 4H: CH₂O); 4.21 (q, J=7 Hz, 2H: ArNCOOCH₂); 4.58 (dd, J=8 and 5.5 Hz, 1H: CH at 3α); from 4.70 to 4.90 (mt, 2H: CH at 2α and the other H of the CH₂ at 5ε); 4.88 (broad d, J=10 Hz, 1H: CH at 1α); 5.13 (broad d, J=5 Hz, 1H: CH at 5α); 5.31 (dd, J=10 and 7 Hz, 1H: CH at 4α); from 5.50 to 5.60 (mt, 2H: CH at 5γ and CH at 6α); 5.88 (broad q, J=7 Hz, 1H: CH at 1β); 6.56 (d, J=9 Hz, 1H: CONH at 2); 7.05 (d, J=8 Hz, 2H: aromatic Hs at 4ε); 7.13 (d, J=8 Hz, 2H: aromatic Hs at 4δ); from 7.20 to 7.40 (mt: the 7 Hs corresponding to the aromatic Hs at 6α- to H₄ and to H₅); 7.68 (broad d, J=4.5 Hz, 1H: H₆); 8.37 (d, J=10 Hz, 1H: CONH at 1); 8.45 (d, J=8 Hz, 1H: CONH at 6); 11.67 (s, 1H: OH).

EXAMPLE 46

4ζ-Dedimethylamino-4ζ-(N-methyl-N-para-tolyloxycarbonyl)amino-5δ-morpholinomethyl-5δ,5γ-dehydropristinamycin $I_E$ in the form of an amorphous white powder melting at about 147° C. (dec.)

¹H NMR spectrum (400 MHz, CDCl₃, δ in ppm). 0.93 (t, J=7.5 Hz, 3H: CH₃ at 2γ); from 1.15 to 1.35 (mt, 3H: 1H of the CH₂ at 5β-1H of the CH₂ at 3β and 1H of the CH₂ at 3γ); 1.31 (d, J=7 Hz, 3H CH₃ at 1γ); from 1.50 to 1.65 (mt: 1H corresponding to the other H of the CH₂ at 3γ); 1.67 to 1.77 (2 mts, 1H each: CH₂ at 2β); 2.00 (mt, 1H: the other H of the CH₂ at 3β); from 2.30 to 2.40 (unres. mult., 4H: NCH₂); 2.35 (s, 3H: ArCH₃); 2.52 (mt, 1H: the other H of the CH₂ at 5β); 2.82 (s, 2H: NCH₂); 3.11 (dd, J=14 and 7 Hz, 1H: 1H of the CH₂ at 4β); 3.16 (s, 3H: NCH₃); from 3.20 to 3.50 (mt, 3H: the other H of the CH₂ at 4β-1H of the CH₂ at 3δ and 1H of the CH₂ at 5ε; 3.40 (broad s, 3H: ArNCH₃); 3.50 (mt, 1H: the other H of the CH₂ at 3δ); 3.70 (mt, 4H: CH₂O); 4.58 (dd, J=8 and 6.5 Hz, 1H: CH at 3α); from 4.75 to 4.90 (mt, 3H: CH at 2α- the other H of the CH₂ at 5ε and the CH at 1α); 5.13 (broad d, J=5.5 Hz, 1H: CH at 5α); 5.34 (dd, J=7.5 and 7 Hz, 1H: CH at 4α); 5.45 (unres. mult., 1H: CH at 5γ); 5.53 (d, J=8 Hz, 1H: CH at 6α); 5.87 resolved q, J=7 and 1.5 Hz, 1H: CH at 1β); 6.56 (d, J=9 Hz, 1H: CONH at 2); from 6.95 to 7.40 (mt: the 15 Hs corresponding to the aromatic Hs at 4ε- to the aromatic Hs at 4ε- to the aromatic Hs of the tolyl—to the aromatic Hs at 6α- to H₄ and to H₅); 7.64 (broad d, J=4.5 Hz, 1H: H₆); 8.35 (d, J=10 Hz, 1H: CONH at 1); 8.44 (d, J=8 Hz, 1H: CONH at 6); 11.67 (s, 1H: OH).

EXAMPLE 47

4ζ-Dedimethylamino-4ζ-(N-methyl-N-3-butenyloxycarbonyl)amino-5δ-morpholinomethyl-5δ,5γ-dehydropristinamycin $I_E$ in the form of a white solid melting at 138–140° C.

¹H NMR spectrum (400 MHz, CDCl₃, δ in ppm). 0.93 (t, J=7.5 Hz, 3H: CH₃ at 2γ); from 1.15 to 1.35 (mt, 3H: 1H of the CH₂ at 5β-1H of the CH₂ at 3β and 1H of the CH₂ at 3γ); 1.31 (d, J=7 Hz, 3H: CH₃ at 1γ); from 1.50 to 1.65 (mt: 1H corresponding to the other H of the CH₂ at 3γ); from 1.65 to 1.80 (mt, 2H: CH₂ at 2β); 2.00 (mt, 1H: the other H of the CH₂ at 3β); from 2.30 to 2.45 (mt, 2H: CH₂); 2.37 (unres. mult., 4H: NCH₂); 2.57 (broad dd, J=17 and 5.5 Hz, 1H: the other H of the CH₂ at 5β); 2.86 (s, 2H: NCH₂); 3.09 (dd, J=14 and 7 Hz, 1H: 1H of the CH₂ at 4β); 3.14 (s, 3H: NCH₃); from 3.15 to 3.35 (mt, 2H: the other H of the CH₂ at 4β and 1H of the CH₂ at 3δ); 3.27 (s, 3H: ArNCH₃); 3.36 (broad d, J=17 Hz, 1H: 1H of the CH₂ at 5ε); 3.50 (mt, 1H: the other H of the CH₂ at 3δ); 3.69 (mt, 4H: CH₂O); 4.19 (t, J=7 Hz, 2H: ArNCOOCH₂); 4.57 (dd, J=8 and 6.5 Hz, 1H: CH at 3α); from 4.70 to 4.85 (mt, 2H: CH at 2α and the other H of the CH₂ at 5ε); 4.87 (dd, J=10 and 1.5 Hz, 1H: CH at 1α); from 5.05 to 5.15 (mt, 2H: =CH₂); 5.14 (broad d, J=5.5 Hz, 1H: CH at 5α); 5.34 (dd, J=7.5 and 7 Hz, 1H: CH at 4α); 5.54 (d, J=8 Hz, 1H: CH at 6α); 5.56 (mt, 1H: CH at 5γ); from 5.65 to 5.85 (mt, 1H: CH=); 5.88 (resolved q, J=7 and 1.5 Hz, 1H: CH at 1β); 6.57 (d, J=9 Hz, 1H: CONH at 2); 7.04 (d, J=8 Hz, 2H: aromatic Hs at 4ε); 7.12 (d, J=8 Hz, 2H: aromatic Hs at 4δ); from 7.20 to 7.40 (mt: the 7 Hs corresponding to the aromatic Hs at 6α- to H₄ and to H₅); 7.69 (dd, J=4.5 and 1 Hz, 1H: H₆); 8.37 (d, J=10 Hz, 1H: CONH at 1); 8.46 (d, J=8 Hz, 1H: CONH at 6); 11.68 (s, 1H: OH).

EXAMPLE 48

4ζ-Dedimethylamino-4ζ-(N-methyl-N-neopentyloxycarbonyl)amino-5δ-morpholinomethyl-5δ,5γ-dehydropristinamycin $I_E$ in the form of a white solid melting at 140–146° C.

$^1$H NMR spectrum (400 MHz, CDCl$_3$, δ in ppm). From 0.75 to 1.00 (mt, 12H: CH$_3$ at 2γ and C(CH$_3$)$_3$); from 1.15 to 1.35 (mt, 3H: 1H of the CH$_2$ at 5β-1H of the CH$_2$ at 3β and 1H of the CH$_2$ at 3γ); 1.30 (d, J=7 Hz, 3H: CH$_3$ at 1γ); from 1.50 to 1.80 (mt: the 3 Hs corresponding to the other H of the CH$_2$ at 3γ and to the CH$_2$ at 2β); 1.99 (mt, 1H: the other H of the CH$_2$ at 3β); 2.35 (unres. mult., 4H: NCH$_2$); 2.59 (broad dd, J=17 and 5 Hz, 1H: the other H of the CH$_2$ at 5β), 2.85 (s, 2H: NCH$_2$); from 3.10 to 3.40 (mt, 4H: CH$_2$ at 4β-1H of the CH$_2$ at 3δ and 1H of the CH$_2$ at 5ε); 3.12 (s, 3H: NCH$_3$); 3.30 (s, 3H: ArNCH$_3$); 3.49 (mt, 1H: the other H of the CH$_2$ at 3δ); 3.68 (mt, 4H: CH$_2$O); 3.84 (s, 2H: ArNCOOCH$_2$); 4.55 (dd, J=7 and 5 Hz, 1H: CH at 3α); from 4.70 to 4.85 (mt, 2H: CH at 2α and the other H of the CH$_2$ at 5ε); 4.86 (dd, J=10 and 1.5 Hz, 1H: CH at 1α); 5.15 (broad d, J=5 Hz, 1H: CH at 5α); 5.35 (t, J=8 Hz, 1H: CH at 4α); from 5.50 to 5.60 (mt, 2H: CH at 6α and CH at 5γ); 5.87 (resolved q, J=7 and 1.5 Hz, 1H: CH at 1β); 6.57 (d, J=9 Hz, 1H: CONH at 2); 7.03 (d, J=8 Hz, 2H: aromatic Hs at 4ε); 7.12 (d, J=8 Hz, 2H: aromatic Hs at 4δ); from 7.20 to 7.40 (mt: the 7 Hs corresponding to the aromatic Hs at 6α- to H$_4$ and to H$_5$); 7.69 (dd, J=4.5 and 1 Hz, 1H: H$_6$); 8.37 (d, J=10 Hz, 1H: CONH at 1); 8.46 (d, J=8 Hz, 1H: CONH at 6); 11.67 (s, 1H: OH).

EXAMPLE 49

1.3 g of 4ζ-dedimethylamino-4ζ-(N-methyl-N-allyloxycarbonyl)amino-5δ-morpholinomethyl-5δ,5γ-dehydropristinamycin $I_E$, prepared as in Example 29, were introduced into a three-necked flask containing 30 cm$^3$ of dioxane, followed by 10 mg of triphenylphosphine and 20 mg of tris(benzylideneacetone)palladium. The reaction mixture was refluxed for 39 hours, adding 3 times 20 mg of tris(benzylideneacetone)palladium in the course of the final 21 hours. The reaction mixture was concentrated under reduced pressure to give 1.1 g of a green foam, which was chromatographed on silica (eluent: 95/5 by volume dichloromethane/methanol). 0.45 g of a product was obtained, which was repurified by preparative HPLC on 450 g of 100 Å 10 μm C$_8$ Kromasil silica (eluent: 65/35 by volume water/acetonitrile containing 0.1% trifluoroacetic acid). After concentration of the fractions containing the expected product, the residual aqueous phase was brought to pH 7–8 by addition of saturated sodium bicarbonate solution. The mixture obtained was extracted with twice 20 cm$^3$ of dichloromethane. The organic phases were combined, dried over magnesium sulphate, filtered, and then concentrated to dryness. The residue was dried at 45° C. under 90 Pa to give 130 mg of 4ζ-dedimethylamino-4ζ-(N-methyl-N-allyl)amino-5δ-morpholinomethyl-5δ,5γ-dehydropristinamycin $I_E$ in the form of a pale yellow solid melting at 156° C.

$^1$H NMR spectrum (400 MHz, CDCl$_3$, δ in ppm). 0.92 (t, J=7.5 Hz, 3H: CH$_3$ at 2γ); from 0.90 to 1.00 (mt, 1H: 1H of the CH$_2$ at 5β); 1.23 (mt, 2H: 1H of the CH$_2$ at 3β and 1H of the CH$_2$ at 3γ); 1.31 (d, J=7 Hz, 3H: CH$_3$ at 1γ); 1.55 (mt, 1H: the other H of the CH$_2$ at 3γ); from 1.60 to 1.80 (mt: the 2 Hs corresponding to the CH$_2$ at 2β); 2.00 (mt, 1H: the other H of the CH$_2$ at 3β); 2.37 (unres. mult., 4H: NCH$_2$); 2.43 (broad dd, J=17 and 5 Hz, 1H: the other H of the CH$_2$ at 5β); 2.85 (unres. mult., 2H: NCH$_2$); from 2.90 to 3.00 (mt, 1H: 1H of the CH$_2$ at 4β); 2.96 (s, 3H: ArNCH$_3$); from 3.15 to 3.25 (mt, 1H: the other H of the CH$_2$ at 4β); 3.20 (s, 3H: NCH$_3$); 3.33 (broad d, J=18 Hz, 1H: 1H of the CH$_2$ at 5ε); 3.47 (mt, 1H: 1H of the CH$_2$ at 3δ); from 3.65 to 3.80 (mt, 5H: the other H of the CH$_2$ at 3δ and CH$_2$O); 3.91 and 3.99 (2 dd, J=16 and 5 Hz, 1H each: ArNCH$_2$); 4.60 (dd, J=8 and 5.5 Hz, 1H: CH at 3α); 4.78 (mt, 1H: CH at 2α); 4.85 (broad d, J=18 Hz, 1H: the other H of the CH$_2$ at 5ε); 4.88 (dd, J=10 and 1.5 Hz, 1H: CH at 1α); 5.10 (broad d, J=5 Hz, 1H: CH at 5α); from 5.10 to 5.25 (mt, 3H: =CH$_2$ and CH at 4α); 5.49 (very broad d, J=5 Hz, 1H: CH at 5γ); 5.52 (d, J=8 Hz, 1H: CH at 6α); from 5.80 to 5.95 (mt, 1H: CH=); 5.86 (resolved q, J=7 and 1.5 Hz, 1H: CH at 1β); 6.56 (d, J=9 Hz, 1H: CONH at 2); 6.57 (d, J=8 Hz, 2H: aromatic Hs at 4ε); 6.93 (d, J=8 Hz, 2H: aromatic Hs at 4δ); from 7.20 to 7.40 (mt: the 7 Hs corresponding to the aromatic Hs at 6α- to H$_4$ and to H$_5$); 7.75 (dd, J=4.5 and 1 Hz, 1H: H$_6$); 8.39 (d, J=10 Hz, 1H: CONH at 1); 8.47 (d, J=8 Hz, 1H: CONH at 6); 11.66 (s, 1H: OH).

As examples of streptogramin compounds of formula (β), the following were prepared according to or by analogy with the method below:

REFERENCE EXAMPLE (16R)-16-Deoxo-16-fluoropristinamycin II$_B$:

0.2 cm$^3$ of acetic acid and 0.6 g of tetra-n-butylammonium fluoride trihydrate were added at 20° C., under an argon atmosphere, to 1.12 g of (16R)-16-deoxo-16-fluoro-14-O-(tert-butyidiphenylsilyl)pristinamycin II$_B$ dissolved in 10 cm$^3$ of tetrahydrofuran. After stirring for 168 hours, the reaction mixture was concentrated to dryness under reduced pressure (2.7 kPa) to give 1 g of a brown oil, which was purified by flash chromatography [eluent: dichloromethane/methanol/acetonitrile (90/515 by volume)]. 0.3 g of (16R)-16-deoxo-16-fluoropristinamycin II$_B$ was obtained in the form of a pale beige solid melting at about 125° C. (dec.).

$^1$H NMR spectrum (400 MHz, CDCl$_3$, δ in pm): 0.96 (d, J=6.5 Hz: 3H); 1.00 (d, J=6.5 Hz: 3H); 1.10 (d, J=6.5 Hz: 3H); from 1.55 to 2.05 (mt: 5H); 1.83 (s, 3H); from 2.10 to 2.30 (mt: 2H); 2.76 (mt: 1H); 2.98 (mt: 1H); 3.21 (mt: 1H); 3.48 (mt: 1H); 3.87 (mt: 1H); 4.07 (mt: 1H); 4.55 (mt: 1H); from 4.75 to 4.90 (mt: 3H); 5.14 (uncoupled doublet, J$_{HF}$=48 Hz: 1H); 5.39 (d, J=9 Hz: 1H); 5.71 (mt: 1H); 5.82 (dd, J=17 and 2 Hz: 1H); 6.00 (mt: 1H); 6.21 (d, J=16 Hz: 1H); 6.52 (dd, J=17 and 5 Hz: 1H); 8.12 (s: 1H).

(16R)-16-Deoxo-16-fluoro-14-O-(tert-butyidiphenylsilyl)pristinamycin II$_B$ was prepared in the following way:

0.464 cm$^3$ of diethylaminosulphur trifluoride was added slowly at 20° C., under an argon atmosphere, to 2 g of (16S)-16-hydroxy-14-O-(tert-butyidiphenylsilyl) pristinamycin II$_B$ dissolved in 50 cm$^3$ of dichloromethane. After stirring for 2 hours, the reaction mixture was poured into 100 cm$^3$ of saturated aqueous sodium bicarbonate solution. The organic phase was separated out after settling had taken place, washed with twice 100 cm$^3$ of water, dried over magnesium sulphate, filtered, and then concentrated to dryness under reduced pressure (2.7 kPa) to give 2.1 g of an ochre-colored solid, which was purified by flash chromatography [eluent: dichloromethane/acetonitrile/methanol gradient (100/0/0; 99/0.5/0.5 and then 98/1/1 by volume)]. 1.35 g of (16R)-16-deoxo-16-fluoro-14-O-(tert-butyidiphenylsilyl)pristinamycin II$_B$ were obtained in the form of a white solid melting at about 116° C. (dec.).

$^1$H NMR spectrum (400 MHz, CDCl$_3$, δ in ppm): 0.96 (d, J=6.5 Hz: 3H); 0.99 (d, J=6.5 Hz: 3H); from 1.00 to 1.15

(mt: 12H); 1.29 (s, 3H); from 1.55 to 1.95 (mt: 4H); 1.96 (mt: 1H); 2.13 (mt: 1H); 2.24 (mt: 1H); 2.76 (mt: 1H); 2.85 (mt: 1H); 3.03 (mt: 1H); 3.39 (mt: 1H); 3.80 (mt: 1H); 4.01 (mt: 1H); 4.57 (mt: 1H); 4.72 (mt: 1H); from 4.75 to 4.85 (mt: 2H); 5.01 (uncoupled doublet, $J_{HF}$=48 Hz: 1H); 5.38 (d, J=9 Hz: 1H); 5.50 (mt: 1H); 5.81 (dd, J=17 and 1.5 Hz: 1H); 5.97 (mt: 1H); 6.10 (d, J=15.5 Hz: 1H); 6.49 (dd, J=17 and 5 Hz: 1H); from 7.30 to 7.50 (mt: 6H); 7.63 (broad d, J=7 Hz: 2H); 7.68 (broad d, J=7 Hz: 2H); 8.08 (s: 1H).

(16S)-16-Hydroxy-14-O-(tert-butyldiphenylsilyl) pristinamycin $II_B$ was prepared in the following way:

29 cm$^3$ of diisopropylethylamine were added at 20° C., under an argon atmosphere, to 22 g of (16S)-16-hydroxypristinamycin $II_B$ dissolved in 200 cm$^3$ of dichloromethane, followed by dropwise addition of 43.2 cm$^3$ of tert-butyidiphenylchlorosilane and addition of 1.01 g of 4-dimethylaminopyridine. After stirring for 22 hours, the reaction mixture was poured into 600 cm$^3$ of saturated aqueous sodium bicarbonate solution. The aqueous phase was separated out after settling had taken place, and then extracted with twice 100 cm$^3$ of dichloromethane. The organic phases were combined, washed with 400 cm$^3$ of saturated aqueous sodium chloride solution, dried over sodium sulphate, filtered, and then concentrated to dryness under reduced pressure (2.7 kPa) to give 70.6 g of a viscous orange oil, which was stirred in 600 cm$^3$ of diisopropyl ether for 16 hours. After filtration and drying under reduced pressure (2.7 kPa) at 20° C., 28 g of (16S)-16-hydroxy-14-O-(tert-butyidiphenylsilyl)pristinamycin $II_B$ were obtained in the form of a pink-red solid melting at about 133° C. (dec.).

$^1$H NMR spectrum (400 MHz, CDCl$_3$, δ in ppm): 0.95 (d, J=6.5 Hz: 3H); from 1.00 to 1.05 (mt: 9H); 1.08 (s, 9H); from 1.40 to 1.80 (mt: 3H); from 1.90 to 2.15 (mt: 3H); 2.23 (broad d, J=14 Hz: 1H); 2.75 (mt: 1H); 2.83 (dd, J=17 and 11 Hz: 1H); 3.10 (dd, J=17 and 2.5 Hz: 1H); 3.25 (mt: 1H); from 3.60 to 3.75 (mt: 2H); 4.49 (mt: 1H); 4.56 (mt: 1H); from 4.60 to 4.70 (mt: 2H); 4.87 (mt: 1H); 5.49 (mt: 1H); 5.74 (dd, J=17 and 2 Hz: 1H); 5.78 (d, J=9 Hz: 1H); 5.95 (mt: 1H); 6.04 (d, J=16 Hz: 1H); 6.41 (dd, J=17 and 4 Hz: 1H); from 7.30 to 7.50 (mt: 6H); 7.64 (dd, J=7 and 1.5 Hz: 2H); 7.69 (dd, J=7 and 1.5 Hz: 2H); 8.11 (s: 1H).

16(S)-16-Hydroxypristinamycin $II_B$ was prepared in the following way:

A suspension of 11.35 g of sodium borohydride in 550 cm$^3$ of dichloromethane was refluxed for 20 minutes. 68.6 cm$^3$ of acetic acid were then added dropwise over about 30 minutes, followed by addition of a solution (predried over sodium sulphate) of 52.75 g of pristinamycin $II_B$ in 230 cm$^3$ of dichloromethane, over about 45 minutes. The reaction mixture was stirred for 4.5 hours at reflux and then for 16 hours at 20° C. 500 cm$^3$ dichloromethane and 1500 cm$^3$ of water were then added to the reaction mixture. The organic phase was separated out after settling had taken place and the aqueous phase was extracted with 500 cm$^3$ of dichloromethane. The organic phases were combined and the pH was adjusted to 8 by slow addition of 1000 cm$^3$ of saturated aqueous sodium bicarbonate solution. The resulting organic phase was washed successively with 1000 cm$^3$ of water and 1000 cm$^3$ of saturated aqueous sodium chloride solution and then treated with 3S vegetable charcoal, dried over sodium sulphate, filtered and concentrated to dryness under reduced pressure (2.7 kPa) to give 50 g of a pale yellow solid. 378 cm$^3$ of aqueous 0.5 M ammonium hydroxide solution were added at 20° C. to a solution of the above solid in 900 cm$^3$ of dichloromethane. After stirring for 16 hours at 20° C., the organic phase was separated out by settling, washed with 1000 cm$^3$ of water and then with 1000 cm$^3$ of saturated aqueous sodium chloride solution, dried over sodium sulphate, filtered, and concentrated to dryness under reduced pressure (2.7 kPa) to give 46 g of a pale yellow solid, which was purified by flash chromatography [eluent: dichloromethane/methanol gradient (98/2 and 97/3 by volume)]. 31.68 g of (16S)-16-hydroxypristinamycin $II_B$ were obtained in the form of an off-white solid melting at about 131° C. (dec.).

$^1$H NMR spectrum (400 MHz, CDCl$_3$, δ in ppm): 0.96 (d, J=6.5 Hz: 3H); 1.02 (d, .J=6.5 Hz: 3H); 1.07 (d, J=6.5 Hz: 3H); from 1.70 to 1.90 (mt: 3H); 1.76 (s: 3H); 1.97 (mt: 2H); 2.12 (mt: 1H); 2.26 (broad d: 14.5 Hz: 1H); 2.56 (d, J=3 Hz: 1H); 2.76 (mt: 1H); 2.90 (dd, J=16 and 10 Hz: 1H); 3.08 (dd, J=16 and 3 Hz: 1H); 3.35 (mt: 1H); 3.82 (mt: 2H); 3.99 (d, J=2.5 Hz: 1H); from 4.40 to 4.55 (mt: 2H); from 4.65 to 4.75 (mt: 2H); 5.03 (mt: 1H); from 5.65 to 5.85 (mt: 3H); 6.01 (mt: 1H); 6.21 (d, J=16 Hz: 1H); 6.46 (dd, J=17 and 5 Hz: 1H); 8.13 (s: 1H).

The present invention also relates to pharmaceutical compositions containing at least one streptogramin compound according to the invention, where appropriate in the form of a salt, either alone or in combination with one or more compatible and pharmaceutically acceptable diluents or adjuvants. The invention also relates to such pharmaceutical compositions that additionally contain at least one A-group streptogramin compound or, where appropriate, one of the salts thereof, combined with the streptogramin(s) of formula (I).

The compositions according to the invention can be adminstered orally, parenterally, topically, rectally, or as an aerosol.

Solid compositions for oral administration which can be used include, for example, tablets, pills, gel capsules, powders, and granules. In these compositions, the active compound according to the present invention, generally in the form of a combination, was mixed with one or more inert diluents or adjuvants, such as sucrose, lactose or starch. These compositions can comprise substances other than diluents, for example, a lubricant, such as magnesium stearate or a coating intended for controlled release.

Liquid compositions for oral administration which can be used include, for example, pharmaceutically acceptable solutions, suspensions, emulsions, syrups, and elixirs containing inert diluents such as water or liquid paraffin. These compositions can also comprise substances other than diluents, for example wetting, sweetening, or flavoring products.

The compositions for parenteral administration may be sterile solutions or emulsions. Solvents and vehicles which may be used include propylene glycol, a polyethylene glycol, plant oils, such as olive oil, and injectable organic esters, for example ethyl oleate. These compositions can also contain adjuvants, such as wetting agents, isotonic agents, emulsifiers, dispersants, and stabilizers.

The sterilization can be performed in several ways, for example, using a bacteriological filter, by irradiation, or by heating. The compositions can also be prepared in the form of sterile solid compositions which may be dissolved at the time of use in sterile water or in any other injectable sterile medium.

The compositions for topical administration may be, for example, creams, ointments, lotions or aerosols.

The compositions for rectal administration are suppositories or rectal capsules, which contain, besides the active principle, excipients such as cocoa butter, semisynthetic glycerides, and/or polyethylene glycols.

The compositions may also be aerosols. For use in the form of liquid aerosols, the compositions may be stable sterile solutions or solid compositions that are dissolved at the time of use in apyrogenic sterile water, in saline, or in any other pharmaceutically acceptable vehicle. For use in the form of dry aerosols intended to be inhaled directly, the active principle was finely divided and combined with a water-soluble solid vehicle or diluent with a particle size ranging from 30 μm and 80 μm, for example dextran, mannitol, or lactose.

In human therapy, the novel streptogramin compounds according to the invention can be useful in the treatment of infections of bacterial origin. The doses depend on the desired effect and on the duration of the treatment. The doctor will determine the dosage he considers to be the most suitable as a function of the treatment, depending on the age, weight, degree of infection, and other factors specific to the individual to be treated. Generally, the doses range from 1 g to 3 g of active product taken 2 or 3 times a day, orally for an adult.

The example which follows illustrates a composition according to the invention.

EXAMPLE

Tablets containing a 250 mg dose of active product and having the composition below were prepared according to the usual technique:

| | |
|---|---|
| 5δ-(1-morpholino)methyl-5δ,5γ-dehydropristinamycin $I_E$ | 75 mg |
| pristinamycin $II_B$ | 175 mg |
| excipient: starch, hydrated silica, dextrin, gelatin, magnesium stearate: qs | 500 mg |

The present invention may be embodied in other specific forms without departing from its spirit or essential characteristics. The described embodiments are to be considered in all respects as illustrative only and not restrictive. The scope of the invention is, therefore, indicated by the appended claims, rather than by the foregoing description. All changes which come within the meaning and range of equivalency of the claims are to be embraced within their scope.

What is claimed is:

1. A compound of formula (I):

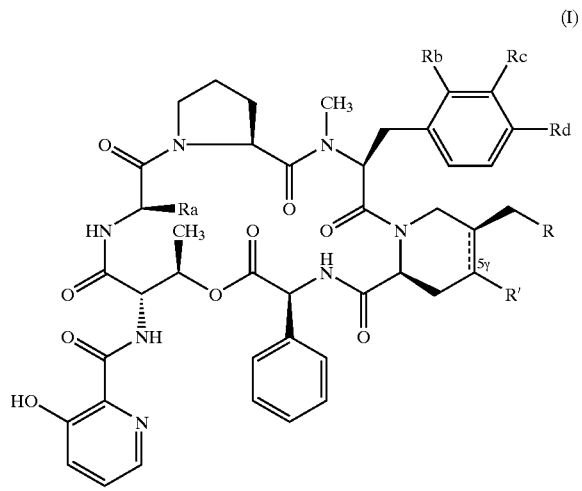

wherein:

R is chosen from —$NR_1R_2$ and —$SR_3$, wherein:
$R_1$ and $R_2$, which may be identical or different, are independently chosen from hydrogen and the radicals:
alkyl having from 1 to 8 carbons, which is unsubstituted or substituted with hydroxyl;
alkenyl having from 3 to 8 carbons;
cycloalkyl having from 3 to 8 carbons;
alkyloxy having from 1 to 8 carbons;
dialkylamino;
phenylalkyl, which is unsubstituted or substituted with one or more halogen atoms or radicals chosen from alkyl hydroxyalkyl, alkyloxy, and dialkylamino;
saturated and unsaturated 3- to 8-membered heterocyclylalkyl containing one or more hetero atoms chosen from nitrogen, sulphur and oxygen; and
dialkylaminoalkyl;
or, alternatively,
$R_1$ and $R_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;

R₃ is chosen from:
  alkyl radicals having 1 to 8 carbons and cycloalkyl radicals having 3 to 8 carbons, both of which are substituted with a radical:
  —NR₁R₂, wherein R₁ and R₂, which may be identical or different, are chosen from hydrogen and alkyl radicals, or form, together with the nitrogen atom to which they are attached, a heterocycle as defined above; a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
    hydroxyl;
    alkyl;
    phenyl, which is unsubstituted or substituted with a halogen atom;
    phenylalkyl;
    phenylalkenyl, the alkenyl portion having from 2 to 4 carbons;
    hydroxyalkyl;
    acyl;
    alkyloxycarbonyl; and
    heterocyclyl and heterocyclylcarbonyl, wherein the heterocyclyl portion is 4- to 6-membered, saturated or unsaturated, and contains one or more hetero atoms chosen from oxygen, sulphur, and nitrogen;
or, alternatively,
  R₃ is chosen from 3- to 7-membered, saturated and unsaturated, monocyclic and polycyclic, heterocyclyl and heterocyclylmethyl radicals, and which are unsubstituted or substituted with one or more alkyl radicals;

is an unsaturated ring residue which is unsubstituted at 5γ:

or a saturated ring residue which is substituted at 5γ with a fluoro radical:

Ra is chosen from methyl and ethyl radicals; and
Rb, Rc, and Rd have one of the definitions below:
1) Rb and Rc are both hydrogen; and
  Rd is chosen from hydrogen and methylamino and dimethylamino radicals;
2) Rb is hydrogen;
  Rc is chosen from hydrogen, chlorine, and bromine atoms, and from alkenyl radicals having from 3 to 5 carbons; and Rd is a radical
  —NMe-R''', wherein R''' is chosen from the radicals:
    alkyl, hydroxyalkyl having from 2 to 4 carbons, and alkenyl having from 2 to 8 carbons, which are unsubstituted or substituted with one or more radicals chosen from:
      phenyl;
      cycloalkyl having from 3 to 6 carbons;
      methyl;
      benzyl; and
      substituted benzyl, which is substituted with one or more substitutents chosen from:
        halogen atoms, and hydroxyl, alkyl, alkyloxy, alkylthio, alkylsulphinyl, alkylsulphonyl, amino, alkylamino and dialkylamino radicals; and
    heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:
      alkyl, alkenyl having from 2 to 8 carbons, cycloalkyl having from 3 to 6 carbons, saturated and unsaturated 4- to 6-membered heterocyclyl, phenyl, substituted phenyl as defined above for the definition of R₁, and benzyl radicals;
or, alternatively,
  R''' is chosen from cyanomethyl and carboxymethyl radicals, and from —CORe and —CH₂CORe, wherein Re is —OR'e, and wherein R'e is chosen from:
    alkyl having from 1 to 6 carbons;
    alkenyl having from 2 to 6 carbons;
    benzyl;
    phenyl;
    tolyl; and
    heterocyclylmethyl radicals, wherein the heterocyclyl portion is 5- or 6-membered and contains 1 or 2 hetero atoms chosen from sulphur, oxygen and nitrogen;
or, alternatively, Re is chosen from:
  alkylamino;
  alkylmethylamino; and
  heterocyclylamino and heterocyclylmethylamino radicals, wherein the heterocyclyl portion is saturated and 5- or 6-membered and contains 1 or 2 hetero atoms chosen from sulphur, oxygen, and nitrogen, and which are unsubstituted or substituted with a radical chosen from alkyl, benzyl, and alkyloxycarbonyl radicals;
3) Rb is hydrogen;
  Rd is chosen from —NHCH₃ and —N(CH₃)₂ radicals; and
  Rc is chosen from chlorine and bromine atoms, and from alkenyl radicals having from 3 to 5 carbons when Rd is —N(CH₃)₂;
4) Rb and Rd are both hydrogen; and
  Rc is chosen from halogen atoms and alkylamino, dialkylamino, alkyloxy, trifluoromethoxy, thioalkyl, alkyl having from 1 to 6 carbons, and trihalomethyl radicals;
5) Rb and Rc are both hydrogen; and
  Rd is chosen from halogen atoms, and ethylamino, diethylamino, methylethylamino, alkyloxy, trifluoromethoxy, alkylthio, alkylsulphinyl, alkylsulphonyl, alkyl having from 1 to 6 carbons, phenyl, and trihalomethyl radicals;
6) Rb is hydrogen;
  Rc is chosen from halogen atoms and alkylamino, dialkylamino, alkyloxy, trifluoromethoxy, and thioalkyl radicals, and alkyl radicals having from 1 to 6 carbons; and Rd is chosen from halogen atoms and amino, alkylamino, dialkylamino, alkyloxy, trifluoromethoxy, thioalkyl, alkyl having from 1 to 6 carbons, and trihalomethyl radicals; or 7) Rc is hydrogen; and
Rb and Rd are both methyl radicals;
with the proviso that, unless specifically defined, the alkyl and acyl radicals and portions of radicals are straight or branched and contain from 1 to 4 carbon atoms and that the alkenyl radicals also have a straight or branched chain and contain from 2 to 4 carbon atoms;

or a salt thereof.

2. A compound of formula (I) according to claim 1, wherein:

R is chosen from $-NR_1R_2$ and $-SR_3$, wherein:

$R_1$ and $R_2$, which may be identical or different, are independently chosen from hydrogen and the radicals:
alkyl having from 1 to 8 carbons, which is unsubstituted or substituted with hydroxyl;
alkenyl having from 3 to 8 carbons;
cycloalkyl having from 3 to 8 carbons;
alkyloxy having from 1 to 8 carbons;
dialkylamino;
phenylalkyl, which is unsubstituted or substituted with one or more halogen atoms or radicals chosen from alkyl, hydroxyalkyl, alkyloxy, and dialkylamino;
saturated and unsaturated 3- to 8-membered heterocyclylalkyl containing one or more hetero atoms chosen from nitrogen, sulphur and oxygen; and
dialkylaminoalkyl;
or, alternatively,
$R_1$ and $R_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;

$R_3$ is chosen from alkyl radicals having from 1 to 8 carbons, which are substituted with a radical $-NR_1R_2$, wherein:

$R_1$ and $R_2$, which may be identical or different, are chosen from alkyl radicals, or form, together with the nitrogen atom to which they are attached, a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;
or, alternatively,
$R_3$ is chosen from 3- to 7-membered, saturated and unsaturated, monocyclic and polycyclic, heterocyclyl and heterocyclylmethyl radicals, and which are unsubstituted or substituted with one or more alkyl radicals,

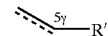

is an unsaturated ring residue which is unsubstituted at 5γ:

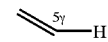

or a saturated ring residue which is substituted at 5γ with a fluoro radical:

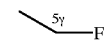

Ra is an ethyl radical; and
Rb, Rc, and Rd have one of the definitions below:
1) Rb and Rc are both hydrogen atoms and Rd is chosen from methylamino and dimethylamino radicals;
2) Rb is a hydrogen atom, Rc is chosen from hydrogen and chlorine atoms, and Rd is a radical —NMe-R''', wherein R''' is chosen from:
alkenyl radicals having from 2 to 8 carbons and heterocyclylmethyl radicals, and from —COOR'e, wherein R'e is chosen from:
alkyl having from 1 to 6 carbons, alkenyl having from 2 to 6 carbons, phenyl, and tolyl radicals; or
3) Rb is a hydrogen atom, Rd is chosen from $-NHCH_3$ and $-N(CH_3)_2$ radicals, and Rc is a chlorine atom;

or a salt thereof.

3. A compound of formula (I) according to claim 1, chosen from:
5δ-(1-morpholino)methyl-5δ,5γ-dehydropristinamycin $I_E$;
5δ-[N-methyl-N-2-(1,3-dioxolanyl)methyl]aminomethyl-5δ,5γ-dehydropristinamycin $I_E$;
5δ-morpholinomethyl-4ζ-methylamino-4ζ-dedimethylamino-5δ,5γ-dehydropristinamycin $I_E$;
5δ-morpholinomethyl-4ζ-methylamino-4ζ-dedimethylamino-5δ,5γ-dehydro-4ε-chloropristinamycin $I_E$; and
5δ-[bis(2-methoxyethyl)aminomethyl]-5δ,5γ-dehydropristinamycin $I_E$;
4ε-chloro-5δ-(diethylaminoethylthiomethyl)-5δ,5γ-dehydropristinamycin $I_E$;

5δ-(diethylaminoethylthiomethyl)-4ζ-methylamino-4ζ-dedimethylamino-5δ,5γ-dehydropristinamycin I$_E$;

4ε-chloro-5δ-(diethylaminoethylthiomethyl)-4ζ-methylamino-4ζ-dedimethylamino-5δ,5γ-dehydropristinamycin I$_E$;

5δ-(3-diethylaminopropylthiomethyl)-5δ,5γ-dehydropristinamycin I$_E$;

4ε-chloro-5δ-(3-diethylaminopropylthiomethyl)-5δ,5γ-dehydropristinamycin I$_E$;

5δ-(3-diethylaminopropylthiomethyl)-4ζ-methylamino-4ζ-dedimethylamino-5δ,5γ-dehydropristinamycin I$_E$;

4ε-chloro-5δ-(3-diethylaminopropylthiomethyl)-4ζ-methylamino-4ζ-dedimethylamino-5δ,5γ-dehydropristinamycin I$_E$;

5δ-(dimethylaminoethylthiomethyl)-5δ,5γ-dehydropristinamycin I$_E$;

4ε-chloro-5δ-(dimethylaminoethylthiomethyl)-5δ,5γ-dehydropristinamycin I$_E$;

5δ-(dimethylaminoethylthiomethyl)-4ζ-methylamino-4ζ-dedimethylamino-5δ,5γ-dehydropristinamycin I$_E$;

4ε-chloro-5δ-(dimethylaminoethylthiomethyl)-4ζ-methylamino-4ζ-dedimethylamino-5δ,5γ-dehydropristinamycin I$_E$;

4ε-chloro-5δ-(1-methyl-2-imidazolylthiomethyl)-5δ,5γ-dehydropristinamycin I$_E$;

5δ-(1-methyl-2-imidazolylthiomethyl)-4ζ-methylamino-4ζ-dedimethylamino-5δ,5γ-dehydropristinamycin I$_E$;

4ε-chloro-5δ-(1-methyl-2-imidazolylthiomethyl)-4ζ-methylamino-4ζ-dedimethylamino-5δ,5γ-dehydropristinamycin I$_E$;

5δ-(morpholinoethylthiomethyl)-5δ,5γ-dehydropristinamycin I$_E$;

4ε-chloro-5δ-(morpholinoethylthiomethyl)-5δ,5γ-dehydropristinamycin I$_E$;

5δ-(morpholinoethylthiomethyl)-4ζ-methylamino-4ζ-dedimethylamino-5δ,5γdehydropristinamycin I$_E$;

4ε-chloro-5δ-(morpholinoethylthiomethyl)-4ζ-methylamino-4ζ-dedimethylamino-5δ,5γ-dehydropristinamycin I$_E$;

4ε-chloro-5δ-(2-piperidinoethyl)thiomethyl-5δ,5γ-dehydropristinamycin I$_E$;

5δ-(2-piperidinoethyl)thiomethyl-4ζ-methylamino-4ζ-dedimethylamino-5δ,5γ-dehydropristinamycin I$_E$;

4ε-chloro-5δ-(2-piperidinoethyl)thiomethyl-4ζ-methylamino-4ζ-dedimethylamino-5δ,5γ-dehydropristinamycin I$_E$;

5δ-(3-piperidinopropyl)thiomethyl-5δ,5γ-dehydropristinamycin I$_E$;

4ε-chloro-5δ-(3-piperidinopropyl)thiomethyl-5δ,5γ-dehydropristinamycin I$_E$;

5δ-(3-piperidinopropyl)thiomethyl-4ζ-methylamino-4ζ-dedimethylamino-5δ,5γ-dehydropristinamycin I$_E$;

4ε-chloro-5δ-(3-piperidinopropyl)thiomethyl-4ζ-methylamino-4ζ-dedimethylamino-5δ,5γ-dehydropristinamycin I$_E$;

4ε-chloro-5δ-(4-pyridylmethylthiomethyl)-5δ,5γ-dehydropristinamycin I$_E$;

5δ-(4-pyridylmethylthiomethyl)-4ζ-methylamino-4ζ-dedimethylamino-5δ,5γ-dehydropristinamycin I$_E$;

4ε-chloro-5δ-(4-pyridylmethylthiomethyl)-4ζ-methylamino-4ζ-dedimethylamino-5δ,5γ-dehydropristinamycin I$_E$;

4ε-chloro-5δ-(3-pyridylmethylthiomethyl)-5δ,5γ-dehydropristinamycin I$_E$;

5δ-(3-pyridylmethylthiomethyl)-4ζ-methylamino-4ζ-dedimethylamino-5δ,5γ-dehydropristinamycin I$_E$;

4ε-chloro-5δ-(3-pyridylmethylthiomethyl)-4ζ-methylamino-4ζ-dedimethylamino-5δ,5γ-dehydropristinamycin I$_E$;

5δ-(2-pyridylmethylthiomethyl)-5δ,5γ-dehydropristinamycin I$_E$;

4ε-chloro-5δ-(2-pyridylmethylthiomethyl)-5δ,5γ-dehydropristinamycin I$_E$;

5δ-(2-pyridylmethylthiomethyl)-4ζ-methylamino-4ζ-dedimethylamino-5δ,5γ-dehydropristinamycin I$_E$;

4-chloro-5δ-(2-pyridylmethylthiomethyl)-4ζ-methylamino-4ζ-dedimethylamino-5δ,5γ-dehydropristinamycin I$_E$;

5δ-{[2-(4-methylpiperazin-1-yl)ethyl]thiomethyl}-5δ,5γ-dehydropristinamycin I$_E$;

4ε-chloro-5δ-{[2-(4-methylpiperazin-1-yl)ethyl]thiomethyl}-5δ,5γ-dehydropristinamycin I$_E$;

5δ-{[2-(4-methylpiperazin-1-yl)ethyl]thiomethyl}-4ζ-methylamino-4ζ-dedimethylamino-5δ,5γ-dehydropristinamycin I$_E$;

4ε-chloro-5δ-{[2-(4-methylpiperazin-1-yl)ethyl]thiomethyl}-4ζ-methylamino-4ζ-dedimethylamino-5δ,5γ-dehydropristinamycin I$_E$;

5δ-(butoxycarbonylaminoethylthiomethyl)-5δ,5γ-dehydropristinamycin I$_E$;

4ε-chloro-5δ-(butoxycarbonylaminoethylthiomethyl)-5δ,5γ-dehydropristinamycin I$_E$;

5δ-(butoxycarbonylaminomethylthioethyl)-4ζ-methylamino-4ζ-dedimethylamino-5δ,5γ-dehydropristinamycin I$_E$;

4ε-chloro-5δ-(butoxycarbonylaminoethylthiomethyl)-4ζ-methylamino-4ζ-dedimethylamino-5δ,5γ-dehydropristinamycin I$_E$;

5δ-(aminoethylthiomethyl)-5δ,5γ-dehydropristinamycin I$_E$;

4ε-chloro-5δ-(aminoethylthiomethyl)-5δ,5γ-dehydropristinamycin I$_E$;

5δ-(aminomethylthioethyl)-4ζ-methylamino-4ζ-dedimethylamino-5δ,5γ-dehydropristinamycin I$_E$;

4ε-chloro-5δ-(aminoethylthiomethyl)-4ζ-methylamino-4ζ-dedimethylamino-5δ,5γ-dehydropristinamycin I$_E$;

5δ-(pyrrolidinoethylthiomethyl)-5δ,5γ-dehydropristinamycin I$_E$;

4ε-chloro-5δ-(pyrrolidinoethylthiomethyl)-5δ,5γ-dehydropristinamycin I$_E$;

5δ-(pyrrolidinoethylthiomethyl)-4ζ-methylamino-4ζ-dedimethylamino-5δ,5γ-dehydropristinamycin I$_E$;

4ε-chloro-5δ-(pyrrolidinoethylthiomethyl)-4ζ-methylamino-4ζ-dedimethylamino-5δ,5γ-dehydropristinamycin I$_E$;

5δ-(diisopropylaminoethylthiomethyl)-5δ,5γ-dehydropristinamycin I$_E$;

4ε-chloro-5δ-(diisopropylaminoethylthiomethyl)-5δ,5γ-dehydropristinamycin I$_E$;

5δ-(diisopropylaminoethylthiomethyl)-4ζ-methylamino-4ζ-dedimethylamino-5δ,5γ-dehydropristinamycin I$_E$;

4ε-chloro-5δ-(diisopropylaminoethylthiomethyl)-4ζ-methylamino-4ζ-dedimethylamino-5δ,5γ-dehydropristinamycin I$_E$;

5δ-(N-ethyl-N-methylaminoethylthiomethyl)-5δ,5γ-dehydropristinamycin I$_E$;

4ε-chloro-5δ-(N-ethyl-N-methylaminoethylthiomethyl)-5δ,5γ-dehydropristinamycin I$_E$;

5δ-(N-ethyl-N-methylaminoethylthiomethyl)-4ζ-methylamino-4ζ-dedimethylamino-5δ,5γ-dehydropristinamycin I$_E$;

4ε-chloro-5δ-(N-ethyl-N-methylaminoethylthiomethyl)-4ζ-methylamino-4ζ-dedimethylamino-5δ,5γ-dehydropristinamycin I$_E$;

5δ-((2R)-3-diethylaminopropyl-2-thiomethyl)-5δ,5γ-dehydropristinamycin I$_E$;

4ε-chloro-5δ-((2R)-3-diethylaminopropyl-2-thiomethyl)-5δ,5γ-dehydropristinamycin I$_E$;

5δ-((2R)-3-diethylaminopropyl-2-thiomethyl)-4ζ-methylamino-4ζ-dedimethylamino-5δ,5γ-dehydropristinamycin I$_E$;

4ε-chloro-5δ-((2R)-3-diethylaminopropyl-2-thiomethyl)-4ζ-methylamino-4ζ-dedimethylamino-5δ,5γ-dehydropristinamycin I$_E$;

5δ-((2S)-3-diethylaminopropyl-2-thiomethyl)-5δ,5γ-dehydropristinamycin I$_E$;

4ε-chloro-5δ-((2S)-3-diethylaminopropyl-2-thiomethyl)-5δ,5γ-dehydropristinamycin I$_E$;

5δ-((2S)-3-diethylaminopropyl-2-thiomethyl)-4ζ-methylamino-4ζ-dedimethylamino-5δ,5γ-dehydropristinamycin I$_E$; and 4ε-chloro-5δ-((2S)-3-diethylaminopropyl-2-thiomethyl)-4ζ-methylamino-4ζ-dedimethylamino-5δ,5γ-dehydropristinamycin I$_E$;

or a salt thereof.

4. A compound of formula (I) according to claim 3, wherein said compound is 5δ-(1-morpholino)methyl-5δ,5γ-dehydropristinamycin I$_E$.

5. A compound of formula (I) according to claim 3, wherein said compound is 5δ-[N-methyl-N-2-(1,3-dioxolanyl)methyl]aminomethyl-5δ,5γ-dehydropristinamycin I$_E$.

6. A compound of formula (I) according to claim 3, wherein said compound is 5δ-morpholinomethyl-4ζ-methylamino-4ζ-dedimethylamino-5δ,5γ-dehydropristinamycin I$_E$.

7. A compound of formula (I) according to claim 3, wherein said compound is 5δ-morpholinomethyl-4ζ-methylamino-4ζ-dedimethylamino-5δ,5γ-dehydro-4ε-chloropristinamycin I$_E$.

8. A compound of formula (I) according to claim 3, wherein said compound is 5δ-[bis(2-methoxyethyl)aminomethyl]-5δ,5γ-dehydropristinamycin I$_E$.

9. A compound of formula (II):

(II)

R is chosen from —NR$_1$R$_2$ and —SR$_3$, wherein:
R$_1$ and R$_2$, which may be identical or different, are independently chosen from hydrogen and the radicals:
alkyl having from 1 to 8 carbons, which is unsubstituted or substituted with hydroxyl;
alkenyl having from 3 to 8 carbons;
cycloalkyl having from 3 to 8 carbons;
alkyloxy having from 1 to 8 carbons;
dialkylamino;
phenylalkyl, which is unsubstituted or substituted with one or more halogen atoms or radicals chosen from alkyl, hydroxyalkyl, alkyloxy, and dialkylamino;
saturated and unsaturated 3- to 8-membered heterocyclylalkyl containing one or more hetero atoms chosen from nitrogen, sulphur and oxygen; and
dialkylaminoalkyl;
or, alternatively,
R$_2$ and R$_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;
R$_3$ is chosen from:
alkyl radicals having from 1 to 8 carbons and cycloalkyl radicals having from 3 to 8 carbons, both of which are substituted with a radical:

—NR₁R₂, wherein R₁ and R₂, which may be identical or different, are chosen from hydrogen and alkyl radicals, or form, together with the nitrogen atom to which they are attached, a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;

or, alternatively,

R₃ is chosen from 3- to 7-membered, saturated and unsaturated, monocyclic and polycyclic, heterocyclyl and heterocyclylmethyl radicals, and which are unsubstituted or substituted with one or more alkyl radicals;

Ra is chosen from methyl and ethyl radicals; and

Rb, Rc, and Rd have one of the definitions below:

1) Rb and Rc are both hydrogen; and
   Rd is chosen from hydrogen and methylamino and dimethylamino radicals;

2) Rb is hydrogen;
   Rc is chosen from hydrogen, chlorine, and bromine atoms, and from alkenyl radicals having from 3 to 5 carbons; and Rd is a radical —NMe-R'", wherein R'" is chosen from the radicals:
   alkyl, hydroxyalkyl having from 2 to 4 carbons, and alkenyl having from 2 to 8 carbons, which are unsubstituted or substituted with one or more radicals chosen from:
   phenyl;
   cycloalkyl having from 3 to 6 carbons;
   methyl;
   benzyl; and
   substituted benzyl, which is substituted with one or more substitutents chosen from:
      halogen atoms, and hydroxyl, alkyl, alkyloxy, alkylthio, alkylsulphinyl, alkylsulphonyl, amino, alkylamino and dialkylamino radicals; and
   heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:
   alkyl, alkenyl having from 2 to 8 carbons, cycloalkyl having from 3 to 6 carbons, saturated and unsaturated 4- to 6-membered heterocyclyl, phenyl, substituted phenyl as defined above for the definition of R₁, and benzyl radicals;

or, alternatively,

R'" is chosen from cyanomethyl and carboxymethyl radicals, and from —CORe and —CH₂CORe, wherein Re is —OR'e, and wherein R'e is chosen from:
   alkyl having from 1 to 6 carbons;
   alkenyl having from 2 to 6 carbons;
   benzyl;
   phenyl;
   tolyl; and
   heterocyclylmethyl radicals, wherein the heterocyclyl portion is 5- or 6-membered and contains 1 or 2 hetero atoms chosen from sulphur, oxygen and nitrogen;

or, alternatively, Re is chosen from:
   alkylamino;
   alkylmethylamino; and
   heterocyclylamino and heterocyclylmethylamino radicals, wherein the heterocyclyl portion is saturated and 5- or 6-membered and contains 1 or 2 hetero atoms chosen from sulphur, oxygen, and nitrogen, and which are unsubstituted or substituted with a radical chosen from alkyl, benzyl, and alkyloxycarbonyl radicals;

3) Rb is hydrogen;
   Rd is chosen from —NHCH₃ and —N(CH₃)₂ radicals; and
   Rc is chosen from chlorine and bromine atoms, and from alkenyl radicals having from 3 to 5 carbons when Rd is —N(CH₃)₂;

4) Rb and Rd are both hydrogen; and
   Rc is chosen from halogen atoms and alkylamino, dialkylamino, alkyloxy, trifluoromethoxy, thioalkyl, alkyl having from 1 to 6 carbons, and trihalomethyl radicals;

5) Rb and Rc are both hydrogen; and
   Rd is chosen from halogen atoms, and ethylamino, diethylamino, methylethylamino, alkyloxy, trifluoromethoxy, alkylthio, alkylsulphinyl, alkylsulphonyl, alkyl having from 1 to 6 carbons, phenyl, and trihalomethyl radicals;

6) Rb is hydrogen;
   Rc is chosen from halogen atoms and alkylamino, dialkylamino, alkyloxy, trifluoromethoxy, and thioalkyl radicals, and alkyl radicals having from 1 to 6 carbons; and
   Rd is chosen from halogen atoms and amino, alkylamino, dialkylamino, alkyloxy, trifluoromethoxy, thioalkyl, alkyl having from 1 to 6 carbons, and trihalomethyl radicals; or 7) Rc is hydrogen; and
   Rb and Rd are both methyl radicals; with the proviso that, unless specifically defined, the alkyl and acyl radicals and portions of radicals are straight or branched and contain from 1 to 4 carbon atoms and that the alkenyl radicals also have a straight or branched chain and contain from 2 to 4 carbon atoms;

or a salt thereof.

10. A process for preparing a compound of formula (I):

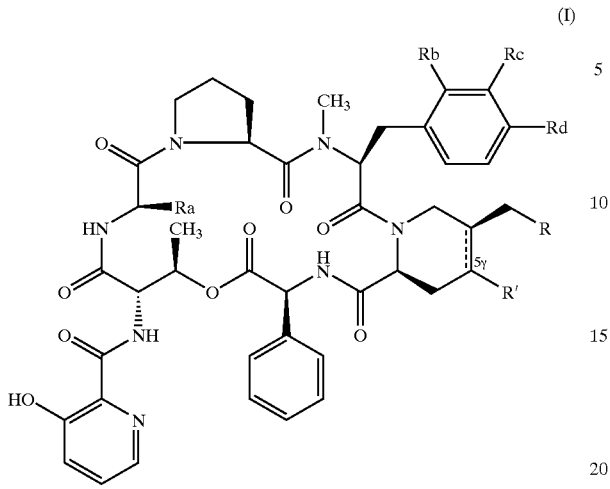

wherein:
R is chosen from —$NR_1R_2$ and —$SR_3$, wherein:
$R_1$ and $R_2$, which may be identical or different, are independently chosen from hydrogen and the radicals:
alkyl having from 1 to 8 carbons, which is unsubstituted or substituted with hydroxyl;
alkenyl having from 3 to 8 carbons;
cycloalkyl having from 3 to 8 carbons;
alkyloxy having from 1 to 8 carbons;
dialkylamino;
phenylalkyl, which is unsubstituted or substituted with one or more halogen atoms or radicals chosen from alkyl, hydroxyalkyl, alkyloxy, and dialkylamino;
saturated and unsaturated 3- to 8-membered heterocyclylalkyl containing one or more hetero atoms chosen from nitrogen, sulphur and oxygen; and
dialkylaminoalkyl;
or, alternatively,
$R_1$ and $R_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;
$R_3$ is chosen from:
alkyl radicals having 1 to 8 carbons and cycloalkyl radicals having 3 to 8 carbons, both of which are substituted with a radical:
—$NR_1R_2$, wherein $R_1$ and $R_2$, which may be identical or different, are chosen from hydrogen and alkyl radicals, or form, together with the nitrogen atom to which they are attached, a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains
one or more hetero atoms chosen from oxygen, sulphur, and nitrogen;
or, alternatively,
$R_3$ is chosen from 3- to 7-membered, saturated and unsaturated, monocyclic and polycyclic, heterocyclyl and heterocyclylmethyl radicals, and which are unsubstituted or substituted with one or more alkyl radicals;

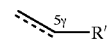

is an unsaturated ring residue which is unsubstituted at 5γ:

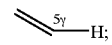

or a saturated ring residue which is substituted at 5γ with a fluoro radical:

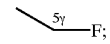

Ra is chosen from methyl and ethyl radicals; and
Rb, Rc, and Rd have one of the definitions below:
1) Rb and Rc are both hydrogen; and
Rd is chosen from hydrogen and methylamino and dimethylamino radicals;
2) Rb is hydrogen;
Rc is chosen from hydrogen, chlorine, and bromine atoms, and from alkenyl radicals having from 3 to 5 carbons; and Rd is a radical —NMe-R'", wherein R'" is chosen from the radicals:
alkyl, hydroxyalkyl having from 2 to 4 carbons, and alkenyl having from 2 to 8 carbons, which are unsubstituted or substituted with one or more radicals chosen from:
phenyl;
cycloalkyl having from 3 to 6 carbons;
methyl;
benzyl; and
substituted benzyl, which is substituted with one or more substitutents chosen from:

halogen atoms, and hydroxyl, alkyl, alkyloxy, alkylthio, alkylsulphinyl, alkylsulphonyl, amino, alkylamino and dialkylamino radicals; and heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:

alkyl, alkenyl having from 2 to 8 carbons, cycloalkyl having from 3 to 6 carbons, saturated and unsaturated 4- to 6-membered heterocyclyl, phenyl, substituted phenyl as defined above for the definition of $R_1$, and benzyl radicals;

or, alternatively,

R''' is chosen from cyanomethyl and carboxymethyl radicals, and from —CORe and —CH$_2$CORe, wherein Re is —OR'e, and wherein R'e is chosen from:
alkyl having from 1 to 6 carbons;
alkenyl having from 2 to 6 carbons;
benzyl;
phenyl
tolyl; and
heterocyclylmethyl radicals, wherein the heterocyclyl portion is 5- or 6-membered and contains 1 or 2 hetero atoms chosen from sulphur, oxygen and nitrogen;
or, alternatively, Re is chosen from:
alkylamino;
alkylmethylamino; and
heterocyclylamino and heterocyclylmethylamino radicals, wherein the heterocyclyl portion is saturated and 5- or 6-membered and contains 1 or 2 hetero atoms chosen from sulphur, oxygen, and nitrogen, and which are unsubstituted or substituted with a radical chosen from alkyl, benzyl, and alkyloxycarbonyl radicals;

3) Rb is hydrogen;
Rd is chosen from —NHCH$_3$ and —N(CH$_3$)$_2$ radicals; and
Rc is chosen from chlorine and bromine atoms, and from alkenyl radicals having from 3 to 5 carbons when Rd is —N(CH$_3$)$_2$;

4) Rb and Rd are both hydrogen; and
Rc is chosen from halogen atoms and alkylamino, dialkylamino, alkyloxy, trifluoromethoxy, thioalkyl, alkyl having from 1 to 6 carbons, and trihalomethyl radicals;

5) Rb and Rc are both hydrogen; and
Rd is chosen from halogen atoms, and ethylamino, diethylamino, methylethylamino, alkyloxy, trifluoromethoxy, alkylthio, alkylsulphinyl, alkylsulphonyl, alkyl having from 1 to 6 carbons, phenyl, and trihalomethyl radicals;

6) Rb is hydrogen;
Rc is chosen from halogen atoms and alkylamino, dialkylamino, alkyloxy, trifluoromethoxy, and thioalkyl radicals, and alkyl radicals having 1 to 6 carbons; and
Rd is chosen from halogen atoms and amino, alkylamino, dialkylamino, alkyloxy, trifluoromethoxy, thioalkyl, alkyl having from 1 to 6 carbons, and trihalomethyl radicals; or 7) Rc is hydrogen; and
Rb and Rd are both methyl radicals;

with the proviso that, unless specifically defined, the alkyl and acyl radicals and portions of radicals are straight or branched and contain from 1 to 4 carbon atoms and that the alkenyl radicals also have a straight or branched chain and contained from 2 to 4 carbon atoms;

or a salt thereof;

said process comprising reacting a fluorinating agent with a compound of formula (II):

(II)

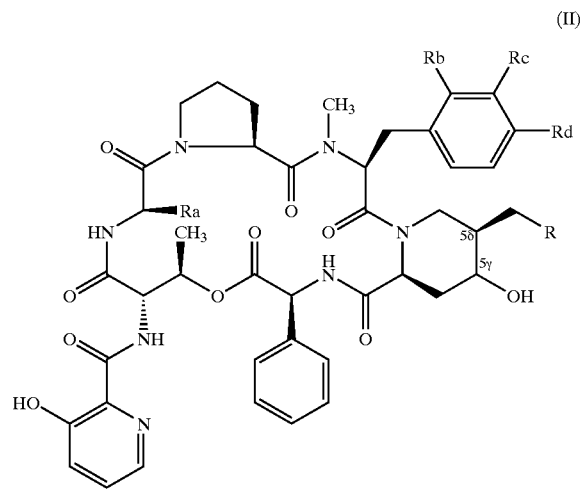

wherein R, Ra, Rb, Rc, and Rd are defined as above, and subsequently separating out a fluorinated derivative wherein

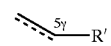

is

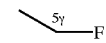

and/or a derivative which is unsaturated in position 5γ,5δ, wherein

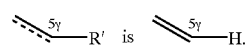

11. A process according to claim 10, wherein the fluorinating agent is chosen from a sulphur fluoride, a sulphur tetrafluoride, hexafluoropropyl diethylamine and N-(2-chloro-1,1,2-trifluoroethyl) diethylamine.

12. A process according to claim 10, wherein the compound of formula (I) is converted into a salt.

13. A process according to claim 10, wherein the separation of the fluoro derivative and of the derivative which is unsaturated in position 5γ,5δ is performed by chromatography or by crystallization.

14. A process for preparing a compound of formula (I):

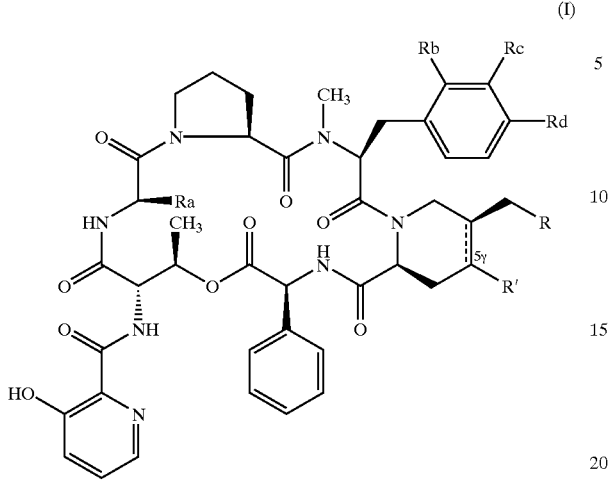

(I)

wherein:
R is chosen from —NR$_1$R$_2$ and —SR$_3$, wherein:
R$_1$ and R$_2$, which may be identical or different, are independently chosen from hydrogen and the radicals:
alkyl having from 1 to 8 carbons, which is unsubstituted or substituted with hydroxyl;
alkenyl having from 3 to 8 carbons;
cycloalkyl having from 3 to 8 carbons;
alkyloxy having from 1 to 8 carbons;
dialkylamino;
phenylalkyl, which is unsubstituted or substituted with one or more halogen atoms or radicals chosen from alkyl, hydroxyalkyl, alkyloxy, and dialkylamino;
saturated and unsaturated 3- to 8-membered heterocyclylalkyl containing one or more hetero atoms chosen from nitrogen, sulphur and oxygen; and
dialkylaminoalkyl;
or, alternatively,
R$_1$ and R$_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;
R$_3$ is chosen from:
alkyl radicals having from 1 to 8 carbons and cycloalkyl radicals having from 3 to 8 carbons, both of which are substituted with a radical:

—NR$_1$R$_2$, wherein R$_1$ and R$_2$, which may be identical or different, are chosen from hydrogen and alkyl radicals, or form, together with the nitrogen atom to which they are attached, a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;
or, alternatively,
R$_3$ is chosen from 3- to 7-membered, saturated and unsaturated, monocyclic and polycyclic, heterocyclyl and heterocyclylmethyl radicals, and which are unsubstituted or substituted with one or more alkyl radicals;

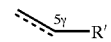

is

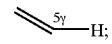

Ra is chosen from methyl and ethyl radicals; and
Rb, Rc, and Rd have one of the definitions below:
1) Rb and Rc are both hydrogen; and
Rd is chosen from hydrogen and methylamino and dimethylamino radicals;
2) Rb is hydrogen;
Rc is chosen from hydrogen, chlorine, and bromine atoms, and from alkenyl radicals having from 3 to 5 carbons; and Rd is a radical —NMe-R''', wherein R''' is chosen from the radicals:
alkyl, hydroxyalkyl having from 2 to 4 carbons, and alkenyl having from 2 to 8 carbons, which are unsubstituted or substituted with one or more radicals chosen from:
phenyl;
cycloalkyl having from 3 to 6 carbons;
methyl;
benzyl; and
substituted benzyl, which is substituted with one or more substitutents chosen from:
halogen atoms, and hydroxyl, alkyl, alkyloxy, alkylthio, alkylsulphinyl, alkylsulphonyl, amino, alkylamino and dialkylamino radicals; and
heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:
alkyl, alkenyl having from 2 to 8 carbons, cycloalkyl having from 3 to 6 carbons, saturated and unsaturated 4- to 6-membered heterocyclyl, phenyl, substituted phenyl as defined above for the definition of $R_1$, and benzyl radicals;

or, alternatively,
R''' is chosen from cyanomethyl and carboxymethyl radicals, and from —CORe and —CH$_2$CORe, wherein Re is —OR'e, and wherein R'e is chosen from:
alkyl having from 1 to 6 carbons;
alkenyl having from 2 to 6 carbons;
benzyl;
phenyl;
tolyl; and
heterocyclylmethyl radicals, wherein the heterocyclyl portion is 5- or 6-membered and contains 1 or 2 hetero atoms chosen from sulphur, oxygen and nitrogen;
or, alternatively, Re is chosen from:
alkylamino;
alkylmethylamino; and
heterocyclylamino and heterocyclylmethylamino radicals, wherein the heterocyclyl portion is saturated and 5- or 6-membered and contains 1 or 2 hetero atoms chosen from sulphur, oxygen, and nitrogen, and which are unsubstituted or substituted with a radical chosen from alkyl, benzyl, and alkyloxycarbonyl radicals;

3) Rb is hydrogen;
Rd is chosen from —NHCH$_3$ and —N(CH$_3$)$_2$ radicals; and
Rc is chosen from chlorine and bromine atoms, and from alkenyl radicals having from 3 to 5 carbons when Rd is —N(CH$_3$)$_2$;

4) Rb and Rd are both hydrogen; and
Rc is chosen from halogen atoms and alkylamino, dialkylamino, alkyloxy, trifluoromethoxy, thioalkyl, alkyl having from 1 to 6 carbons, and trihalomethyl radicals;

5) Rb and Rc are both hydrogen; and
Rd is chosen from halogen atoms, and ethylamino, diethylamino, methylethylamino, alkyloxy, trifluoromethoxy, alkylthio, alkylsulphinyl, alkylsulphonyl, alkyl having from 1 to 6 carbons, phenyl, and trihalomethyl radicals;

6) Rb is hydrogen;
Rc is chosen from halogen atoms and alkylamino, dialkylamino, alkyloxy, trifluoromethoxy, and thioalkyl radicals, and alkyl radicals having from 1 to 6 carbons; and
Rd is chosen from halogen atoms and amino, alkylamino, dialkylamino, alkyloxy, trifluoromethoxy, thioalkyl, alkyl having from 1 to 6 carbons, and trihalomethyl radicals; or 7) Rc is hydrogen; and
Rb and Rd are both methyl radicals;
with the proviso that, unless specifically defined, the alkyl and acyl radicals and portions of radicals are straight or branched and contain from 1 to 4 carbon atoms and that the alkenyl radicals also have a straight or branched chain and contain from 2 to 4 carbon atoms;
or a salt thereof;

said process comprising reacting a thionyl halide, in the presence of a nitrogenous base, with a compound of formula (II):

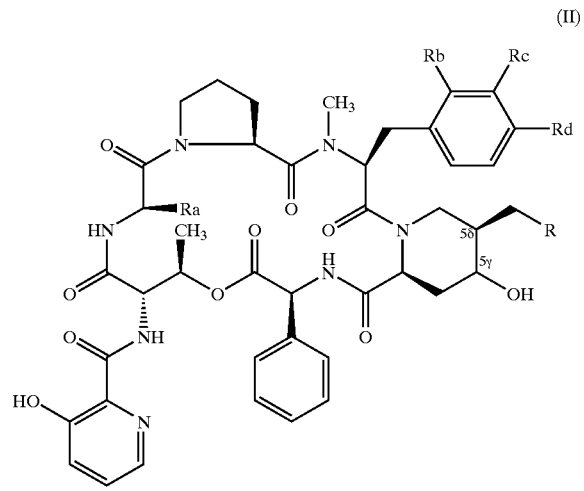

(II)

wherein R, Ra, Rb, Rc, and Rd are defined as above.

15. A process according to claim 14, wherein the compound of formula (I) is converted into a salt.

16. A process for preparing a compound of formula (I):

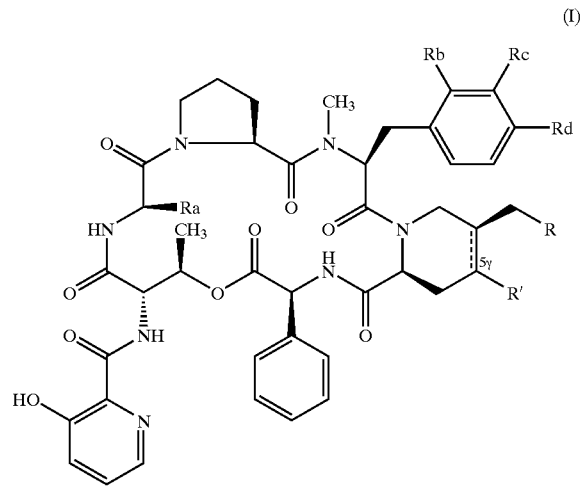

(I)

wherein:
R is chosen from —NR$_1$R$_2$ and —SR$_3$, wherein:
R$_1$ and R$_2$, which may be identical or different, are independently chosen from hydrogen and the radicals:
alkyl having from 1 to 8 carbons, which is unsubstituted or substituted with hydroxyl;
alkenyl having from 3 to 8 carbons;
cycloalkyl having from 3 to 8 carbons;
alkyloxy having from 1 to 8 carbons;
dialkylamino;
phenylalkyl, which is unsubstituted or substituted with one or more halogen atoms or radicals chosen from alkyl, hydroxyalkyl, alkyloxy, and dialkylamino;
saturated and unsaturated 3- to 8-membered heterocyclylalkyl containing one or more hetero atoms chosen from nitrogen, sulphur and oxygen; and
dialkylaminoalkyl;

or, alternatively,

R$_1$ and R$_2$, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;

R$_3$ is chosen from:
alkyl radicals having from 1 to 8 carbons and cycloalkyl radicals having from 3 to 8 carbons, both of which are substituted with a radical;
—NR$_1$R$_2$, wherein R$_1$ and R$_2$, which may be identical or different, are chosen from hydrogen and alkyl radicals, or form, together with the nitrogen atom to which they are attached, a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
hydroxyl;
alkyl;
phenyl, which is unsubstituted or substituted with a halogen atom;
phenylalkyl;
phenylalkenyl, the alkenyl portion having from 2 to 4 carbons;
hydroxyalkyl;
acyl;
alkyloxycarbonyl; and
heterocyclyl and heterocyclylcarbonyl, wherein the heterocyclyl portion is 4- to 6-membered, saturated or unsaturated, and contains one or more hetero atoms chosen from oxygen, sulphur, and nitrogen;

or, alternatively,
R$_3$ is chosen from 3- to 7-membered, saturated and unsaturated, monocyclic and polycyclic, heterocyclyl and heterocyclylmethyl radicals, and which are unsubstituted or substituted with one or more alkyl radicals;

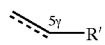

is

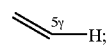

Ra is chosen from methyl and ethyl radicals; and
Rb, Rc, and Rd have one of the definitions below:
1) Rb and Rc are both hydrogen; and
Rd is chosen from hydrogen and methylamino and dimethylamino radicals;
2) Rb is hydrogen;
Rc is chosen from hydrogen, chlorine, and bromine atoms, and from alkenyl radicals having from 3 to 5 carbons; and Rd is a radical —NMe-R‴, wherein R‴ is chosen from the radicals:
alkyl, hydroxyalkyl having from 2 to 4 carbons, and alkenyl having from 2 to 8 carbons, which are unsubstituted or substituted with one or more radicals chosen from:
phenyl;
cycloalkyl having from 3 to 6 carbons;
methyl;
benzyl; and
substituted benzyl, which is substituted with one or more substitutents chosen from:
halogen atoms, and hydroxyl, alkyl, alkyloxy, alkylthio, alkylsulphinyl, alkylsulphonyl, amino, alkylamino and dialkylamino radicals; and
heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:
alkyl, alkenyl having from 2 to 8 carbons, cycloalkyl having from 3 to 6 carbons, saturated and unsaturated 4- to 6-membered heterocyclyl, phenyl, substituted phenyl as defined above for the definition of R$_1$, and benzyl radicals;
or, alternatively,
R‴ is chosen from cyanomethyl and carboxymethyl radicals, and from —CORe and —CH$_2$CORe, wherein Re is —OR'e, and wherein R'e is chosen from:
alkyl having from 1 to 6 carbons;
alkenyl having from 2 to 6 carbons;
benzyl;
phenyl;
tolyl; and
heterocyclylmethyl radicals, wherein the heterocyclyl portion is 5- or 6-membered and contains 1 or 2 hetero atoms chosen from sulphur, oxygen and nitrogen;
or, alternatively, Re is chosen from:
alkylamino;
alkylmethylamino; and
heterocyclylamino and heterocyclylmethylamino radicals, wherein the heterocyclyl portion is saturated and 5- or 6-membered and contains 1 or 2 hetero atoms chosen from sulphur, oxygen, and nitrogen, and which are unsubstituted or substituted with a radical chosen from alkyl, benzyl, and alkyloxycarbonyl radicals;
3) Rb is hydrogen;
Rd is chosen from —NHCH$_3$ and —N(CH$_3$)$_2$ radicals; and Rc is chosen from chlorine and bromine atoms, and from alkenyl radicals having from 3 to 5 carbons when Rd is —N(CH$_3$)$_2$;

4) Rb and Rd are both hydrogen; and
Rc is chosen from halogen atoms and alkylamino, dialkylamino, alkyloxy, trifluoromethoxy, thioalkyl, alkyl having from 1 to 6 carbons, and trihalomethyl radicals;

5) Rb and Rc are both hydrogen; and
Rd is chosen from halogen atoms, and ethylamino, diethylamino, methylethylamino, alkyloxy, trifluoromethoxy, alkylthio, alkylsulphinyl, alkylsulphonyl, alkyl having from 1 to 6 carbons, phenyl, and trihalomethyl radicals;

6) Rb is hydrogen;
Rc is chosen from halogen atoms and alkylamino, dialkylamino, alkyloxy, trifluoromethoxy, and thioalkyl radicals, and alkyl radicals having from 1 to 6 carbons; and
Rd is chosen from halogen atoms and amino, alkylamino, dialkylamino, alkyloxy, trifluoromethoxy, thioalkyl, alkyl having from 1 to 6 carbons, and trihalomethyl radicals; or 7) Rc is hydrogen; and
Rb and Rd are both methyl radicals;
with the proviso that, unless specifically defined, the alkyl and acyl radicals and portions of radicals are straight or branched and contain from 1 to 4 carbon atoms and that the alkenyl radicals also have a straight or branched chain and contain from 2 to 4 carbon atoms;

or a salt thereof;

said process comprising reacting an amine HNR$_1$R$_2$ or a thiol HS-R$_3$ with a halogenated compound of formula (IV):

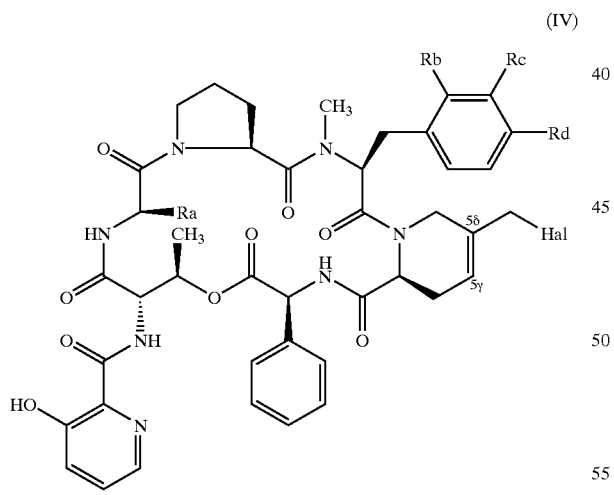

(IV)

wherein Ra, Rb, Rc, and Rd are defined as above and Hal represents a halogen atom.

17. A process according to claim 16, wherein the compound of formula (I) is converted into a salt.

18. A composition comprising at least one compound of formula (I) according to claim 1, wherein said compound of formula (I) is present in pure form, in combination with at least one pharmaceutically acceptable diluent or adjuvant.

19. A composition comprising at least one compound of formula (I) according to claim 1, wherein said compound of formula (I) is present in combination with at least one A-group streptogramin compound, or a salt thereof, in combination with at least one pharmaceutically acceptable diluent or adjuvant.

20. A composition according to claim 19, wherein the at least one A-group streptogramin compound is chosen from pristinamycin IIA, pristinamycin IIB, pristinamycin IIC, pristinamycin IID, pristinamycin IIE, pristinamycin IIF, pristinamycin IIG, and semisynthetic derivatives of A-group streptogramins, which comprise semisynthetic compounds of formula (α):

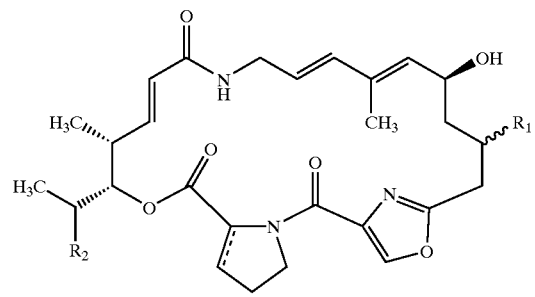

(α)

wherein:
R$_1$ is a radical —NR'R", wherein:
R' is chosen from a hydrogen atom and a methyl radical;
R" is chosen from a hydrogen atom, alkyl, cycloalkyl, allyl, propargyl, and benzyl radicals, and —OR'" radicals, wherein R'" is chosen from:
a hydrogen atom, alkyl, cycloalkyl, allyl, propargyl, benzyl and —NR$_3$R$_4$ radicals, wherein:
R$_3$ and R$_4$ are each methyl radicals, or form, together with the nitrogen atom to which they are attached, a saturated or unsaturated, 4- or 5-membered heterocycle optionally containing at least one additional hetero atom chosen from nitrogen, oxygen, and sulphur;
R$_2$ is chosen from a hydrogen atom and methyl and ethyl radicals; and the bond - - - is a single or double bond;
or a salt thereof; and comprise compounds of formula (β):

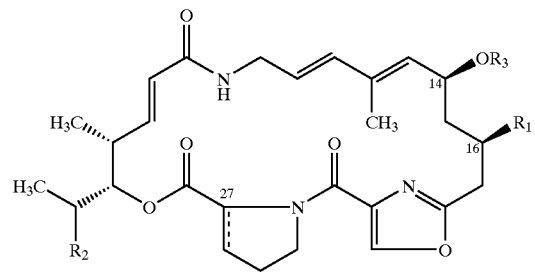

(β)

wherein:
R$_1$ is chosen from a halogen atom and azido and thiocyanato radicals;
R$_2$ is chosen from hydrogen and methyl and ethyl radicals;
R$_3$ is chosen from hydrogen and aliphatic, cycloaliphatic, aromatic, araliphatic, heterocyclic and heterocyclylaliphatic ester residues which may be substituted or unsubstituted; and the bond --- represents a single bond (27R stereochemistry) or a double bond;

or a salt thereof.

21. A composition according to claim 20, wherein, in the semisynthetic derivatives of formula (β), the ester residue $R_3$ is chosen from:

a radical $R'_3$—CO—, wherein $R'_3$ is chosen from:
phenyl and phenylalkyl radicals, which are unsubstituted or substituted on the phenyl radical with one or more radicals chosen from:
alkyl radicals, which may be unsubstituted or substituted with a radical NR"R"', wherein the radicals R" and R"', which may be identical or different, are chosen from:
a hydrogen atom and alkyl radicals which can form, together with the nitrogen atom to which they are attached, saturated and unsaturated 3- to 8-membered heterocyclyl radicals, optionally comprising an additional hetero atom chosen from oxygen, sulphur, and nitrogen, it being possible for the heterocycle itself to be substituted with one or more radicals chosen from saturated and unsaturated 3- to 8-membered alkyl, hydroxyalkyl, alkyloxyalkyl, alkyloxycarbonylalkyl, aryl, heterocyclyl, heterocyclylalkyl and —CH$_2$—CO—N R""R""', wherein R"" and R""', which may be identical or different, are chosen from a hydrogen atom and alkyl radicals which can form, together with the nitrogen atom to which they are attached, saturated and unsaturated 3- to 8-membered heterocyclyl radicals, optionally comprising an additional hetero atom chosen from oxygen, sulphur, and nitrogen, it being possible for the heterocycle itself to be substituted with one or more radicals chosen from saturated and unsaturated 3- to 8-membered alkyl, hydroxyalkyl, alkyloxyalkyl, alkyloxycarbonylalkyl, aryl, heterocyclyl, and heterocyclylalkyl;

or, alternatively,
R" and R"' are independently chosen from:
saturated and unsaturated 3- to 8-membered hydroxyalkyl, phenyl and heterocyclylalkyl radicals, a radical —CO—NR"R"', alkyl radicals optionally substituted with NR"R"', and acyl radicals optionally substituted with NR"R"', wherein NR"R"' is defined as above;

or, alternatively,
$R'_3$ is chosen from phenyl and phenylalkyl radicals which are substituted on the phenyl radical with one or more radicals chosen from:
alkyl, which is unsubstituted or substituted with alkyloxy and alkylthio radicals, themselves optionally bearing a carboxyl radical or a radical NR"R"' defined as above, or chosen from acyloxy radicals, which can be substituted with NR"R"' defined as above;

or, alternatively,
$R'_3$ is chosen from alkyl and cycloalkyl radicals which are unsubstituted or substituted with at least one radical chosen from carboxyl, carboxyalkyldisulphanyl, NR"R"', —CH$_2$—NR"R"', —CO—NR"R"', alkyloxycarbonyl, alkyloxy, and alkyldisulphanyl radicals, which are unsubstituted or substituted with at least one radical chosen from: NR"R"' and —CO—NR"R"', wherein NR"R"' is defined as above;

or, alternatively,
$R'_3$ is chosen from saturated and unsaturated, 3- to 8-membered heterocyclyl radicals which are unsubstituted or substituted with at least one radical chosen from alkyl and acyl radicals, both of which are unsubstituted or substituted with NR"R"', wherein NR"R"' is defined as above.

22. A composition comprising at least one compound of formula (I) chosen from:

5δ-(1-morpholino)methyl-5δ,5γ-dehydropristinamycin $I_E$;

5δ-[N-methyl-N-2-(1,3-dioxolanyl)methyl]aminomethyl-5δ,5γ-dehydropristinamycin $I_E$;

5δ-morpholinomethyl-4ζ-methylamino-4ζ-dedimethylamino-5δ,5γ-dehydropristinamycin $I_E$;

5δ-morpholinomethyl-4ζ-methylamino-4ζ-dedimethylamino-5δ,5γ-dehydro-4ε-chloropristinamycin $I_E$;

5δ-[bis(2-methoxyethyl)aminomethyl]-5δ,5γ-dehydropristinamycin $I_E$;

4ε-chloro-5δ-(diethylaminoethylthiomethyl)-5δ,5γ-dehydropristinamycin $I_E$;

5δ-(diethylaminoethylthiomethyl)-4ζ-methylamino-4ζ-dedimethylamino-5δ,5γ-dehydropristinamycin $I_E$;

4ε-chloro-5δ-(diethylaminoethylthiomethyl)-4ζ-methylamino)-4ζ-dedimethylamino-5δ,5γ-dehydropristinamycin $I_E$;

5δ-(3-diethylaminopropylthiomethyl)-5δ,5γ-dehydropristinamycin $I_E$;

4ε-chloro-5δ-(3-diethylaminopropylthiomethyl)-5δ,5γ-dehydropristinamycin $I_E$;

5δ-(3-diethylaminopropylthiomethyl)-4ζ-methylamino-4ζ-dedimethylamino-5δ,5γ-dehydropristinamycin $I_E$;

4ε-chloro-5δ-(3-diethylaminopropylthiomethyl)-4ζ-methylamino)-4ζ-dedimethylamino-5δ,5γ-dehydropristinamycin $I_E$;

5δ-(dimethylaminoethylthiomethyl)-5δ,5γ-dehydropristinamycin $I_E$;

4ε-chloro-5δ-(dimethylaminoethylthiomethyl)-5δ,5γ-dehydropristinamycin $I_E$;

5δ-(dimethylaminoethylthiomethyl)-4ζ-methylamino-4ζ-dedimethylamino-5δ,5γ-dehydropristinamycin $I_E$;

4ε-chloro-5δ-(dimethylamino-5δ,5γ-dehydropristinamycin $I_E$;

4ε-chloro-5δ-(1-methyl-2-imidazolylthiomethyl)-5δ,5γ-dehydropristinamycin $I_E$;

5δ-(1-methyl-2-imidazolylthiomethyl)-4ζ-methylamino-4ζ-dedimethylamino-5δ,5γ-dehydropristinamycin $I_E$;

4ε-chloro-5δ-(1-methyl-2-imidazolylthiomethyl)-4ζ-methylamino-4ζ-dedimethylamino-5δ,5γ-dehydropristinamycin $I_E$;

5δ-(morpholinoethylthiomethyl)-5δ,5γ-dehydropristinamycin $I_E$;

4ε-chloro-5δ-(morpholinoethylthiomethyl)-5δ,5γ-dehydropristinamycin $I_E$;

5δ-(morpholinoethylthiomethyl)-4ζ-methylamino-4ζ-dedimethylamino-5δ,5γ-dehydropristinamycin $I_E$;

4ε-chloro-5δ-(morpholinoethylthiomethyl)-4ζ-methylamino-4ζ-dedimethylamino-5δ,5γ-dehydropristinamycin $I_E$;

4ε-chloro-5δ-(2-piperidinoethyl)thiomethyl-5δ,5γ-dehydropristinamycin I$_E$;

5δ-(2-piperidinoethyl)thiomethyl-4ζ-methylamino-4ζ-dedimethylamino-5δ,5γ-dehydropristinamycin I$_E$;

4ε-chloro-5δ-(2-piperidinoethyl)thiomethyl-4ζ-methylamino-4ζ-dedimethylamino-5δ,5γ-dehydropristinamycin I$_E$;

5δ-(3-piperidinopropyl)thiomethyl-5δ,5γ-dehydropristinamycin I$_E$;

4ε-chloro-5δ-(3-piperidinopropyl)thiomethyl-5δ,5γ-dehydropristinamycin I$_E$;

5δ-(3-piperidinopropyl)thiomethyl-4ζ-methylamino-4ζ-dedimethylamino-5δ,5γ-dehydropristinamycin I$_E$;

4ε-chloro-5δ-(3-piperidinopropyl)thiomethyl-4ζ-methylamino-4ζ-dedimethylamino-5δ,5γ-dehydropristinamycin I$_E$;

4ε-chloro-5δ-(4-pyridylmethylthiomethyl)-5δ,5γ-dehydropristinamycin I$_E$;

5δ-(4-pyridylmethylthiomethyl)-4ζ-methylamino-4ζ-dedimethylamino-5δ,5γ-dehydropristinamycin I$_E$;

4ε-chloro-5δ-(4-pyridylmethylthiomethyl)-4ζ-methylamino-4ζ-dedimethylamino-5δ,5γ-dehydropristinamycin I$_E$;

4ε-chloro-5δ-(3-pyridylmethylthiomethyl)-5δ,5γ-dehydropristinamycin I$_E$;

5δ-(3-pyridylmethylthiomethyl)-4ζ-methylamino-4ζ-dedimethylamino-5δ,5γ-dehydropristinamycin I$_E$;

4ε-chloro-5δ-(3-pyridylmethylthiomethyl)-4ζ-methylamino-4ζ-dedimethylamino-5δ,5γ-dehydropristinamycin I$_E$;

5δ-(2-pyridylmethylthiomethyl)-5δ,5γ-dehydropristinamycin I$_E$;

4ε-chloro-5δ-(2-pyridylmethylthiomethyl)-5δ,5γ-dehydropristinamycin I$_E$;

5δ-(2-pyridylmethylthiomethyl)-4ζ-methylamino-4ζ-dedimethylamino-5δ,5γ-dehydropristinamycin I$_E$;

4ε-chloro-5δ-(2-pyridylmethylthiomethyl)-4ζ-methylamino-4ζ-dedimethylamino-5δ,5γ-dehydropristinamycin I$_E$;

5δ-{[2-(4-methylpiperazin-1-yl)ethyl]thiomethyl}-5δ,5γ-dehydropristinamycin I$_E$;

4ε-chloro-5δ-[2-(4-methylpiperazin-1-yl)ethyl]thiomethyl-5δ,5γ-dehydropristinamycin I$_E$;

5δ-{[2-(4-methylpiperazin-1-yl)ethyl]thiomethyl}-4ζ-methylamino-4ζ-dedimethylamino-5δ,5γ-dehydropristinamycin I$_E$;

4ε-chloro-5δ-{[2-(4-methylpiperazin-1-yl)ethyl]thiomethyl}-4ζ-methylamino-4ζ-dedimethylamino-5δ,5γ-dehydropristinamycin I$_E$;

5δ-(butoxycarbonylaminoethylthiomethyl)-5δ,5γ-dehydropristinamycin I$_E$;

4ε-chloro-5δ-(butoxycarbonylaminoethylthiomethyl)-5δ,5γ-dehydropristinamycin I$_E$;

5δ-(butoxycarbonylaminomethylthioethyl)-4ζ-methylamino-4ζ-dedimethylamino-5δ,5γ-dehydropristinamycin I$_E$;

4ε-chloro-5δ-(butoxycarbonylaminoethylthiomethyl)-4ζ-methylamino-4ζ-dedimethylamino-5δ,5γ-dehydropristinamycin I$_E$;

5δ-(aminoethylthiomethyl)-5δ,5γ-dehydropristinamycin I$_E$;

4-chloro-5δ-(aminoethylthiomethyl)-5δ,5γ-dehydropristinamycin I$_E$;

5δ-(aminomethylthioethyl)-4ζ-methylamino-4ζ-dedimethylamino-5δ,5γ-dehydropristinamycin I$_E$;

4ε-chloro-54-(aminoethylthiomethyl)-4ζ-methylamino-4-dedimethylamino 5δ,5γ-dehydropristinamycin I$_E$;

5δ-(pyrrolidinoethylthiomethyl)-5δ,5γ-dehydropristinamycin I$_E$;

4ε-chloro-5δ-(pyrrolidinoethylthiomethyl)-5δ,5γ-dehydropristinamycin I$_E$;

5δ-(pyrrolidinoethylthiomethyl)-4ζ-methylamino-4ζ-dedimethylamino-5δ,5γ-dehydropristinamycin I$_E$;

4ε-chloro-5δ-(pyrrolidinoethylthiomethyl)-4ζ-methylamino-4ζ-dedimethylamino-5δ,5γ-dehydropristinamycin I$_E$;

5δ-(diisopropylaminoethylthiomethyl)-5δ,5γ-dehydropristinamycin I$_E$;

4ε-chloro-5δ-(diisopropylaminoethylthiomethyl)-5δ,5γ-dehydropristinamycin I$_E$;

5δ-(diisopropylaminoethylthiomethyl)-4ζ-methylamino-4ζ-dedimethylamino-5δ,5γ-dehydropristinamycin I$_E$;

4ε-chloro-5δ-(diisopropylaminoethylthiomethyl)-4ζ-methylamino-4ζ-dedimethylamino-5δ,5γ-dehydropristinamycin I$_E$;

5δ-(N-ethyl-N-methylaminoethylthiomethyl)-5δ,5γ-dehydropristinamycin I$_E$

4ε-chloro-5δ-(N-ethyl4-N-methylamnOethylthiomethyl)-5δ,5γ-dehydropristinamycin I$_E$;

5δ-(N-ethyl-N-methylaminoethylthiomethyl)-4ζ-methylamino-4ζ-dedimethylamino-5δ,5γ-dehydropristinamycin I$_E$;

4ε-chloro-5δ-(N-ethyl-N-methylaminoethylthiomethyl)-4ζ-methylamino-4ζ-dedimethylamino-5δ,5γ-dehydropristinamycin I$_E$;

5δ-((2R)-3-diethylaminopropyl-2-thiomethyl)-5δ,5γ-dehydropristinamycin I$_E$;

4ε-chloro-5δ-((2R)-3-diethylaminopropyl-2-thiomethyl)-5δ,5γ-dehydropristinamycin I$_E$;

5δ-((2R)-3-diethylaminopropyl-2-thiomethyl)-4ζ-methylamino-4ζ-dedimethylamino-5δ,5γ-dehydropristinamycin I$_E$;

4ε-chloro-5δ-((2R)-3-diethylaminopropyl-2-thiomethyl)-4ζ-methylamino-4ζ-dedimethylamino-5δ,5γ-dehydropristinamycin I$_E$;

5δ-((2S)-3-diethylaminopropyl-2-thiomethyl)-5δ,5γ-dehydropristinamycin I$_E$;

4ε-chloro-5δ-((2S)-3-diethylaminopropyl-2-thiomethyl)-5δ,5γ-dehydropristinamycin I$_E$;

5δ-((2S)-3-diethylaminopropyl-2-thiomethyl)-4ζ-methylamino-4ζ-dedimethylamino-5δ,5γ-dehydropristinamycin I$_E$; and 4ε-chloro-5δ-((2S)-3-diethylaminopropyl-2-thiomethyl)-4ζ-methylamino-4ζ-dedimethylamino-5δ,5γ-dehydropristinamycin I$_E$;

or a salt thereof, in combination with at least one pharmaceutically acceptable diluent or adjuvant.

23. A composition according to claim 22, said composition comprising at least one compound of formula (I) chosen from:

5δ-(1-morpholino)methyl-5δ,5γ-dehydropristinamycin I$_E$;

5δ-[N-methyl-N-2-(1,3-dioxolanyl)methyl]aminomethyl-5δ,5γ-dehydropristinamycin I$_E$;

5δ-morpholinomethyl-4ζ-methylamino-4ζ-dedimethylamino-5δ,5γ-dehydropristinamycin I$_E$;

5δ-morpholinomethyl-4ζ-methylamino-4ζ-dedimethylamino-5δ,5γ-dehydro-4ε-chloropristinamycin $I_E$; and 5δ-[bis(2-methoxyethyl)aminomethyl]-5δ,5γ-dehydropristinamycin $I_E$.

24. A process for treating or preventing a bacterial infection, said process comprising administering to a subject in need thereof an effective amount at least one compound of formula (I) according to claim 1, or a salt thereof.

25. A combination comprising a compound of formula (I):

(I)

wherein:
R is chosen from —NR₁R₂ and —SR₃, wherein:
  R₁ and R₂, which may be identical or different, are independently chosen from hydrogen and the radicals:
    alkyl having from 1 to 8 carbons, which is unsubstituted or substituted with hydroxyl;
    alkenyl having from 3 to 8 carbons;
    cycloalkyl having from 3 to 8 carbons;
    alkyloxy having from 1 to 8 carbons;
    dialkylamino;
    phenylalkyl, which is unsubstituted or substituted with one or more halogen atoms or radicals chosen from alkyl, hydroxyalkyl, alkyloxy, and dialkylamino;
    saturated and unsaturated 3- to 8-membered heterocyclylalkyl containing one or more hetero atoms chosen from nitrogen, sulphur and oxygen; and
    dialkylaminoalkyl;
  or, alternatively,
  R₁ and R₂, together with the nitrogen atom to which they are attached, form a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
    hydroxyl;
    alkyl;
    phenyl, which is unsubstituted or substituted with a halogen atom;
    phenylalkyl;
    phenylalkenyl, the alkenyl portion having from 2 to 4 carbons;
    hydroxyalkyl;
    acyl;
    alkyloxycarbonyl; and
    heterocyclyl and heterocyclylcarbonyl, wherein the heterocyclyl portion is 4- to 6-membered, saturated or unsaturated, and contains one or more hetero atoms chosen from oxygen, sulphur, and nitrogen;
  R₃ is chosen from:
    alkyl radicals having from 1 to 8 carbons and cycloalkyl radicals having from 3 to 8 carbons, both of which are substituted with a radical:
      —NR₁R₂, wherein R₁ and R₂, which may be identical or different, are chosen from hydrogen and alkyl radicals, or form, together with the nitrogen atom to which they are attached, a ring chosen from 3- to 12-membered, saturated, partially saturated, and unsaturated, monocyclic and polycyclic heterocycles optionally containing at least one additional hetero atom chosen from oxygen, sulphur, and nitrogen, and which are unsubstituted or substituted with one or more radicals chosen from:
        hydroxyl;
        alkyl;
        phenyl, which is unsubstituted or substituted with a halogen atom;
        phenylalkyl;
        phenylalkenyl, the alkenyl portion having from 2 to 4 carbons;
        hydroxyalkyl;
        acyl;
        alkyloxycarbonyl; and
        heterocyclyl and heterocyclylcarbonyl, wherein the heterocyclyl portion is 4- to 6-membered, saturated or unsaturated, and contains one or more hetero atoms chosen from oxygen, sulphur, and nitrogen;
  or, alternatively,
    R₃ is chosen from 3- to 7-membered, saturated and unsaturated, monocyclic and polycyclic, heterocyclyl and heterocyclylmethyl radicals, and which are unsubstituted or substituted with one or more alkyl radicals;

is an unsaturated ring residue which is unsubstituted at 5γ:

or a saturated ring residue which is substituted at 5γ with a fluoro radical:

Ra is chosen from methyl and ethyl radicals; and
Rb, Rc, and Rd have one of the definitions below:
1) Rb and Rc are both hydrogen; and
  Rd is chosen from hydrogen and methylamino and dimethylamino radicals;
2) Rb is hydrogen;
  Rc is chosen from hydrogen, chlorine, and bromine atoms, and from alkenyl radicals having from 3 to 5 carbons; and Rd is a radical —NMe-R''', wherein R''' is chosen from the radicals:

alkyl hydroxyalkyl having from 2 to 4 carbons, and
alkenyl having from 2 to 8 carbons, which are
unsubstituted or substituted with one or more
radicals chosen from:
  phenyl;
  cycloalkyl having from 3 to 6 carbons;
  methyl;
  benzyl; and
  substituted benzyl, which is substituted with one or more substitutents chosen from:
    halogen atoms, and hydroxyl, alkyl, alkyloxy, alkylthio, alkylsulphinyl, alkylsulphonyl, amino, alkylamino and dialkylamino radicals; and
heterocyclylmethyl and heterocyclylethyl, wherein the heterocyclyl portion is saturated or unsaturated and 5- or 6-membered and contains 1 or 2 hetero atoms chosen from sulphur, oxygen, and nitrogen, and which are unsubstituted or substituted with one or more radicals chosen from:
  alkyl, alkenyl having from 2 to 8 carbons, cycloalkyl having from 3 to 6 carbons, saturated and unsaturated 4- to 6-membered heterocyclyl, phenyl, substituted phenyl as defined above for the definition of RI, and benzyl radicals;
or, alternatively,
  R'" is chosen from cyanomethyl and carboxymethyl radicals, and from —CORe and —CH₂CORe, wherein Re is —OR'e, and wherein R'e is chosen from:
    alkyl having from 1 to 6 carbons;
    alkenyl having from 2 to 6 carbons;
    benzyl;
    phenyl;
    tolyl; and
    heterocyclylmethyl radicals, wherein the heterocyclyl portion is 5- or 6-membered and contains 1 or 2 hetero atoms chosen from sulphur, oxygen and nitrogen;
  or, alternatively, Re is chosen from:
    alkylamino;
    alkylmethylamino; and
    heterocyclylamino and heterocyclylmethylamino radicals, wherein the heterocyclyl portion is saturated and 5- or 6-membered and contains 1 or 2 hetero atoms chosen from sulphur, oxygen, and nitrogen, and which are unsubstituted or substituted with a radical chosen from alkyl, benzyl, and alkyloxycarbonyl radicals;
3) Rb is hydrogen;
   Rd is chosen from —NHCH₃ and —N(CH₃)₂ radicals; and
   Rc is chosen from chlorine and bromine atoms, and from alkenyl radicals having from 3 to 5 carbons when Rd is —N(CH₃)₂;
4) Rb and Rd are both hydrogen; and
   Rc is chosen from halogen atoms and alkylamino, dialkylamino, alkyloxy, trifluoromethoxy, thioalkyl, alkyl having from 1 to 6 carbons, and trihalomethyl radicals;

5) Rb and Rc are both hydrogen; and
   Rd is chosen from halogen atoms, and ethylamino, diethylamino, methylethylamino, alkyloxy, trifluoromethoxy, alkylthio, alkylsulphinyl, alkylsulphonyl, alkyl having from 1 to 6 carbons, phenyl, and trihalomethyl radicals;
6) Rb is hydrogen;
   Rc is chosen from halogen atoms and alkylamino, dialkylamino, alkyloxy, trifluoromethoxy, and thioalkyl radicals, and alkyl radicals having from 1 to 6 carbons; and
   Rd is chosen from halogen atoms and amino, alkylamino, dialkylamino, alkyloxy, trifluoromethoxy, thioalkyl, alkyl having from 1 to 6 carbons, and trihalomethyl radicals; or
7) Rc is hydrogen; and
   Rb and Rd are both methyl radicals;
with the proviso that, unless specifically defined, the alkyl and acyl radicals and portions of radicals are straight or branched and contain from 1 to 4 carbon atoms and that the alkenyl radicals also have a straight or branched chain and contain from 2 to 4 carbon atoms;

or a salt thereof;

and an A-group streptogramin compound chosen from pristinamycin IIA, pristinamycin IIB, pristinamycin IIC, pristinamycin IID, pristinamycin IIE, pristinamycin IIF, pristinamycin IIG, and semisynthetic derivatives of A-group streptogramins, which comprise compounds of formula (α):

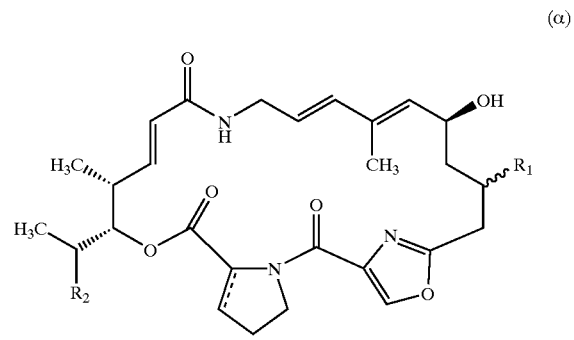

(α)

wherein:
R₁ is a radical —NR'R", wherein:
  R' is chosen from a hydrogen atom and a methyl radical;
  R" is chosen from a hydrogen atom, alkyl, cycloalkyl, allyl, propargyl, and benzyl radicals, and —OR'" radicals, wherein R'" is chosen from:
    a hydrogen atom, alkyl, cycloalkyl, allyl, propargyl, benzyl and —NR₃R₄ radicals, wherein:
      R₃ and R₄ are each methyl radicals, or form, together with the nitrogen atom to which they are attached, a saturated or unsaturated, 4- or 5-membered heterocycle optionally containing an additional hetero atom chosen from nitrogen, oxygen, and sulphur;

$R_2$ is chosen from a hydrogen atom and methyl and and ethyl radicals; and the bond—is a single or double bond; or a salt thereof; and comprise compounds of formula (β):

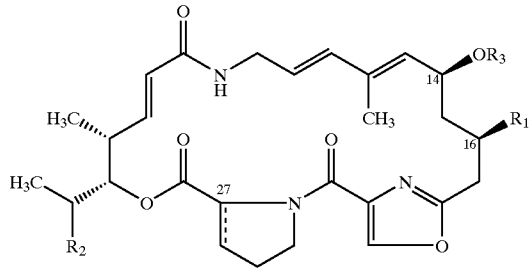

(β)

wherein:

$R_1$ is chosen from a halogen atom and azido and thiocyanato radicals;

$R_2$ is chosen from hydrogen, and methyl and ethyl radicals;

$R_3$ is chosen from hydrogen and aliphatic, cycloaliphatic, aromatic, araliphatic, heterocyclic and heterocyclylaliphatic ester residues which may be substituted or unsubstituted; and the bond—represents a single bond (27R stereochemistry) or a double bond;

or a salt thereof.

26. A combination according to claim 25, wherein said A group streptogramin compound is (16R)-16-deoxo-16-fluoropristinamycin $II_B$ or a salt thereof.

* * * * *

UNITED STATES PATENT AND TRADEMARK OFFICE
CERTIFICATE OF CORRECTION

PATENT NO. : 6,541,451 B1
DATED : April 1, 2003
INVENTOR(S) : Eric Bacque et al.

It is certified that error appears in the above-identified patent and that said Letters Patent is hereby corrected as shown below:

Column 63,
Line 39, "dedimethylamino-5δ,5γdehydropristinamycin $I_E$;" should read
-- dedimethylamino-5δ,5γ-dehydropristinamycin $I_E$; --.

Column 64,
Line 15, "4-chloro-5δ-(2-pyridylmethylthiomethyl)-4ζ-" should read
-- 4∈-chloro-5δ-(2-pyridylmethylthiomethyl)-4ζ- --.

Column 66,
Line 41, "$R_2$ and $R_2$," should read -- $R_1$ and $R_2$, --.

Column 77,
Line 30, "radical;" should read -- radical: --.

Column 81,
Lines 28-29, "-CH$_2$-CO-N R""R""," should read -- -CH$_2$-CO-NR""R"", --.

Column 82,
Line 49, "4∈-chloro-5δ-(dimethylamino-5δ,5γ-" should read -- 4∈-chloro-5δ-(dimethylaminoethylthiomethyl)-4ζ-methylamino)-4ζ-dedimethylamino-,5δ,5γ- --.

Column 83,
Line 66, "4-chloro-5δ-(aminoethylthiomethyl)-5δ,5γ-" should
read -- 4∈-chloro-5δ-(aminoethylthiomethyl)-5δ,5γ- --.

Column 84,
Lines 3-4, "4∈-chloro-54-(aminoethylthiomethyl)-4ζ-methylamino-4-dedimethylamino 5δ,5γ-dehydropristinamycin $I_E$;" should read
-- 4∈-chloro-5δ-(aminoethylthiomethyl)-4ζ-methylamino-4ζ-dedimethylamino-5δ,5γ-dehydropristinamycin $I_E$; --.
Lines 27-28, "4∈-chloro-5δ-(N-ethyl4-N-methylam nOethylthiomethyl)-5δ,5γ-dehydropristinamycin $I_E$;" should read
-- 4∈-chloro-5δ-(N-ethyl-N-methylaminoethylthiomethyl)-5δ,5γ-dehydropristinamycin $I_E$; --.

UNITED STATES PATENT AND TRADEMARK OFFICE
CERTIFICATE OF CORRECTION

PATENT NO. : 6,541,451 B1
DATED : April 1, 2003
INVENTOR(S) : Eric Bacque et al.

It is certified that error appears in the above-identified patent and that said Letters Patent is hereby corrected as shown below:

Column 85,
Line 8, "amount at" should read -- amount of at --.

Column 87,
Line 1, "alkyl hydroxyalkyl" should read -- alkyl, hydroxyalkyl --.
Line 28, "RI," should read -- $R_1$, --.

Column 89,
Lines 1-2, "methyl and and ethyl" should read -- methyl and ethyl --.
Line 2, "bond—is" should read -- bond --- is --.

Column 90,
Line 11, "bond—represents" should read -- bond --- represents --.

Signed and Sealed this

Second Day of December, 2003

JAMES E. ROGAN
*Director of the United States Patent and Trademark Office*